United States Patent
Ghobrial et al.

(10) Patent No.: US 11,220,548 B2
(45) Date of Patent: Jan. 11, 2022

(54) TREATMENT OF C1013G/CXCR4-ASSOCIATED WALDENSTROM'S MACROGLOBULINEMIA WITH AN ANTI-CXCR4 ANTIBODY

(71) Applicants: BRISTOL-MYERS SQUIBB COMPANY, Princeton, NJ (US); DANA-FARBER CANCER INSTITUTE, INC., Boston, MA (US)

(72) Inventors: Irene M. Ghobrial, Wellesley, MA (US); Aldo M. Roccaro, Boston, MA (US); Josephine M. Cardarelli, Wellesley, MA (US); Antonio Sacco, Boston, MA (US)

(73) Assignees: BRISTOL-MYERS SQUIBB COMPANY, Princeton, NJ (US); DANA-FARBER CANCER INSTITUTE, Inc., Boston, MA (US)

(*) Notice: Subject to any disclaimer, the term of this patent is extended or adjusted under 35 U.S.C. 154(b) by 0 days.

(21) Appl. No.: 16/271,569

(22) Filed: Feb. 8, 2019

(65) Prior Publication Data
US 2020/0002428 A1    Jan. 2, 2020

Related U.S. Application Data

(62) Division of application No. 15/034,964, filed as application No. PCT/US2014/064320 on Nov. 6, 2014, now Pat. No. 10,233,248.

(60) Provisional application No. 61/900,898, filed on Nov. 6, 2013.

(51) Int. Cl.
| | |
|---|---|
| *A61P 35/00* | (2006.01) |
| *A61K 39/395* | (2006.01) |
| *C12Q 1/6886* | (2018.01) |
| *C07K 16/28* | (2006.01) |
| *A61K 45/06* | (2006.01) |
| *C07K 14/715* | (2006.01) |
| *A61K 39/00* | (2006.01) |

(52) U.S. Cl.
CPC ...... *C07K 16/2866* (2013.01); *A61K 39/3955* (2013.01); *A61K 45/06* (2013.01); *A61P 35/00* (2018.01); *C12Q 1/6886* (2013.01); *A61K 2039/505* (2013.01); *A61K 2039/545* (2013.01); *A61K 2039/572* (2013.01); *C07K 14/7158* (2013.01); *C07K 2317/21* (2013.01); *C07K 2317/24* (2013.01); *C07K 2317/56* (2013.01); *C07K 2317/565* (2013.01); *C07K 2317/73* (2013.01); *C07K 2317/76* (2013.01); *C12Q 2600/106* (2013.01); *C12Q 2600/156* (2013.01)

(58) Field of Classification Search
CPC ............... C07K 16/28; A61K 39/3955; A61K 39/39558
See application file for complete search history.

(56) References Cited

U.S. PATENT DOCUMENTS 10,233,248 B2 * 3/2019 Ghobrial .............. C12Q 1/6886

FOREIGN PATENT DOCUMENTS

| WO | WO 2008/060367 | 5/2008 |
| WO | WO 2013/071068 | 5/2013 |

OTHER PUBLICATIONS

Morlan et al, 2009 (PLoS One. 4(2): e4584; 11 pages as printed).*
Roccaro et al, 2013. "A Novel Activating Mutation of CXCR4 Plays a Crucial Role in Waldenstrom Macroglobulinemia Biology". Blood. 112(21): 272, dated Nov. 15, 2013; 3 pages as printed (Year: 2013).*
"2013 ASH Annual Meeting and Exposition" page at hematology.org, dated Oct. 28, 2013, no author indicated, 1 page as printed; archived in the Internet Archive at: web.archive.org/web/20131028235024/www.hematology.org/meetings/Annual-Meeting (Year: 2013).*
Alsayed, Y. et al., "Mechanisms of regulation of CXCR4/SDF-1 (CXCL12)-dependent migration and homing in multiple myeloma", Blood, vol. 109, No. 7, pp. 2708-2717 (2007).
Azab, A.K. et al., "CXCR4 inhibitor AMD3100 disrupts the interaction of multiple myeloma cells with the bone marrow microenvironment and enhances their sensitivity to therapy", Blood, vol. 113, No. 18, pp. 4341-4351 (2009).
Azab, F. et al., "Eph-B2/Ephrin-B2 Interaction Plays a Major Role in the Adhesion and Proliferation of Waldenstrom's Macroglobulinemia", Clinical Cancer Research, vol. 18, No. 1, pp. 91-104 (2012).
Cao, Y. et al., "Whole Genome Sequencing Identifies Recurring Somatic Mutations in the C-terminal domain of CXCR4, Including a Gain of Function Mutation in Waldenstrom's Macroglobinemia", Abstract No. 2715, Blood, vol. 120 (2012).
Cao, Y. et al., "Somatic Activating Mutations In CXCR4 Are Common In Patients With Waldenstrom's Macroglobulinemia, and Their Expression In WM Cells Promotes Resistance To Ibrutinib", Abstract No. 4424, Blood, vol. 122, No. 21 (2013).
Ghobrial, I.M. et al., "Waldenstrom macroglobulinaemia", Lancet Oncology, vol. 4, pp. 679-685 (2003).
Kuhne, M.R. et al., "BMS-936564/MDX-1338: A Fully Human Anti-CXCR4 Antibody Induces Apoptosis In Vitro and Shows Antitumor Activity In Vivo in Hematologic Malignancies", Clinical Cancer Research, vol. 19, No. 2, pp. 357-366 (2013).

(Continued)

*Primary Examiner* — Zachary C Howard
(74) *Attorney, Agent, or Firm* — Ashton J. Delauney

(57) ABSTRACT

The present disclosure provides a method for treating a subject afflicted with Waldenström's macroglobulinemia (WM) comprising administering to the subject a therapeutically effective amount of an antibody or an antigen-binding portion thereof that specifically binds to a CXCR4 receptor expressed on the surface of a WM cell. The disclosure also provides a therapeutic regimen for treating a patient afflicted with C1013G/CXCR4-associated WM.

23 Claims, 52 Drawing Sheets
Specification includes a Sequence Listing.

(56) References Cited

OTHER PUBLICATIONS

Leleu, X. et al., "Targeting NF-κB in Waldenstrom macroglobulinemia", Blood, vol. 111, No. 10, pp. 5068-5077 (2008).

Ngo, H.T. et al., "SDF-1/CXCR4 and VLA-4 interaction regulates homing in Waldenstrom macroglobulinemia", Blood, vol. 112, pp. 150-158 (2008).

Roccaro, A.M. et al., "Dual targeting of the proteasome regulates survival and homing in Waldenström macroglobulinemia", Blood, vol. 111, pp. 4752-4763 (2008).

Roccaro, A.M. et al., "microRNA expression in the biology, prognosis, and therapy of Waldenström macroglobulinemia", Blood, vol. 113, No. 18, pp. 4391-4402 (2009).

Roccaro, A.M. et al., "Dual targeting of the PI3K/Akt/mTOR pathway as an antitumor strategy in Waldenstrom macroglobulinemia", Blood, vol. 115, No. 3, pp. 559-569 (2010).

Roccaro, A.M. et al., "BM mesenchymal stromal cell-derived exosomes facilitate multiple myeloma progression", Journal of Clinical Investigation, vol. 123, No. 4, pp. 1542-1555 (2013).

Roccaro, A.M. et al., "C1013G/CXCR4 acts as a driver mutation of tumor progression and modulator of drug resistance in lymphoplasmacytic lymphoma", Blood, vol. 123, No. 26, pp. 4120-4131 (2014).

Sacco, A. et al., "Carfilzomib-Dependent Selective Inhibition of The Chymotrypsin-like Activity of the Proteasome Leads to Antitumor Activity in Waldenstrom's Macroglobulinemia", Clinical Cancer Research, vol. 17, No. 7, pp. 1753-1764 (2011).

Taniuchi, S. et al., "The role of a mutation of the CXCR4 gene in WHIM syndrome", Haematologica, vol. 90, pp. 1271-1272 (2005).

Treon, S.P., "How I treat Waldenström macroglobulinemia", Blood, vol. 114, No. 12, pp. 2375-2385 (2009).

Treon, S.P. et al., "Primary Therapy of Waldenström Macroglobulinemia With Bortezomib, Dexamethasone, and Rituximab: WMCTG Clinical Trial 05-180", Journal of Clinical Oncology, vol. 27, No. 23, pp. 3830-3835 (2009).

Treon, S.P. et al., "MYD88 L265P Somatic Mutation in Waldenström's Macroglobulinemia", New England Journal of Medicine, vol. 367, No. 9, pp. 826-833 (2012).

Treon, S.P. et al., "A Prospective Multicenter Study of The Bruton's Tyrosine Kinase Inhibitor Ibrutinib In Patients With Relapsed or Refractory Waldenstrom's Macroglobulinemia", Abstract No. 251, Blood, vol. 122, No. 21 (2013).

Treon, S.P. et al., "Somatic mutations in MYD88 and CXCR4 are determinants of clinical presentation and overall survival in Waldenström macroglobulinemia", Blood, vol. 123, No. 18, pp. 2791-2796 (2014).

Vijay, A. and Gertz, M.A., "Waldenström macroglobulinemia", Blood, vol. 109, No. 12, pp. 5096-5103 (2007).

Yang, G. et al., "A mutation in MYD88 (L265P) supports the survival of lymphoplasmacytic cells in activation of Bruton tyrosine kinase in Waldenström macroglobulinemia", Blood, vol. 122, No. 7, p. 1222-1232 (2013).

Zeng, Z. et al., "Targeting the leukemia microenvironment by CXCR4 inhibition overcomes resistance to kinase inhibitors and chemotherapy in AML", Blood, vol. 113, No. 24, pp. 6215-6224 (2009).

Hunter, Z. et al., "Recurring Activation Mutations and Somatic Deletions Revealed Through Whole Genome Sequencing in Waldenström's Macroglobulinemia", Hematol. Oncol., Suppl. 1, p. 127, Abstract 93, Jun. 2013.

Treon, S. et al., "A Prospective, Multicentre, Phase II Study of the Bruton's Tyrosine Kinase Inhibitor Ibrutinib in Patients With Relapsed and Refractory Waldenstrom's Macroglobulinemia", Hematol. Oncol., Suppl. 1, p. 119, Abstract 67, Jun. 2013.

Treon, S. et al., "Prospective Phase II Clinical Trial of Carfilzomib, Rituximab and Dexamethasone (CARD) in Waldenstrom's Macroglobulinemia (WM)", Hematol. Oncol., Suppl. 1, p. 146, Abstract 150, Jun. 2013.

Cao, Y. et al., "Whole Genome Sequencing Identifies Recurring Somatic Mutations in the C-Terminal Domain of CXCR4, Including a Gain of Function Mutation in Waldenstrom's Macroglobinemia." Blood, Abstract 2715 from 54th ASH Annual Meeting, Nov. 2012.

* cited by examiner

FIG. 1A

```
Anti-CXCR4 Fab BMS-936564/F7/MDX-1338 VH

V segment:      3-48
D segment:      4-23
J segment:      JH6b

Q   V   Q   L   V   Q   S   G   G   G   L   V   Q   P   G   G   S   L
   1  CAG GTG CAG CTG GTG CAG TCT GGG GGA GGC TTG GTA CAG CCT GGG GGG TCC CTG

CDR1
                                                       ~~~~~~~~~~~~~~~~~~~~~~~
       R   L   S   C   A   A   A   G   F   T   F   S   S   Y   S   M   N   W
  55  AGA CTC TCC TGT GCA GCC GCT GGA TTC ACC TTC AGT AGC TAT AGC ATG AAC TGG

CDR2
                                                           ~~~~~~~~~~~~~~~~~~~
       V   R   Q   A   P   G   K   G   L   E   W   V   S   Y   I   S   S   R
 109  GTC CGC CAG GCT CCA GGG AAG GGG CTG GAG TGG GTT TCA TAC ATT AGT AGT AGA

CDR2
      ~~~~~~~~~~~~~~~~~~~~~~~~~~~~~~~~~~~~~~~~~~~~~~~~
       S   R   T   I   Y   Y   A   D   S   V   K   G   R   F   T   I   S   R
 163  AGT AGA ACC ATA TAC TAC GCA GAC TCT GTG AAG GGC CGA TTC ACC ATC TCC AGA

D   N   A   K   N   S   L   Y   L   Q   M   N   S   L   R   D   E   D
 217  GAC AAT GCC AAG AAC TCA CTG TAT CTG CAA ATG AAC AGC CTG AGA GAC GAG GAC

CDR3
                                       ~~~~~~~~~~~~~~~~~~~~~~~~~~~~~~~~~~~~~
       T   A   V   Y   Y   C   A   R   D   Y   G   G   Q   P   P   Y   Y   Y
 271  ACG GCT GTG TAT TAC TGT GCG AGA GAT TAC GGT GGT CAA CCC CCT TAC TAC TAC

CDR3
      ~~~~~~~~~~~~~~~~~~~~~~~~~~
       Y   Y   G   M   D   V   W   G   Q   G   T   T   V   T   V   S   S
 325  TAC TAC GGT ATG GAC GTC TGG GGC CAA GGG ACC ACG GTC ACC GTC TCC TCA
```

FIG. 1B

```
Anti-CXCR4 Fab BMS-936564/F7/MDX-1338 VK

V segment:      L15
J segment:      JK1

A   I   R   M   T   Q   S   P   S   S   L   S   A   S   V   G   D   R
  1  GCC ATC CGG ATG ACC CAG TCT CCA TCC TCA CTG TCT GCA TCT GTA GGA GAC AGA

CDR1
                                    ~~~~~~~~~~~~~~~~~~~~~~~~~~~~~~~~~~~~~~~~
      V   T   I   T   C   R   A   S   Q   G   I   S   S   W   L   A   W   Y
 55  GTC ACC ATC ACT TGT CGG GCG AGT CAG GGT ATT AGC AGC TGG TTA GCC TGG TAT

CDR2
                                                            ~~~~~~~~~~~~~~~~
      Q   Q   K   P   E   K   A   P   K   S   L   I   Y   A   A   S   S   L
109  CAG CAG AAA CCA GAG AAA GCC CCT AAG TCC CTG ATC TAT GCT GCA TCC AGT TTG

CDR2
     ~~~~~~~~
      Q   S   G   V   P   S   R   F   S   G   S   G   S   G   T   D   F   T
163  CAA AGT GGG GTC CCA TCA AGG TTC AGC GGC AGT GGA TCT GGG ACA GAT TTC ACT

CDR3
                                                                ~~~~~~~~
      L   T   I   S   S   L   Q   P   E   D   F   V   T   Y   Y   C   Q   Q
217  CTC ACC ATC AGC AGC CTG CAG CCT GAA GAT TTT GTA ACT TAT TAC TGC CAA CAG

CDR3
     ~~~~~~~~~~~~~~~~~~~~~~~~~~~~
      Y   N   S   Y   P   R   T   F   G   Q   G   T   K   V   E   I   K
271  TAT AAT AGT TAC CCT CGG ACG TTC GGC CAA GGG ACC AAG GTG GAA ATC AAA
```

FIG. 5A-C
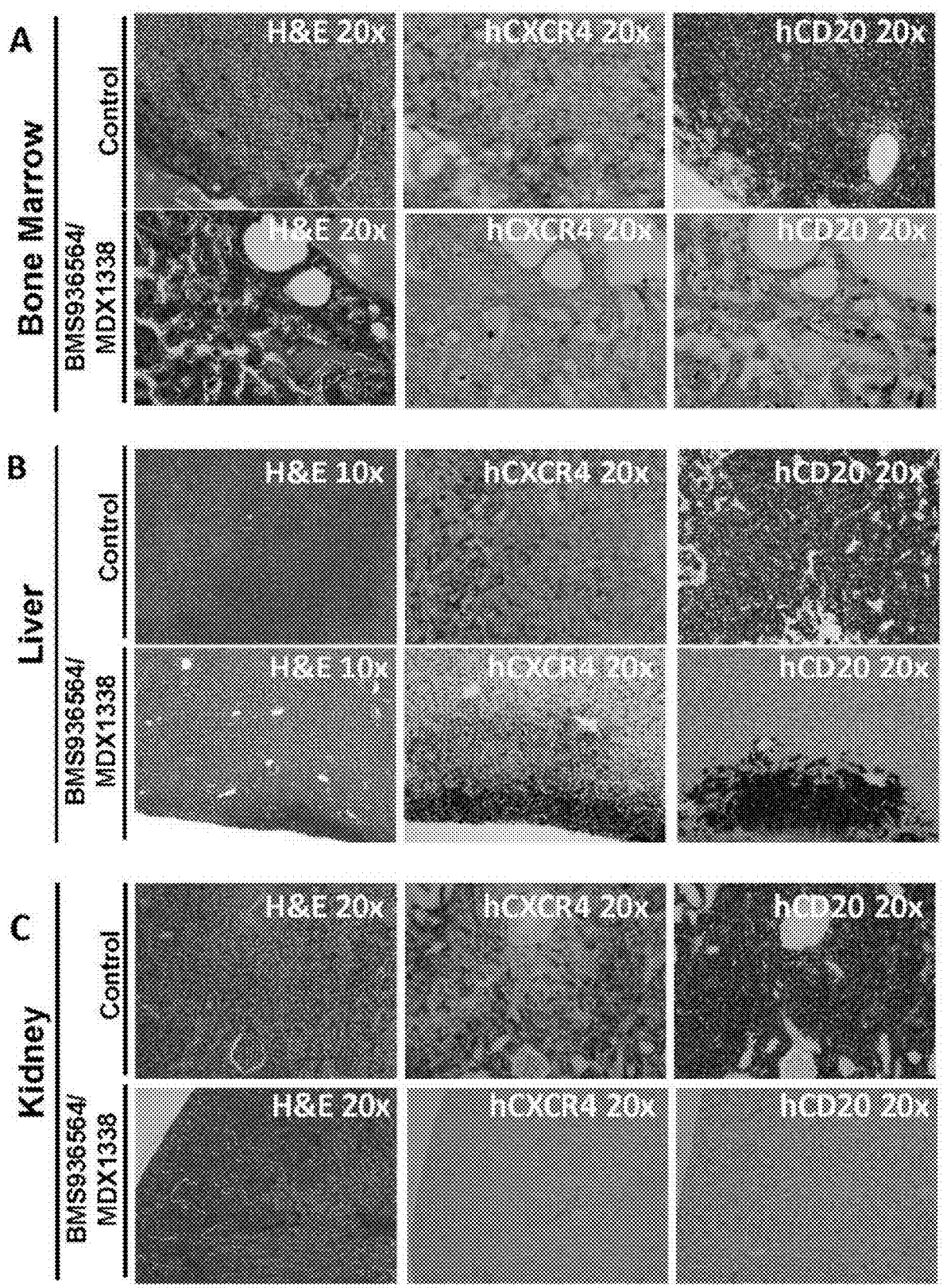

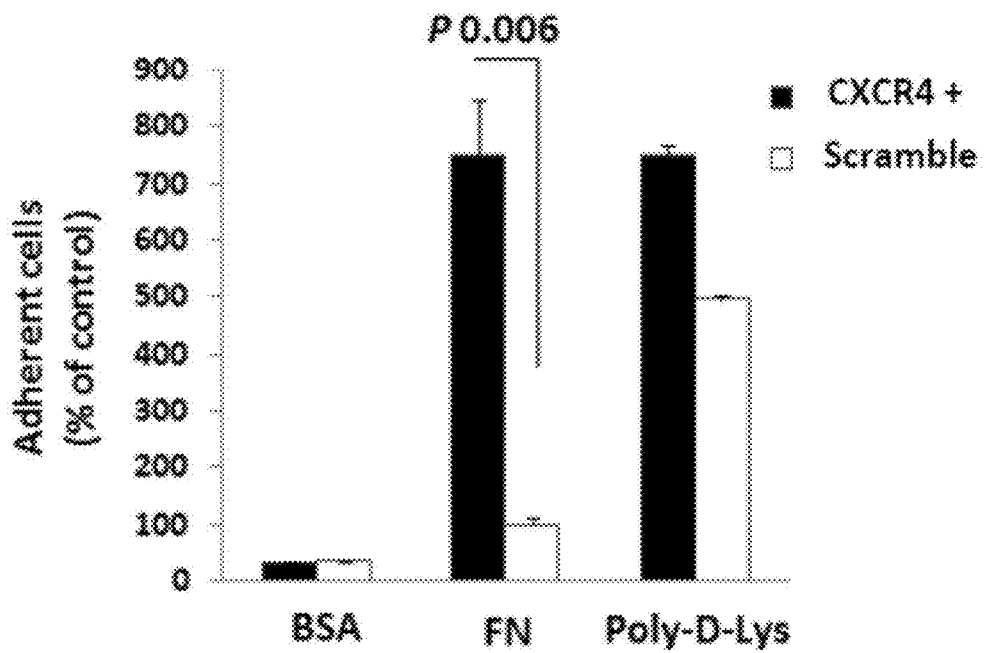
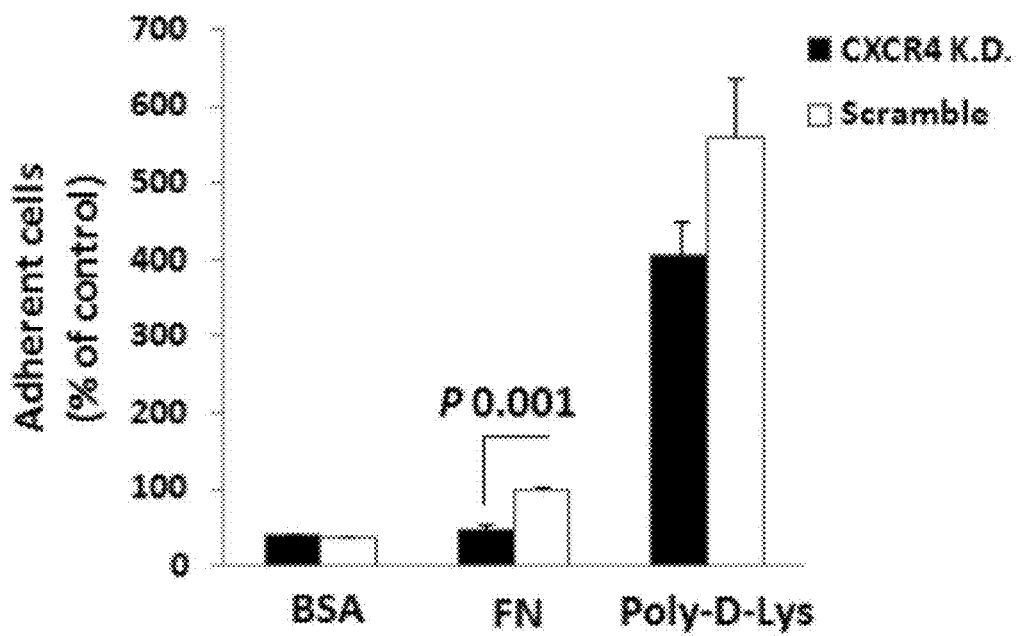

FIG. 9A-E
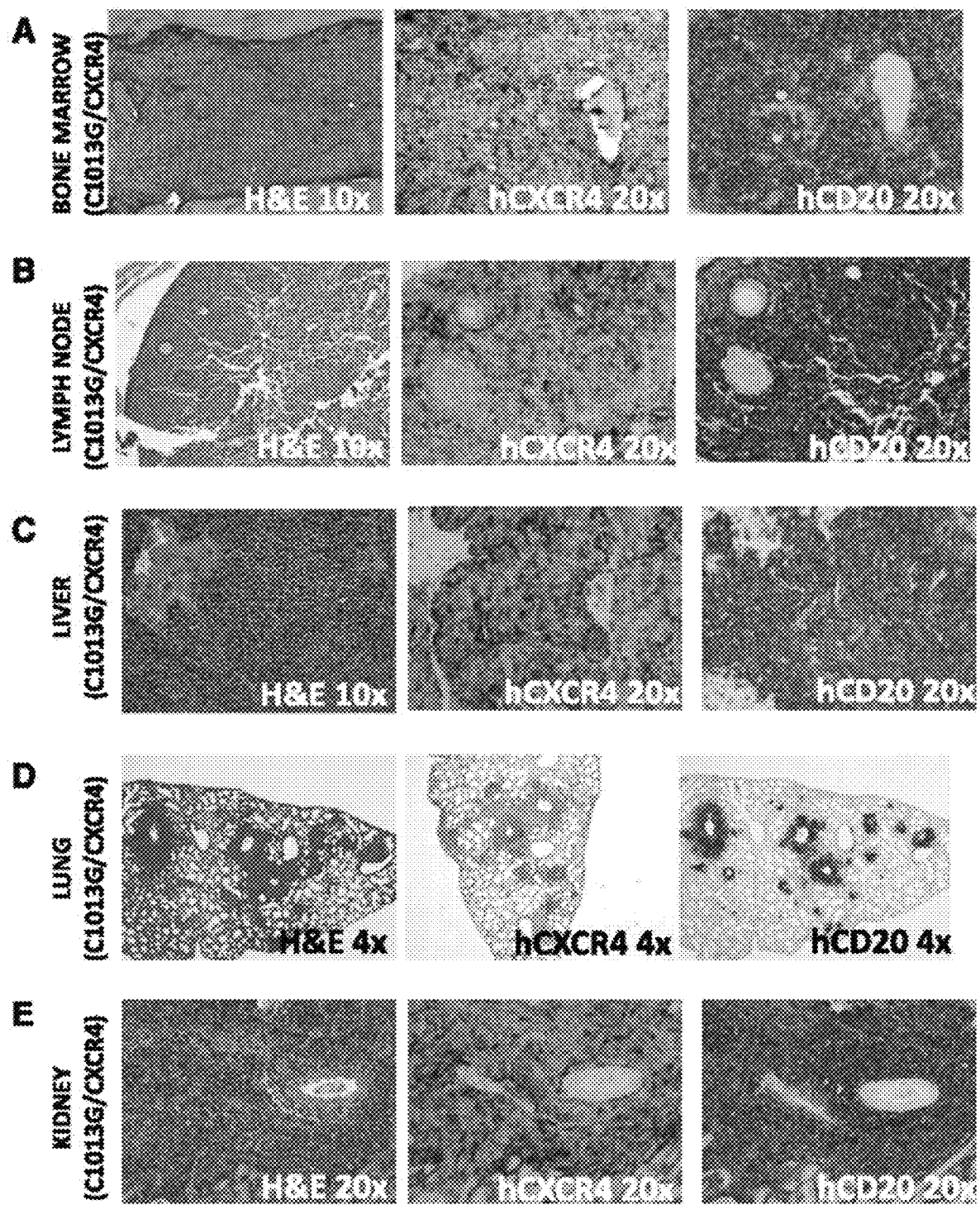

TREATMENT OF C1013G/CXCR4-ASSOCIATED WALDENSTROM'S MACROGLOBULINEMIA WITH AN ANTI-CXCR4 ANTIBODY

Throughout this application, various publications are referenced in parentheses by author name and date, or by patent No. or Publication No. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein. However, the citation of a reference herein should not be construed as an acknowledgement that such reference is prior art to the present invention.

FIELD OF THE INVENTION

The present disclosure relates to the use of monoclonal antibodies that bind specifically to human CXCR4 in methods of treating C1013G/CXCR4-associated Waldenström's macroglobulinemia.

BACKGROUND OF THE INVENTION

The C-X-C chemokine receptor type 4 (CXCR4) plays a crucial role in physiological conditions, such as lymphopoiesis and bone marrow (BM) myelopoiesis, during embryogenesis. In postnatal life, CXCR4 and its ligand modulate homing of CD341 cells to the BM niches as well as lymphocytic trafficking. CXCR4 has been shown to be mutated in patients with an inherited heterozygous autosomal dominant disease characterized by aberrantly functioning immunity, known as warts, hypogammaglobulinemia, infections, and myelokathexis (WHIM) syndrome, because of the presence, among others, of an activating mutation of the CXCR4 gene, represented by the C1013G variant (Balabanian et al., 2005; Balabanian et al., 2008). Recent evidence supports the presence of CXCR4 somatic aberrations in Waldenström's macroglobulinemia (WM; lymphoplasmacytic lymphoma) (Hunter et al., 2014; Treon et al., 2014). The functional role of this variant in supporting progression of lymphoplasmacytic lymphoma and whether it is peculiar for WM or it occurs at an IgM monoclonal gammopathy of undetermined significance (MGUS) stage compared with other B-cell lymphoproliferative entities has not been previously described.

WM is a rare B-cell disorder with an incidence rate of about 3 cases per million people per year in the United States. About 1,000 to 1,500 people are diagnosed with WM each year in the U.S. Whole-genome sequencing has recently shed light on the molecular mechanisms that may contribute to the pathogenesis of this disease. Specifically, L265P/MYD88 has been described as a prevalent somatic mutation in WM patients (Treon et al., 2012). In vitro studies have demonstrated that the L265P/MYD88 variant may lead to increased tumor cell proliferation (Yang et al., 2013); this may be explained, at least in part, by MYD88-dependent activation of nuclear factor κB (NF-κB), a known signaling pathway that modulates tumor B-cell survival, growth, and resistance to therapy (Leleu et al., 2008). These observations are also consistent with previous findings that over-expression of the oncogenic microRNA-155 in clonal WM cells leads to activation of NF-κB in primary WM cells. Indeed, microRNA-155 loss-of-function studies led to inhibition of NF-κB and reduction of tumor growth in vitro and in vivo (Leleu et al., 2008; Roccaro et all, 2009). However, the MYD88 mutation did not predict progression or resistance to therapy in several published studies, indicating that other genetic alterations may be critical for tumor progression and dissemination to distant organs.

Among low-grade B-cell lymphomas, WM represents a lymphoplasmacytic subtype characterized by BM infiltration of lymphoplasmacytic cells and secretion of a serum monoclonal immunoglobulin M (IgM) protein that can lead to complications of hyperviscosity, bleeding and peripheral neuropathy (Ghobrial et al., 2003; Vijay and Gertz, 2007). The evidence for widespread involvement of the BM at the time of diagnosis implies cell trafficking of clonal B-cells into the BM. In this context, one of the main regulators of tumor B-cell homing to the BM is represented by CXCR4 through the interaction with its related ligand stromal derived factor-1 (SDF-1/CXCL12).

A preliminary report of whole genome sequencing has indicated that CXCR4 may be mutated in 29% (16/55) of patients with WM (Cao et al., 2012). The presence and role of the C1013/CXCR4 variant was therefore investigated in patients with WM and different B-cell lymphoproliferative disorders, aimed at defining the in vivo functional role of this variant in WM as well as the response of C1013G/CXCR4-associated WM patients to treatment with an anti-CXCR4 antibody.

Anti-CXCR4 monoclonal antibodies that exhibit therapeutic efficacy in treating cancer have previously been described in PCT Publication Nos. WO 2008/060367 and WO 2013/071068. The disclosures of both these applications are hereby incorporated in their entireties by reference into this application. A fully human monoclonal antibody, ulocuplumab (designated F7 in WO 2008/060367, and also previously designated BMS-936564 or MDX-1338, all four designations being used interchangeably herein), exhibited unexpectedly advantageous anti-tumor properties in pre-clinical studies with both solid tumors and hematologic cancers. Ulocuplumab is also currently undergoing Phase I clinical studies in patients with relapsed/refractory B-cell malignancies (NCT01120457; see Clinical Trials Website, http://www.clinicaltrials.gov).

SUMMARY OF THE INVENTION

The present disclosure provides method for treating a subject afflicted with C1013G/CXCR4-associated Waldenström's macroglobulinemia comprising administering to the subject a therapeutically effective amount of an antibody or an antigen-binding portion thereof that specifically binds to a CXCR4 receptor expressed on the surface of a WM cell. In preferred embodiments, the subject is a human and the antibody or antigen-binding portion thereof binds to a human CXCR4 receptor expressed on a cell surface, preferably a human CXCR4 carrying the C1013G mutation. In certain embodiments, the antibody or antigen-binding portion thereof is a chimeric, humanized or human antibody or an antigen-binding portion thereof. Preferably, the antibody or antigen-binding portion thereof is a human antibody or an antigen-binding portion thereof.

This disclosure also provides a method for treatment of a subject afflicted with C1013G/CXCR4-associated WM, which method comprises: (a) selecting a subject that is a suitable candidate for treatment, the selecting comprising: (i) optionally providing a test tissue sample obtained from WM tissue in the subject; (ii) performing an assay to determine whether cells in the WM test tissue sample carry the C1013G mutation in the CXCR4 gene; and (iii) selecting the subject as a suitable candidate based on a determination that the WM cells carry the C1013G mutation in the CXCR4 gene; and (b) administering to the selected subject a therapeutically effective amount of an antibody or an antigen-binding portion thereof that specifically binds to a CXCR4 receptor expressed on the surface of a C1013G/CXCR4-associated WM cell.

The disclosure further provides a method for treatment of a subject afflicted with C1013G/CXCR4-associated WM, which method comprises administering to the subject a therapeutically effective amount of an antibody or an antigen-binding portion thereof that specifically binds to a CXCR4 receptor expressed on the surface of a C1013G/CXCR4-associated WM cell, the subject having been selected on the basis that the WM cells of the subject are determined to carry the C1013G mutation in the CXCR4 gene.

The disclosure also provides a method for selecting a WM patient for treatment with an antibody or an antigen-binding portion thereof that specifically binds to a CXCR4 receptor expressed on the surface of a WM cell, which method comprises: (a) providing a test tissue sample obtained from WM tissue in the patient; (b) performing an assay to determine whether cells in the WM test tissue sample carry the C1013G mutation in the CXCR4 gene; and (c) selecting the patient for treatment based on a determination that the WM cells carry the C1013G mutation in the CXCR4 gene.

In addition, this disclosure provides a method for determining a therapeutic regimen comprising an anti-CXCR4 antibody or an antigen-binding portion thereof for treating C1013G/CXCR4-associated WM in a subject, which method comprises: (a) providing a test tissue sample obtained from WM tissue in the subject; (b) performing an assay to determine whether cells in the WM test tissue sample carry the C1013G mutation in the CXCR4 gene; and (c) determining a therapeutic regimen comprising an anti-CXCR4 antibody or antigen-binding portion thereof based on the determination that the WM cells carry the C1013G mutation in the CXCR4 gene. In one aspect, the disclosure also provides a therapeutic regimen for treating a patient afflicted with C1013G/CXCR4-associated WM, which regimen is determined by the present method.

In certain embodiments of any of the above methods, C1013G/CXCR4-mutated cells in the WM patient exhibit resistance to conventionally used anti-WM agents, including mammalian target of rapamycin (mTOR), Bruton's tyrosine kinase (BTK), and/or phosphatidylinositol 3-kinase (PI3K) inhibitors. In certain preferred embodiments, C1013G/CXCR4-mutated cells are resistant to the BTK inhibitor, ibrutinib (IMBRUVICA®). Accordingly, in certain embodiments, a therapeutically effective amount of an anti-CXCR4 antibody or antigen-binding portion thereof is administered to a subject afflicted with C1013G/CXCR4-associated WM after the subject has failed treatment with a mTOR, BTK and/or PI3K inhibitor, preferably after failure of treatment with ibrutinib. In other embodiments, the subject is treated with a combination of a therapeutically effective amount of an anti-CXCR4 antibody or antigen-binding portion thereof and a therapeutically effective amount of a mTOR, BTK or PI3K inhibitor. In certain preferred embodiments, the subject is treated with a combination of the anti-CXCR4 antibody, ulocuplumab, and a therapeutically effective amount of the BTK inhibitor, ibrutinib.

In certain embodiments of any of the above methods, the anti-CXCR4 antibody or antigen-binding portion thereof comprises the CDR1, CDR2 and CDR3 domains in a heavy chain variable region comprising consecutively linked amino acids, the sequence of which is set forth in SEQ ID NO: 25, and the CDR1, CDR2 and CDR3 domains in a light chain variable region comprising consecutively linked amino acids, the sequence of which is set forth in SEQ ID NO: 29.

In other embodiments, the anti-CXCR4 antibody or antigen-binding portion thereof comprises a heavy chain variable region comprising consecutively linked amino acids, the sequence of which is set forth in SEQ ID NO: 25, and a light chain variable region comprising consecutively linked amino acids, the sequence of which is set forth in SEQ ID NO: 29.

In further embodiments, the anti-CXCR4 antibody or antigen-binding portion thereof comprises a heavy chain variable region CDR1 comprising consecutively linked amino acids having the sequence set forth in SEQ ID NO: 1, a heavy chain variable region CDR2 comprising consecutively linked amino acids having the sequence set forth in SEQ ID NO: 5, a heavy chain variable region CDR3 comprising consecutively linked amino acids having the sequence set forth in SEQ ID NO: 9, a light chain variable region CDR1 comprising consecutively linked amino acids having the sequence set forth in SEQ ID NO: 13, a light chain variable region CDR2 comprising consecutively linked amino acids having the sequence set forth in SEQ ID NO: 17, and a light chain variable region CDR3 comprising consecutively linked amino acids having the sequence set forth in SEQ ID NO: 21. In preferred embodiments, the antibody is ulocuplumab.

In another aspect, the disclosure provides a kit for treating C1013G/CXCR4-associated WM in a subject, the kit comprising: (a) a dose of an anti-CXCR4 antibody or an antigen-binding portion thereof; and (b) instructions for using the anti-CXCR4 antibody in any one of the above methods. Exemplary anti-CXCR4 antibodies for use in the kit include human monoclonal antibodies F7 (ulocuplumab), F9, and D1, described in WO 2008/060367. In preferred embodiments, the anti-CXCR4 antibody in the kit is ulocuplumab.

Other features and advantages of the instant disclosure will be apparent from the following detailed description and examples, which should not be construed as limiting. The contents of all references, GENBANK® entries, patents and published patent applications cited throughout this application are expressly incorporated herein by reference.

BRIEF DESCRIPTION OF THE FIGURES

FIGS. 1A and 1B: FIG. 1A shows the nucleotide sequence (SEQ ID NO: 33) and amino acid sequence (SEQ ID NO: 25) of the heavy chain variable region of the F7 (ulocuplumab) human monoclonal antibody. The heavy chain CDR1 (SEQ ID NO: 1), CDR2 (SEQ ID NO: 5) and CDR3 (SEQ ID NO: 9) regions are delineated and the V, D and J germline derivations are indicated. FIG. 1B shows the nucleotide sequence (SEQ ID NO: 37) and amino acid sequence (SEQ ID NO: 29) of the light chain variable region of F7. The light chain CDR1 (SEQ ID NO: 13), CDR2 (SEQ ID NO: 17) and CDR3 (SEQ ID NO: 21) regions are delineated and the V and J germline derivations are indicated.

FIG. 2A shows that primary WM samples harboring the C1013G/CXCR4 variant present with higher CXCR4 surface expression compared with wild-type (WT) primary WM samples, as measured by flow cytometry on CD191 BM-derived WM cells shown in FIG. 2B.

FIGS. 4A-H show the enhanced capability of CXCR4-over-expressing WM cells to disseminate in vivo. BCWM.1 cells were infected with either precision LentiORF/CXCR4/GFP (CXCR4$^+$) or an empty vector/RFP (control) and injected intravenously into SCID/Bg mice (n=5/group). After 3 weeks, mice were euthanized and organs harvested. Hematoxylin-eosin immunohistochemical staining for human CD20 and human CXCR4 were performed on femur BM (FIGS. 4A and 4B), liver (FIGS. 4C and 4D) and kidney (FIGS. 4E and 4F). Quantification of CD20 and CXCR4 staining was performed showing a higher number of CXCR4/CD20+ cells in CXCR4+ cell-injected mice compared to control cell-injected mice. P indicates P value. Mice were euthanized and serum collected at the third week, and human IgM levels were tested by ELISA (FIG. 4G). Detection of human CXCR4 level was performed by qRT-PCR (ΔΔCt method) on cells isolated ex vivo from the BM femurs and un-injected mice (n=3) and pooled control cell-injected mice (n=4) were used as controls (FIG. 4H). P indicates P value. Bars indicate standard deviation.

FIGS. 5A-5F: FIGS. 5A-5F show that over-expression of CXCR4 in WM cells leads to reduced survival, and enhanced adhesion properties and growth in vitro. CXCR4 over-expressing cells (CXCR4$^+$) presented with a more aggressive ability to disseminate to BM (FIG. 5A), liver (FIG. 5B) and kidneys (FIG. 5C) compared to the related empty vector-infected cells (Hematoxylin Eosin ×10, antibody staining ×20 and ×10, magnifications). Quantification of human CD20 and CXCR4 staining is shown in FIGS. 4A-4F. FIG. 5D depicts a Kaplan-Meier curve showing decreased survival in CXCR4$^+$ cell-injected mice vs. empty vector cell-injected mice (n=7/group). P indicates P value (Log-rank test). FIGS. 5E and 5F show that CXCR4 over-expression led to increased WM cell adhesion to primary bone marrow mesenchymal stromal cells (BM-MSCs), and increased cell proliferation when compared to CXCR4-silenced WM cells (CXCR4-K.D.) in which reduced adhesion to BM-MSCs and reduced cell proliferation were observed. Bars indicate standard deviation. DAPI, 4′,6-diamidino-2-phenylindole; NS, not significant.

FIGS. 7A and 7B: FIGS. 7A and 7B show the effect of CXCR4 loss- and gain-of-function on WM cell adhesion properties. BCWM.1 cells were stably infected with either LentiORF/CXCR4 (CXCR4$^+$) (FIG. 7A) or CXCR4 shRNA (CXCR4 K.D.) (FIG. 7B), and respective scramble probes. Adhesion was tested using BSA- (negative control), poly-D-Lysine- (positive control), and fibronectin-coated wells. Bars indicated standard deviation.

FIGS. 8A-8E show the efficiency of induced mutagenesis in infected WM cells and the lack of brain involvement in mice injected with C1013G/CXCR4-mutated WM cells. Genomic DNA (gDNA; FIG. 8A) and cDNA (FIG. 8B) were isolated from infected BCWM.1 cells. Empty/control vector-infected cells were used as control (control cells). Detection of the C1013G allele was evaluated by using allele-specific PCR. P indicates P value. Bars indicate standard deviation. Detection of the C1013G mutation was valuated using Sanger Sequencing (FIG. 8C). SCID/Bg mice were injected intravenously with either C1013G/CXCR4 mutation-harboring BCWM.1 cells or control cells (FIG. 8D). Hematoxylin-eosin immunohistochemical staining (H.E.) for human CD20 and human CXCR4 was performed on brain, showing the absence of tumor cell infiltration (FIG. 8E). (4× magnifications are provided).

FIGS. 9A-9F: FIGS. 9A-9F show the effect of the CXCR4/C1013G mutation on dissemination and survival of WM cells in vivo. WM cells harboring the C1013G/CXCR4 variant present with changes at the mRNA level, together with increased cell adhesion and cell proliferation. SCID/Bg mice injected intravenously with C1013G/CXCR4-variant harboring WM cells presented with significant involvement of BM (FIG. 9A), lymph nodes (FIG. 9B), liver (FIG. 9C), lung (FIG. 9D), and kidneys (FIG. 9E) (×4, ×10 and 20× magnifications). Quantification of human CD20 and CXCR4 staining is shown in FIGS. 10A-10H. A Kaplan-Meier curve (FIG. 9F) shows decreased survival in C1013G/CXCR4 cell-injected mice (leftward plot) vs. control vector cell-injected mice (rightward plot) (n=7/group). Death for control vector cell-injected mice was observed at days 37, 48, and 62. P indicates P value (Log-rank test).

FIGS. 10A-10H show the quantification of human CD20 and CXCR4 expression in tissues harvested from mice injected with C1013G/CXCR4-mutated WM cells. SCID/Bg mice were injected intravenously with either C1013G/CXCR4 variant-harboring BCWM.1 cells or empty/control vector-infected cells (control cells). After 3 weeks mice were euthanized and organs harvested. Hematoxylin-eosin immunohistochemical staining for human CD20 and human CXCR4 were performed on femur BM (FIGS. 10A and 10B), liver (FIGS. 10C and 10D), kidney (FIGS. 10E and 10F), lymph nodes (FIG. 10G), and lung (FIG. 10H) (Nikon, Melville, N.Y.). Quantification of CD20 and CXCR4 staining was performed (NIS Elements software, Nikon, Melville, N.Y.). P indicates P values. A T-test was used to analyze femur, liver, kidney and lung, and an Anova-test was used to analyze lymph nodes.

FIGS. 11A-11D show the effect of the CXCR4/C1013G mutation on adhesion and proliferation of WM cells in vivo. In SCID/Bg mice injected intravenously with C1013G/CXCR4-WM cells, the C1013G/CXCR4 variant increased adhesion (FIG. 11A) and proliferation (FIG. 11B) of WM cells either alone or in the context of BM-MSCs. The C1013G/CXCR4 variant increased adhesion (FIG. 11C) and proliferation (FIG. 11D) of MWCL1 cells either alone or in the context of BM-MSCs. Empty/control vector-infected cells were used as control. Bars indicate standard deviation. P indicates P values.

FIGS. 12A-12M show that C1013G CXCR4-mutated cells differ from control cells at the gene level. FIGS. 12A-12L show Gene Set Enrichment Analysis (GSEA) enrichment plots of tumor invasiveness, cell proliferation, antiapoptosis and oncogenic signature genes in C1013G/CXCR4 mutated cells versus control vector-infected cells (control cells). The plotted curves show the enrichment score and reflect the degree to which each gene (vertical lines) is represented at the top or bottom of the ranked gene list. The heat map indicates the relative abundance (left to right) of the genes specifically enriched in the mutated cells and compared to the control cells. All the gene sets were enriched in C1013G/CXCR4 mutated cells, with a false discovery rate (FDR) always <0.25. Normalized enrichments score (NES) and FDR are shown per each gene set analyzed. FIG. 12M shows a GSEA enrichment plot for the upregulated genes listed in Table 3, in C1013G/CXCR4-mutated cells vs. control vector-infected cells (control cells). The same genes were enriched in mutated cells as compared to control cells.

FIGS. 13A-13G show that WM cells harboring the C1013G/CXCR4 somatic variant present with drug resistance. FIGS. 13A and 13B show GSEA enrichment plots of multiple drug resistance and response to drug signature genes in C1013G/CXCR4-mutated cells and control vector-infected cells (control cells), respectively. The plotted curves show the enrichment score and reflect the degree to which each gene (vertical lines) is represented at the top or bottom of the ranked gene list. The heat map indicates the relative abundance (left to right) of the genes specifically enriched in the mutated cells as compared with the control cells. Gene sets were considered enriched with a FDR always <0.25. Normalized enrichments score (NES) and FDR are shown per each gene set analyzed. FIGS. 13C-13G show the effects on C1013G/CXCR4-WM cell lines (BCWM1; MWCL1) or control vector-infected cells (control) exposed to everolimus, ibrutinib, idelalisib, bortezomib, and carfilzomib for 48 h. Cytotoxicity was determined by 3-(4,5-dimethylthiazol-2-yl)-2,5-diphenyltetrazolium bromide.

FIGS. 14A and 14B show the effect of BMS-936564 on migration of WM cells in vitro. WM cell lines (BCWM.1; MWCL.1) were tested for their migratory properties using a transwell migration assay. Cells were exposed to increasing concentrations of BMS-936564 and migration was determined after 5 h. The transwell migration assay was performed in presence of either primary WM BM-MSCs (FIG. 14A) or in presence of SDF-1α (FIG. 14B). In both cases, BMS-936564-dependent inhibition of WM cell migration was observed.

FIGS. 15A-15C show the effect of BMS-936564 on adhesion and proliferation of WM cells in vitro. WM cell lines were treated with BMS-936564 for 4 h and subsequently tested for adhesion to primary WM BM-MSCs. Evaluation of adhesion after 2 h showed BMS-936564-dependent inhibition of WM cell adhesion (FIG. 15A). WM cell lines, MWCL.1 (FIG. 15B) and BCWN.1 (FIG. 15C) were cultured with control media and with BMS-936564 for 48 h in the presence or absence of primary WM BMMSCs. Cell proliferation was assessed using a [$^3$H]-thymidine uptake assay. Bars indicate standard deviations. P indicates P value. All data represent mean (±sd) of triplicate experiments. The CXCR4 antagonist, AMD3110 (Sigma-Aldrich, St. Louis, Mo.), was used as control.

FIGS. 17A and 17B show that control antibody did not affect adhesion (FIG. 17A) or migration (FIG. 17B) of WM cell lines in vitro.

FIGS. 18A and 18B show the effect of BMS-936564 on apoptosis-related proteins in WM cells. BCWM.1 cells were exposed to BMS-936564 for 14 h. Whole cell lysates were then harvested and subjected to western blot analysis using anti-caspase-9, anti-PARP and anti-tubulin antibodies (FIG. 18A), and anti-p-β catenin, anti-β-catenin, anti-p-GSK3β, and anti-tubulin antibodies (FIG. 18B).

FIGS. 19A-19J show that BMS-936564 targets C1013G/CXCR4-mutated cells in WM cells in vivo. BMS-936564 inhibited dissemination of C1013G/CXCR4-mutated WM cells in vivo. Human CD20 and CXCR4 staining was significantly reduced in tissues explanted from mice treated with BMS-936564 compared to isotype control-treated mice (untreated). P indicates P values.

FIGS. 20A-20E show representative histochemical images of the effect of BMS-936564 on C1013G/CXCR4-mutated cells in WM cells in vivo. SCID/Bg mice were injected intravenously with either C1013G/CXCR4 variant-harboring BCWM.1 cells or empty/control vector-infected cells (control cells). Mice were treated with either BMS-936564 or control antibody (10 mg/kg, intraperitoneally; x3/4/week; mice: 5/group). After 3 weeks mice were euthanized and organs harvested. Hematoxylin-eosin immunohistochemical staining for human CD20 and CXCR4 were performed on femur BM (FIG. 20A), liver (FIG. 20B), kidney (FIG. 20C), lung (FIG. 20D), and lymph nodes (FIG. 20E) (Nikon, Melville, N.Y.; 4×, 10× or 20× magnifications are shown).

FIGS. 21A-21D show BMS-936564 targets C1013G/CXCR4-mutated cells in WM cells in the context of BM. C1013G/CXCR4-infected BCWM.1 cells were tested for their migratory properties using a transwell migration assay. Cells were exposed to increasing concentrations of BMS-936564 and migration was determined after 5 h. The transwell migration assay was performed in presence of either primary WM BM-MSCs (FIG. 21A) or SDF-1α (FIG. 21B). In both cases, BMS-936564-dependent inhibition of WM cell migration was observed. C1013G/CXCR4-infected BCWM.1 cells were treated with BMS-936564/for 4 h and subsequently tested for adhesion to primary WM BM-MSCs. Evaluation of adhesion after 2 h showed BMS-936564-dependent inhibition of WM cell adhesion (FIG. 21C). C1013G/CXCR4-infected BCWM.1 cells were cultured with control media and with BMS-936564 for 48 h in the presence or absence of primary WM BM-MSCs. Cell proliferation was assessed using [$^3$H]-thymidine uptake assay (FIG. 21D). Bars indicate standard deviations. P indicates P value. All data represent mean (±sd) of triplicate experiments. Bars indicated standard deviation.

FIGS. 22A-22C show the effect of BMS-936564 on survival and apoptosis-related signal proteins in C1013G/CXCR4-WM cells. C1013G/CXCR4-mutated cells were cultured in presence or absence of BMS-936564 for 6 h, showing inhibition of phospho(p)-ERK, ERK, p-Akt, Akt, p-Src (FIG. 22A). Similarly, cells were exposed to the compound for 14 h, and induction of apoptosis-related pathways was observed (p-GSK3β, and p-β-catenin (FIG. 22B), and PARP and Caspase-9 (FIG. 22C)).

FIGS. 23A-23F show that BMS-936564 inhibits WM homing in vivo and synergistically enhances WM chemosensitivity to bortezomib in vivo and in vitro. BCWM.1-mCherry$^+$ cells were injected intravenously into SID/Bg mice. Mice were treated with either control antibody or BMS-936564 (10 mg/kg, intraperitoneally; x3/4/week); bortezomib (0.5 mg/kg, intraperitoneally x2/week); or BMS-936564+bortezomib (same dosages as above, x2/week). BM cells were harvested at the end of the study and evaluated using a fluorescence plate reader. Control is intended as number of mCherry$^+$ cells identified from the BM of the control antibody-treated mice (FIG. 23A). Serum was collected at the end of the study. Serum IgM secretion was evaluated using a human IgM ELISA kit (FIG. 23B). WM cell lines (BWM.1; FIGS. 23C and D, and MWCL.1; FIGS. 23E and F) were exposed to BMS-936564 or to bortezomib, used either alone or in a combinatory regimen, for 48 h. Cell toxicity was performed by MTT. Synergism was evaluated by using Calcusyn software: isobologram, combination indices (C.I.) and fractions affected (F.A.) of the combination of BMS-936564 and bortezomib are shown. Bars indicate standard deviation.

DETAILED DESCRIPTION OF THE INVENTION

Figure 2A:
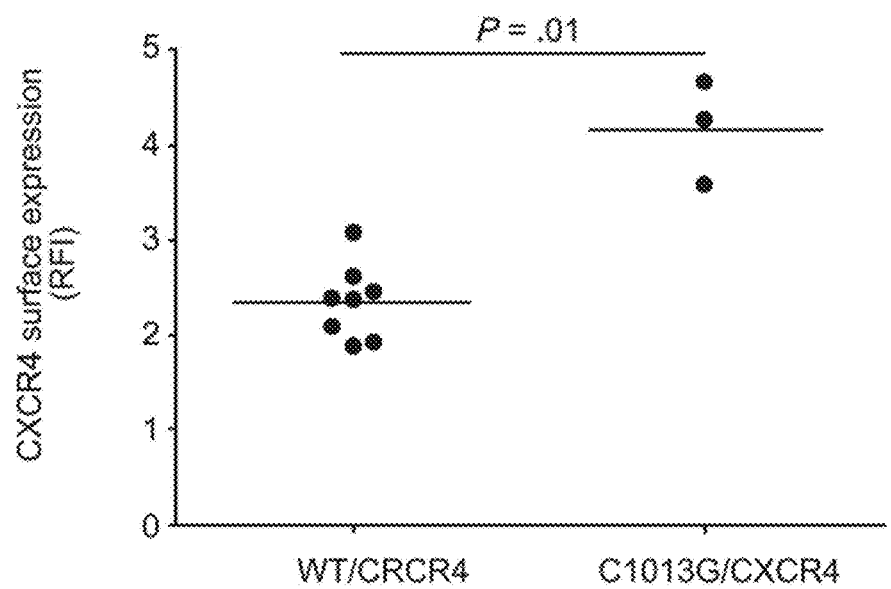
FIGS. 2A and 2B.

The present disclosure relates to methods of using monoclonal antibodies that bind specifically to native human CXCR4 expressed on a cell surface to modulate CXCR4 activity in, or otherwise treat, patients afflicted with Waldenström's macroglobulinemia. These methods are particularly applicable to WM patients that carry an activating C1013G mutation in the CXCR4 gene. In certain embodiments, the anti-CXCR4 antibody is administered as monotherapy or as part of a combination therapy (e.g., in combination with a mTOR, BTK and/or PI3K inhibitor) as a first ("front") line of treatment, e.g., the initial or first treatment. In other embodiments, the anti-CXCR4 antibody is administered as a second- or third-line therapy, e.g., after initial treatment with the same or one or more different therapeutics, including after relapse and/or where the first treatment has failed. Thus, in certain embodiments, the anti-CXCR4 antibody is administered after failure of treatment with another anti-WM agent, for example, a mTOR, BTK and/or PI3K inhibitor.

Definitions

In order that the present disclosure may be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Preferred routes of administration for antibodies of the invention include intravenous, subcutaneous, intramuscular, intraperitoneal, spinal or other parenteral routes of administration, for example, by injection or infusion. The phrase "parenteral administration" as used herein means modes of administration other than enteral and topical administration. Administering can also be performed, for example, once, a plurality of times, and/or over one or more extended periods.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-5}$ to $10^{-11}$ $M^{-1}$ or less. Any $K_D$ greater than about $10^{-4}$ $M^{-1}$ is generally considered to indicate nonspecific binding. As used herein, an antibody that "binds specifically" to an antigen refers to an antibody that binds to the antigen and substantially identical antigens with high affinity, which means having a $K_D$ of about $10^{-7}$ M or less, preferably about $10^{-8}$ M or less, more preferably about $5 \times 10^{-9}$ M or less, even more preferably about $5 \times 10^{-10}$ M or less, and most preferably between about $10^{-9}$ M and about $10^{-11}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99 sequence identity to the sequence of the given antigen. By way of example, an antibody that binds specifically to human CXCR4 may also have cross-reactivity with CXCR4 antigens from certain primate species but may not cross-react with CXCR4 antigens from certain rodent species or with an antigen other than CXCR4, e.g., a human PD-1 antigen.

The immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class (e.g., IgM or IgG1) that is encoded by the heavy chain constant region genes. "Antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man.

Where not expressly stated, and unless the context indicates otherwise, the term "antibody" also includes an antigen-binding portion of any of the aforementioned immunoglobulins. An "antigen-binding portion" or an "antigen-binding fragment" of an antibody refers to one or more fragments of an antibody that retain the ability to bind specifically to the antigen bound by the whole antibody. Examples of binding fragments encompassed within the term "antigen-binding portion" of an antibody include a Fab, F(ab')₂ Fd, Fv, and single chain variable fragment (scFv), a divalent or bivalent scFv, a diabody or other antibody multimer (e.g., a trivalent triabody or tetravalent tetrabody), a minibody, and even an isolated CDR, which may exhibit antigen-binding function. All of the above proteolytic and engineered fragments of antibodies and related variants (see Hollinger et al., 2005; Olafsen et al., 2010, for further details) are encompassed within the term "antigen-binding portion" of an antibody.

The term "monoclonal antibody" ("mAb") refers to a preparation of antibody molecules of single molecular composition, i.e., antibody molecules whose primary sequences are essentially identical, and which exhibits a single binding specificity and affinity for a particular epitope. Monoclonal antibodies may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream. Cancers include solid tumors and hematological malignancies.

A solid tumor is a neoplasm (new growth of cells) or lesion (damage of anatomic structures or disturbance of physiological functions) formed by an abnormal growth of body tissue cells other than blood, BM or lymphatic cells. It consists of an abnormal mass of cells, which may stem from different tissue types such as liver, colon, breast, or lung, and which initially grows in the organ of its cellular origin. However, a solid tumor may spread to other organs through metastatic tumor growth in advanced stages of the disease.

A hematological malignancy is a cancer type that affects the blood, BM, spleen and/or lymph nodes, and includes lymphomas, leukemias, myelomas and lymphoid malignancies. Hematological malignancies can derive from either of the two major blood cell lineages, i.e., myeloid and lymphoid cell lines. The myeloid cell line normally produces granulocytes, erythrocytes, thrombocytes, macrophages, and mast cells, whereas the lymphoid cell line produces B, T, NK and plasma cells. Lymphomas (e.g., Hodgkin's lymphoma), lymphocytic leukemias, and myeloma are derived from the lymphoid line, whereas acute and chronic myelogenous leukemia (AML, CML), myelodysplastic syndromes and myeloproliferative diseases are myeloid in origin. Waldenström's macroglobulinemia (WM) is an example of a B cell lymphoma, and it is shown herein to be amenable to treatment with an anti-CXCR4 antibody.

The term "CXCR4" ("C-X-C chemokine receptor 4") includes variants, isoforms, homologs, orthologs and paralogs. For example, antibodies specific for CXCR4 may, in certain cases, cross-react with CXCR4 from species other than human. In other embodiments, the antibodies specific for human CXCR4 may be completely specific for human CXCR4 and may not exhibit species or other types of cross-reactivity. The term "human CXCR4" refers to human sequence CXCR4, such as the complete amino acid sequence of human CXCR4 having GENBANK® accession number P61073 (SEQ ID NO: 51). CXCR4 is also known in the art as, for example, LESTR, Fusin or CD184. The human CXCR4 sequence may differ from human CXCR4 of SEQ ID NO: 51 by having, for example, conserved mutations or mutations in non-conserved regions, and the CXCR4 has substantially the same biological function as the human CXCR4 of SEQ ID NO: 51.

A "CXCR4-expressing cancer" or "CXCR4$^+$ cancer" is a cancer wherein the malignant cells that characterize this cancer express CXCR4 on the cell surface, preferably expressing a high level of CXCR4. A C1013G mutation in the CXCR4 gene, which has previously been associated with WHIM syndrome, is disclosed herein to be present in 28% of WM patients but is either absent from, or present in only 7% of, other B-cell lymphomas. C1013G CXCR4-associated WM refers to WM in which the C1013G mutation is present.

A "subject" includes a human or any nonhuman animal such as a nonhuman primate (e.g., a monkey), dog, rabbit, rodent, or chicken. In preferred embodiments, the subject is a human cancer patient such as a WM patient. The terms "subject", "patient" and "individual" are used interchangeably herein.

A "therapeutically effective amount" or "therapeutically effective dosage" of a drug or therapeutic agent, such as an anti-CXCR4 antibody, is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

"Treatment" or "therapy" of a subject refers to any type of intervention or process performed on, or administering an active agent to, the subject with the objective of reversing, alleviating, ameliorating, inhibiting, slowing down or prevent the onset, progression, development, severity or recurrence of a symptom, complication, condition or biochemical indicia associated with a disease.

The use of the alternative (e.g., "or") should be understood to mean either one, both, or any combination thereof of the alternatives. As used herein, the indefinite articles "a" or "an" should be understood to refer to "one or more" of any recited or enumerated component.

The term "about," "essentially" or "comprising essentially of" refers to a value or composition that is within an acceptable error range for the particular value or composition as determined by one of ordinary skill in the art, which will depend in part on how the value or composition is measured or determined, i.e., the limitations of the measurement system. For example, "about," "essentially" or "comprising essentially of" can mean within 1 or within more than 1 standard deviation per the practice in the art. Alternatively, "about," "essentially" or "comprising essentially of" can mean a range of plus or minus 20%, more usually a range of plus or minus 10%. Furthermore, particularly with respect to biological systems or processes, the terms can mean up to an order of magnitude or up to 5-fold of a value. When particular values or compositions are provided in the application and claims, unless otherwise stated, the meaning of "about," "essentially" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of this disclosure are described in further detail in the following subsections.

Therapeutic Anti-CXCR4 Antibodies

The production of exemplary anti-CXCR4 antibodies for use in the present therapeutic methods, including human monoclonal antibodies F7 (ulocuplumab; BMS-936564; MDX-1338), F9, D1 and E2, is described in detail in WO 2008/060367. Methods of using these antibodies to treat hematological malignancies are also described in WO 2008/060367 and WO 2013/071068. The anti-CXCR4 antibodies of this disclosure may be chimeric, humanized or, preferably, fully human antibodies, and are characterized by particular functional features or properties. For example, the antibodies bind to native human CXCR4 expressed on a cell surface. Preferably, an antibody of this disclosure binds to CXCR4 with high affinity, for example with a $K_D$ of $1 \times 10^{-8}$ M or less. The anti-CXCR4 antibodies of this disclosure preferably exhibit one or more of the following characteristics that are desirable for therapeutic applications:

(a) binding to human CXCR4 expressed on a cell surface;
(b) inhibiting binding of SDF-1 to CXCR4;
(c) inhibiting SDF-1-induced calcium flux in cells expressing CXCR4;
(d) inhibiting SDF-1-induced migration of cells expressing CXCR4;
(e) inhibiting capillary tube formation by human umbilical vein endothelial cells;
(f) binding to human CXCR4 with a $K_D$ of $1 \times 10^{-8}$ M or less;
(g) inducing apoptosis in cells expressing CXCR4;
(h) inhibiting proliferation of $CXCR4^+$ tumor cells in vitro;
(i) inhibiting $CXCR4^+$ tumor cell proliferation and/or inducing $CXCR4^+$ tumor cell apoptosis in vivo;
(j) inhibiting metastases of $CXCR4^+$ tumor cells; and
(k) increasing survival time of a $CXCR4^+$ tumor-bearing subject.

In preferred embodiments, the anti-CXCR4 antibodies of this disclosure bind to human CXCR4 with a $K_D$ of $1 \times 10^{-8}$ M or less, induce apoptosis in CXCR4-expressing cells, and exhibit at least five of the other properties listed above. In more preferred embodiments, the anti-CXCR4 antibodies of this disclosure exhibit all of the properties listed above.

In certain embodiments, an anti-CXCR4 antibody for use in the methods of this disclosure binds to human CXCR4 with a $K_D$ of $5 \times 10^{-8}$ M or less, binds to human CXCR4 with a $K_D$ of $2 \times 10^{-8}$ M or less, $5 \times 10^{-9}$ M or less, $4 \times 10^{-9}$ M or less, $3 \times 10^{-9}$ M or less, or $2 \times 10^{-9}$ M or less. In preferred embodiments, the anti-CXCR4 antibody is ulocuplumab (BMS-936564).

In one aspect, the anti-CXCR4 antibodies of this disclosure comprise the heavy chain and light chain CDR1's, CDR2's and CDR3's of F7, F9, D1 or E2, or combinations thereof. The amino acid sequences of the $V_H$ CDR1's of F7, F9, D1 and E2 are shown in SEQ ID NOs. 1-4, respectively. The amino acid sequences of the $V_H$ CDR2's of F7, F9, D1 and E2 are shown in SEQ ID NOs. 5-8, respectively. The amino acid sequences of the $V_H$ CDR3's of F7, F9, D1 and E2 are shown in SEQ ID NOs. 9-12, respectively. The amino acid sequences of the $V_k$ CDR1's of F7, F9, D1 and E2 are shown in SEQ ID NOs. 13-16, respectively. The amino acid sequences of the $V_k$ CDR2's of F7, F9, D1 and E2 are shown in SEQ ID NOs. 17-20, respectively. The amino acid sequences of the $V_k$ CDR3's of F7, F9, D1 and E2 are shown in SEQ ID NOs. 21-24, respectively. The amino acid sequences of the heavy chain variable region, light chain variable region, and 6 CDRs of the F7 (ulocuplumab) human monoclonal antibody are also shown in FIG. 1. The CDR regions identified throughout this disclosure were delineated using the Kabat system (Kabat et al., 1991).

In another aspect, the anti-CXCR4 antibodies of this disclosure comprise:

(a) the CDR1, CDR2 and CDR3 domains in a heavy chain variable region having the sequence set forth in SEQ ID NO: 25 or 41, and the CDR1, CDR2 and CDR3 domains in a light chain variable region having the sequence set forth in SEQ ID NO: 29 or 45;

(b) the CDR1, CDR2 and CDR3 domains in a heavy chain variable region having the sequence set forth in SEQ ID NO: 26 or 42, and the CDR1, CDR2 and CDR3 domains in a light chain variable region having the sequence set forth in SEQ ID NO: 30 or 46;

(c) the CDR1, CDR2 and CDR3 domains in a heavy chain variable region having the sequence set forth in SEQ ID NO: 27 or 43, and the CDR1, CDR2 and CDR3 domains in a light chain variable region having the sequence set forth in SEQ ID NO: 31 or 47; or (d) the CDR1, CDR2 and CDR3 domains in a heavy chain variable region having the sequence set forth in SEQ ID NO: 28 or 44, and the CDR1, CDR2 and CDR3 domains in a light chain variable region having the sequence set forth in SEQ ID NO: 32 or 48.

In other preferred embodiments, the anti-CXCR4 antibodies of this disclosure comprise:

(a) a heavy chain variable region CDR1 comprising consecutively linked amino acids having the sequence set forth in SEQ ID NO: 1 or conservative modifications thereof; a heavy chain variable region CDR2 comprising consecutively linked amino acids having the sequence set forth in SEQ ID NO: 5 or conservative modifications thereof; a heavy chain variable region CDR3 comprising consecutively linked amino acids having the sequence set forth in SEQ ID NO: 9 or conservative modifications thereof; a light chain variable region CDR1 comprising consecutively linked amino acids having the sequence set forth in SEQ ID NO: 13 or conservative modifications thereof, a light chain variable region CDR2 comprising consecutively linked amino acids having the sequence set forth in SEQ ID NO: 17 or conservative modifications thereof; and a light chain variable region CDR3 comprising consecutively linked amino acids having the sequence set forth in SEQ ID NO: 21;

(b) a heavy chain variable region CDR1 comprising consecutively linked amino acids having the sequence set forth in SEQ ID NO: 2 or conservative modifications thereof; a heavy chain variable region CDR2 comprising consecutively linked amino acids having the sequence set forth in SEQ ID NO: 6 or conservative modifications thereof; a heavy chain variable region CDR3 comprising consecutively linked amino acids having the sequence set forth in SEQ ID NO: 10 or conservative modifications thereof; a light chain variable region CDR1 comprising consecutively linked amino acids having the sequence set forth in SEQ ID NO: 14 or conservative modifications thereof; a light chain variable region CDR2 comprising consecutively linked amino acids having the sequence set forth in SEQ ID NO: 18 or conservative modifications thereof; and a light chain variable region CDR3 comprising consecutively linked amino acids having the sequence set forth in SEQ ID NO: 22;

(c) a heavy chain variable region CDR1 comprising consecutively linked amino acids having the sequence set forth in SEQ ID NO: 3 or conservative modifications thereof; a heavy chain variable region CDR2 comprising consecutively linked amino acids having the sequence set forth in SEQ ID NO: 7 or conservative modifications thereof; a heavy chain variable region CDR3 comprising consecutively linked amino acids having the sequence set forth in SEQ ID NO: 11 or conservative modifications thereof; a light chain variable region CDR1 comprising consecutively linked amino acids having the sequence set forth in SEQ ID NO: 15 or conservative modifications thereof, a light chain variable region CDR2 comprising consecutively linked amino acids having the sequence set forth in SEQ ID NO: 19 or conservative modifications thereof; and a light chain variable region CDR3 comprising consecutively linked amino acids having the sequence set forth in SEQ ID NO: 23; or (d) a heavy chain variable region CDR1 comprising consecutively linked amino acids having the sequence set forth in SEQ ID NO: 4 or conservative modifications thereof; a heavy chain variable region CDR2 comprising consecutively linked amino acids having the sequence set forth in SEQ ID NO: 8 or conservative modifications thereof; a heavy chain variable region CDR3 comprising consecutively linked amino acids having the sequence set forth in SEQ ID NO: 12 or conservative modifications thereof; a light chain variable region CDR1 comprising consecutively linked amino acids having the sequence set forth in SEQ ID NO: 16 or conservative modifications thereof; a light chain variable region CDR2 comprising consecutively linked amino acids having the sequence set forth in SEQ ID NO: 20 or conservative modifications thereof; and a light chain variable region CDR3 comprising consecutively linked amino acids having the sequence set forth in SEQ ID NO: 24.

In a preferred embodiment, the anti-CXCR4 antibody or antigen-binding portion thereof comprises a heavy chain variable region CDR1 comprising consecutively linked amino acids having the sequence set forth in SEQ ID NO: 1, a heavy chain variable region CDR2 comprising consecutively linked amino acids having the sequence set forth in SEQ ID NO: 5, a heavy chain variable region CDR3 comprising consecutively linked amino acids having the sequence set forth in SEQ ID NO: 9, a light chain variable region CDR1 comprising consecutively linked amino acids having the sequence set forth in SEQ ID NO: 13, a light chain variable region CDR2 comprising consecutively linked amino acids having the sequence set forth in SEQ ID NO: 17, and a light chain variable region CDR3 comprising consecutively linked amino acids having the sequence set forth in SEQ ID NO: 21.

The nucleotide and amino acid sequences of the heavy chain variable region of F7 are shown in FIG. 1A and in SEQ ID NOs. 33 and 25, respectively. The nucleotide and amino acid sequences of the light chain variable region of F7 are shown in FIG. 1B and in SEQ ID NOs. 37 and 29, respectively. Analysis of the F7 $V_H$ sequence using the Kabat system of CDR region determination led to the delineation of the heavy chain CDR1, CDR2 and CD3 regions as shown in FIG. 1A and in SEQ ID NOs: 1, 5 and 9, respectively, while the light chain CDR1, CDR2 and CD3 regions as shown in FIG. 1B and in SEQ ID NOs: 13, 17 and 21, respectively.

The nucleotide and amino acid sequences of the heavy chain variable region of F9 are shown in SEQ ID NOs. 34 and 26, respectively, and for the F9 light chain variable region in SEQ ID NOs. 38 and 30, respectively. The sequences the F9 heavy chain CDR1, CDR2 and CD3 regions as shown in SEQ ID NOs. 2, 6 and 10, respectively, and the F9 light chain CDR1, CDR2 and CD3 sequences as shown in SEQ ID NOs. 14, 18 and 22, respectively.

The nucleotide and amino acid sequences of the heavy chain variable region of D1 are shown in SEQ ID NO: 35 and 27, respectively, and for the D1 light chain variable region in SEQ ID NOs. 39 and 31, respectively. The sequences the D1 heavy chain CDR1, CDR2 and CD3 regions as shown in SEQ ID NOs. 3, 7 and 11, respectively, and the F9 light chain CDR1, CDR2 and CD3 sequences as shown in SEQ ID NOs. 15, 19 and 23, respectively.

The nucleotide and amino acid sequences of the heavy chain variable region of E2 are shown in SEQ ID NO: 36 and 28, respectively, and for the E2 light chain variable region in SEQ ID NOs. 40 and 32, respectively. The sequences the E2 heavy chain CDR1, CDR2 and CD3 regions as shown in SEQ ID NOs. 4, 8 and 12, respectively, and the F9 light chain CDR1, CDR2 and CD3 sequences as shown in SEQ ID NOs. 16, 20 and 24, respectively.

Additionally, alternative forms of F7, F9, D1 and E2, in which certain framework residues were substituted with a germline residue, were created and are referred to herein as F7GL, F9GL, D1GL and E2GL. The $V_H$ amino acid sequences of F7GL, F9GL, D1GL and E2GL are shown in SEQ ID NOs. 41, 42, 43 and 44, respectively. The $V_L$ amino acid sequences of F7GL, F9GL, D1GL and E2GL are shown in SEQ ID NOs. 45, 46, 47 and 48, respectively.

In one aspect, anti-CXCR4 antibodies for use in the methods of this disclosure cross-compete for binding to CXCR4 with any of mAb F7 (ulocuplumab; having $V_H$ and $V_L$ sequences as shown in SEQ ID NOs: 25 and 29, respectively), mAb F9 (having $V_H$ and $V_L$ sequences as shown in SEQ ID NOs: 26 and 30, respectively), mAb D1 (having $V_H$ and $V_L$ sequences as shown in SEQ ID NOs: 27 and 31, respectively), and mAb E2 (having $V_H$ and $V_L$ sequences as shown in SEQ ID NOs: 28 and 32, respectively). Antibodies that cross-compete for binding to CXCR4 bind to the same epitope region (i.e., the same or an overlapping epitope) on CXCR4.

In certain embodiments, the cross-competing anti-CXCR4 monoclonal antibody comprises a $V_H$ region comprising consecutively linked amino acids having a sequence derived from a human $V_H$ 3-48 germline sequence as set forth in SEQ ID NO: 49 and/or a $V_L$ region comprising consecutively linked amino acids having a sequence derived from a human $V_K L15$ germline sequence as set forth in SEQ ID NO: 50. The cross-competing antibodies can be identified based on their ability to cross-compete with ulocuplumab (F7), F9, D1, E2 or any other reference anti-CXCR4 antibody in a standard CXCR4 binding assay, for example, flow cytometry with CEM cells, wherein the reference antibody is labeled with FITC and the ability of a test antibody to inhibit the binding of the FITC-labeled reference antibody to CEM cells is evaluated.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, subcutaneous, intramuscular, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

Dosage regimens are adjusted to provide the optimum desired response, e.g., a therapeutic response or minimal adverse effects.

For administration of a human anti-CXCR4 antibody, the dosage ranges from about 0.0001 to 100 mg/kg, preferably from about 0.01 to about 20 mg/kg, and more preferably 0.1 to 10 mg/kg, of the subject's body weight. For example, dosages can be 0.1, 0.3, 1, 3, 5 or 10 mg/kg body weight, and more preferably, 0.3, 1, 3, or 10 mg/kg body weight. The dosing schedule is typically designed to achieve exposures that result in sustained receptor occupancy based on typical pharmacokinetic properties of an antibody. An exemplary treatment regime entails administration once per week, once every two weeks, once every three weeks, once every four weeks, once a month, once every 3 months or once every three to 6 months. Considering that an IgG4 antibody typically has a half-life of 2-3 weeks, a preferred dosage regimen for an anti-CXCR4 antibody of the disclosure comprises 0.3-20 mg/kg body weight, preferably 1-10 mg/kg body weight, via intravenous administration, with the antibody being given every 7 or 14 days in up to 6-week, 8-week or 12-week cycles until complete response or confirmed progressive disease.

The dosage and scheduling may change during a course of treatment. For example, dosage regimens for an anti-CXCR4 antibody of this disclosure include 1, 3 or 10 mg/kg body weight via intravenous (IV) administration, with the antibody being given using one of the following dosing schedules: (i) every 7 days in up to 6-week cycles; (ii) every two weeks for up to six dosages, then every three months; (iii) every three weeks; (iv) 1-10 mg/kg body weight once followed by 1 mg/kg body weight every 2-3 weeks.

The C1013G/CXCR4 mutation, found in 28% of WM patients, plays an activating role in WM cells, as documented by significant tumor proliferation and dissemination to extramedullary organs, leading to disease progression and decreased survival. Administration of the anti-CXCR4 antibody, BMS-936564, led to significant tumor reduction and abrogation of extramedullary dissemination in vivo, in a C1013G/CXCR4 WM model (see Examples 6 and 7). In certain embodiments of the present invention, a patient afflicted with C1013G/CXCR4-associated WM is treated with a therapeutic regimen comprising administering an anti-CXCR4 antibody or antigen-binding portion thereof to the patient at a dose of at least twice, at least three times, or at least five times, the dose administered in treating a WM patient carrying the wild-type CXCR4 gene, and/or a frequency at least two times, at least three times, or at least five times higher than the frequency administered in treating a WM patient carrying the wild-type CXCR4 gene.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Uses and Methods of the Invention

The present disclosure provides methods for treating a subject afflicted with WM comprising administering to the subject a therapeutically effective amount of an antibody that specifically binds to a CXCR4 receptor and exhibits certain functional properties that are desirable for therapeutic use.

This disclosure also provides methods for treating a subject afflicted with C1013G/CXCR4-associated WM comprising administering to the subject a therapeutically effective amount of an anti-CXCR4 antibody.

CXCR4 is known to be expressed on a wide variety of tumor cells types, to be involved in tumor metastasis, HIV infection, inflammatory conditions, and angiogenesis or neovascularization (see, e.g., WO 2008/060367 and WO 2013/071068). Accordingly, the anti-CXCR4 antibodies disclosed herein can be used in a variety of clinical situations, but the present disclosure focuses on the use of these antibodies for the treatment of cancer and, in particular, WM.

Role of CXCR4 in Cancer

Over-expression of CXCR4 has also been demonstrated in about 75% of cancers, and in certain situations an inverse correlation has been established between CXCR4 expression and patient prognosis or survival. Non-limiting examples of cancer types associated with CXCR4 expression or the CXCR4/CXCL12 pathway include solid tumors such as breast (Muller et al., 2001), ovarian (Scotton et al., 2001), prostate (Taichman et al., 2002), non-small cell lung (Spano et al., 2004), pancreatic (Koshiba et al., 2000), colorectal (Zeelenberg et al., 2003), kidney (Schrader et al., 2002), and thyroid cancer (Hwang et al., 2003), nasopharyngeal carcinoma (Wang et al., 2005), melanoma (Scala et al., 2005), renal cell carcinoma (Staller et al., 2003), neuroblastoma (Geminder et al., 2001), glioblastoma (Rempel et al., 2000), rhabdomyosarcoma (Libura et al., 2002), and osteosarcoma (Laverdiere et al., 2005), as well as hematological malignancies such as acute lymphoblastic leukemia (Crazzolara et al., 2001), acute myeloid leukemia (AML) (Mohle et al., 1998; Rombouts et al., 2004), multiple myeloma (MM) (Alsayed et al., 2007; Azab et al., 2009), chronic lymphoid leukemia (Mohle et al., 1999; Burger et al., 1999), chronic myeloid leukemia (Jin et al., 2008), WM (Ngo et al., 2008), and non-Hodgkin's lymphoma (NHL) (Bertolini et al., 2002; Weng et al., 2003).

Additionally, this pathway is implicated in stimulating the metastatic process in multiple neoplasms (Murphy, 2001). In clinical studies, CXCR4 has been associated with increased propensity for metastasis and decreased survival and has been identified as a prognostic indicator for AML, breast, colorectal, non-small-cell lung, ovarian and pancreatic carcinoma in which greater expression of CXCR4 correlates with disease severity (Spoo et al., 2007; Hiller et al., 2011; Ottaiano et al., 2006; Spano et al., 2004; Jiang et al.; 2006; Marechal et al., 2009).

BM-MSCs secrete CXCL12 (SDF-1) and the interaction with CXCR4 is essential for homing and maintaining hematopoietic stem cells within the BM microenvironment (Mohle et al., 1998). Leukemic cells express high levels of CXCR4, and the pathway plays a critical role in leukemic cell migration into the BM which in turn, supports their growth and survival. CXCR4 is essential for metastatic spread to organs such as BM where CXCL12 is expressed. Collectively, CXCR4 plays an important role in both homing and retention of hematopoietic stem cells in the BM and an antagonist of CXCR4 mobilizes stem cells into the bloodstream, as demonstrated with the small-molecule CXCR4 antagonist, AMD3100 (plerixafor; Mozobil) which was approved by the FDA for use in combination with granulocyte-colony stimulating factor for autologous transplants in NHL and MM patients (Dar et al., 2011). Another CXCR4 inhibitor, AMD3465, was shown to antagonize CXCL12- and stroma-induced chemotaxis and inhibited CXCL12-induced activation of prosurvival signaling pathways in leukemic cells (Zeng et al., 2009). Further, it was demonstrated that AMD3465, alone or in combination with granulocyte colony-stimulating factor, induced mobilization of AML cells and progenitor cells into circulation and enhanced antileukemic effects of chemotherapy and sorafenib, resulting in markedly reduced leukemia burden and prolonged survival of the animals (Zeng et al., 2009). Such findings suggest that disruption of CXCR4/CXCL12 interactions may be used to sensitize leukemic cells to chemotherapy by targeting their protective BM microenvironment.

As described in WO 2008/060367 and WO 2013/071068, novel first-in-class human therapeutic monoclonal antibodies directed to CXCR4 have been developed. These monoclonal antibodies bind to CXCR4-expressing cells with low nanomolar affinity, block CXCL12 binding to CXCR4-expressing cells and inhibit CXCL12-induced migration and calcium flux with low nanomolar $EC_{50}$ values. Because CXCR4 plays a role in multiple fundamental aspects of cancer including proliferation, migration/invasion and angiogenesis, an antagonist has potentially multiple means to intervene in malignancies where CXCR4 is expressed. Significantly, in addition to blocking CXCL12-induced calcium flux and migration, WO 2013/071068 teaches that antibody-dependent induction of apoptosis of CXCR4-expressing tumor cells is a mechanism of action of these human anti-CXCR4 antibodies. Antibody-induced apoptosis resulted in robust in vivo efficacy across multiple hematopoietic tumor xenograft models. In contrast, small-molecule CXCR4 antagonists such as AMD3100 increase mobilization of $CXCR4^+$ tumor cells from the BM and thereby increase chemosensitization but do not directly kill such tumor cells, which suggests enhanced efficacy of anti-CXCR4 antibodies compared to small-molecule CXCR4 antagonists in killing cancer cells.

Waldenström's Macroglobulinemia

WM, also called lymphoplasmacytic lymphoma, is an indolent (slow-growing) subtype of non-Hodgkin lymphoma (NHL). The disease is characterized by an uncontrolled clonal proliferation of terminally differentiated B lymphocytes, i.e., white blood cells formed in the BM and lymph nodes. A unique characteristic of the disease is that the B-cells produce excess amounts of a monoclonal IgM, which can result in a thickening of the blood known as hyperviscosity. This IgM protein may lead to many symptoms, including fatigue, unexplained weight loss, enlarged lymph nodes or spleen, impaired kidney function, systemic amyloidosis, weakness and unexplained bleeding. The proliferation of B-cells also interferes with the production of red blood cells, resulting in anemia.

WM is a rare disease, with only about 1,500 cases per year in the U.S. There is no single accepted treatment for WM, but therapy regimens that include a combination of biological agents that stimulates the immune system and chemotherapy have provided promising results (Treon, 2009). Some examples of combination therapies currently used in the treatment of WM patients include BDR: bortezomib (VELCADE®), dexamethasone and rituximab (RITUXAN®) (Treon et al., 2009); RCD: cyclophosphamide (CYTOXAN®; NEOSAR®), dexamethasone and rituximab (Dimopoulos et al., 2007); R-CHOP: cyclophosphamide, doxorubicin (ADRIAMYCIN®), vincristine (ONCOVIN®), prednisone and rituximab; CPR: cyclophosphamide, prednisone, and rituximab; VR: bortezomib and rituximab; FR: fludarabine (FLUDARA®) and rituximab; and TR: thalidomide (THALOMID®) and rituximab. Objective response rates are high (>80%) but complete response rates are low (0-15%). Therapies under investigation include ibrutinib (IMBRUVICA®), a selective Bruton's tyrosine kinase (BTK) inhibitor; alemtuzumab (CAMPATH®), which targets CD52 on the surface of WM cells; ofatumumab (ARZERRA®), which targets the CD20 molecule on the surface of B cells, bendamustine (TREANDA®), which attacks the DNA of cancer cells and disrupts the cell-division cycle; the mTOR inhibitor, everolimus (AFINITOR®, ZORTRESS®), which inhibits cell growth and division; and carfilzomib (KYPROLIS™), a selective proteasome inhibitor. In certain embodiments of the methods for treating WM or C1013G/CXCR4-associated WM disclosed herein, any of the preceding agents, or any combination thereof, may be used in combination with an anti-CXCR4 antibody of this disclosure. In other embodiments, the anti-CXCR4 antibody is used after progression of the WM patient on any of these anti-WM therapies that are used, or are under development, for treating WM.

Role of CXCR4 and C1013G/CXCR4 Mutation in Waldenström's Macroglobulinemia

It has previously been shown that WM cells express high levels of chemokine and adhesion receptors, including CXCR4 and VLA-4, and that CXCR4 is essential for the CXCL12-induced migration and trans-endothelial migration of WM cells (Ngo et al., 2008). CXCR4 knockdown or the CXCR4 inhibitor, AMD3100, was shown to significantly inhibit migration of WM cells as well as their adhesion to fibronectin, stromal cells, and endothelial cells. Decreased adhesion of WM cells to stromal cells induced by AMD3100 led to increased sensitivity of these cells to cytotoxicity, i.e., inhibition of proliferation, by bortezomib. It was further demonstrated that CXCR4 and VLA-4 directly interact in response to CXCL12. Thus, the CXCR4/CXCL12 axis has been shown to interact with VLA-4 in regulating migration and adhesion of WM cells in the BM microenvironment (Ngo et al., 2008).

Examination of 418 patients with B-cell lymphoproliferative disorders as described herein (see Example 1; Table 1) revealed that 28% of patients with low-grade lymphoplasmacytic lymphoma (WM) present with the C1013G/CXCR4 variant. Studies were therefore undertaken to dissect the functional relevance of C1013G/CXCR4 variant, to evaluate its putative role in mediating WM cell dissemination and disease progression using in vivo models, and to identify novel therapeutic approaches that may target the C1013G/CXCR4-mutated lymphoplasmacytic cells. These studies demonstrated that CXCR4 plays a crucial role supporting WM cell homing to the BM as well as WM dissemination to distant organs, as shown in vivo by using CXCR4 gain-of-function studies (Example 2). Importantly, WM cells harboring the C1013G/CXCR4 variant exerted a similar phenotype compared with the CXCR4-overexpressing cells (Example 3), suggesting that the C1013G/CXCR4 variant may represent a functionally active mutation. Moreover, the C1013G/CXCR4-mutated cells showed dissemination to lymph nodes, in vivo, compared with either control cells or the CXCR4-overexpressing WM cells (Example 3), indicating that the generated C1013G/CXCR4 variant was able to recapitulate what was observed clinically in patients. Notably, C1013G/CXCR4-mutated cells were able to colonize extramedullary tissues, such as lung and kidney in vivo (Example 3), reflecting the observed phenotype in patients with extramedullary WM, where the variant has been detected in all the cases of lung and kidney involvement.

The observed C1013G/CXCR4 variant is one of the mutations originally described in WHIM syndrome. This is a rare, inherited, heterozygous, autosomal dominant disease characterized by aberrantly functioning immunity. It is caused by mutations of CXCR4, responsible for the truncation of the carboxy-terminal talk (C-tail) of the receptor that impairs its intracellular trafficking, leading to increased responsiveness to chemokine ligand and retention of neutrophils in BM (Balabanian et al., 2005; 2008; Hernandez et al., 2003; Taniuchi et al., 2005). Recent evidence has documented the presence of the WHIM-like C1013G/CXCR4 mutation in WM patients (Hunter et al., 2014), but the in vivo functional sequelae of this mutation in WM, and whether the somatic variant occurs in other B-cell lymphoproliferative disorders where CXCR4 mediates tumor cell trafficking and dissemination, have not been described before the present study. The increased ability of C1013G/CXCR4-mutated cells to disseminate in vivo leading to disease progression was supported by enrichment of genes related to cell invasiveness, antiapoptosis, cell proliferation, and oncogenesis (Example 3). This resulted in the upregulation of pro-survival pathways in mutated cells compared with control cells. These effects were reversed when WM-harboring mice, injected with either C1013G/CXCR4-mutated cells or control cells, were treated with the anti-CXCR4 antibody, ulocuplumab, as described below.

Altered Sensitivity of Waldenström's Macroglobulinemia Cells Harboring the C1013G/CXCR4-Mutation to Conventionally Used Anti-WM Agents Drugs commonly used to treat WM include agents such as rituximab, chlorambucil (LEUKERAN®), cladribine (LEUSTATIN®), fludarabine, bortezomib, bendamustine, alone and in various combinations. Additional therapies to treat refractory/relapsed WM include ofatumumab for patients who are allergic to rituximab, everolimus, alemtuzumab, and high-dose chemotherapy with an autologous or allogeneic stem cell transplant. Several new drugs and drug combinations are being studied in clinical trials for WM (some for refractory/relapsed disease), including carfilzomib, ibrutinib and panobinostat (LBH-589).

Ibrutinib, an orally-administered inhibitor of the enzyme Bruton's tyrosine kinase, was recently approved by the U.S. Food and Drug Administration (FDA) for the treatment of mantle cell lymphoma and chronic lymphocytic leukemia, and in February 2013 was granted Breakthrough Therapy Designation by the FDA as a monotherapy for patients with WM. Ibrutinib has been reported to be highly active, and well-tolerated in patients with relapsed or refractory WM (Treon et al., 2013), and in October 2014 a Supplemental New Drug Application (sNDA) was submitted to the FDA based on data from a Phase 2 clinical trial (ClinicalTrials.gov Identifier: NCT01614821) of ibrutinib in WM patients previously treated with at least one systemic WM regimen. However, the presence of WHIM-like CXCR4 mutations has been shown to confer decreased sensitivity to ibrutinib-mediated growth suppression in WM cells (Cao et al., 2013; Treon et al., 2013), with a major response rate of only 30% in patients with WHIM-like CXCR4 mutations vs. 77% for patients with wild-type CXCR4 (Treon et al., 2013).

Further, it has been shown herein (Example 4) that the C1013G/CXCR4 somatic variant is associated with WM cell resistance to conventionally used anti-WM small molecules, including the BTK inhibitor, ibrutinib, the mTOR inhibitor, everolimus, and the phosphatidylinositol-3-kinase (PI3K) inhibitor, idelalisib (ZYDELIG®), supporting the role of this variant in mediating drug resistance. This result suggests that mTOR, BTK and PI3K inhibitors may not be effective in treating patients whose WM cells harbor the C1013G/CXCR4-mutation. In contrast, C1013G/CXCR4-mutated WM cells and unmutated control cells were equally sensitive to the proteasome inhibitor drugs carfilzomib and bortezomib (Example 4), thus suggesting a possible combinatory regimen of ulocuplumab with proteasome inhibitors in WM patients harboring the C1013G/CXCR4 somatic variant.

Without being bound by any particular theory, it is proposed that BTK, PI3K, and mTOR inhibitors were not effective against C1013G/CXCR4-mutated cells because of the upregulation of genes related to those specific pathways. Moreover, it was confirmed that mutated CXCR4 cells presented with enrichment of RAF as well as mitogen-activated protein kinase/mitogen-activated protein kinase kinase and mTOR pathways, thus further suggesting the presence of crosstalk between RAF and mitogen-activated protein kinase kinase/ERK/mTOR pathways (Downward, 2003; Lim and Counter, 2005). In contrast, NF-κB and NF-κB-related apoptotic genes were not differentially modulated in CXCR4-mutated cells compared with control cells (data not shown). This may explain, at least in part, the presence of BTK-, mTOR-, and PI3K-inhibitor resistance and sensitivity to proteasome inhibitors in mutated WM cells compared with wild-type cells.

Treatment of Waldenström's Macroglobulinemia with an Anti-CXCR4 Antibody

An anti-CXCR4 antibody, BMS-936564, is shown herein to inhibit migration of WM cell lines towards either primary WM bone marrow mesenchymal stromal cells (BM-MSCs) or the CXCR4 ligand, CXCL12 (see Example 5). This anti-CXCR4 antibody also inhibits WM cell adhesion to WM BM-MSCs and inhibits WM cell proliferation in the presence of WM BM-MSCs. In addition, evidence is also provided that the antibody may directly induce apoptosis in WM cells (Example 5). Accordingly, the present disclosure provides methods for treating a subject afflicted with WM comprising administering to the subject a therapeutically effective amount of an antibody or an antigen-binding portion thereof that specifically binds to a CXCR4 receptor expressed on the surface of a cell, including a WM cell. In preferred embodiments, the antibody used in the instant methods is an anti-CXCR4 antibody of this disclosure that specifically binds to a CXCR4 receptor and exhibits certain functional properties that are desirable for therapeutic use. Such functional properties include high-affinity binding to human CXCR4 expressed on a cell surface, inhibiting SDF-1-induced calcium flux in, and migration of, cells CXCR4-expressing cells, inhibiting CXCR4$^+$ tumor cell proliferation and/or inducing CXCR4$^+$ tumor cell apoptosis in vivo, increasing survival time of a CXCR4$^+$ tumor-bearing subject, and/or other functional properties described herein.

The disclosure also provides experimental evidence that a C1013G mutation in the CXCR4 gene is present in about 28% of WM patients and in about 20% IgM-MGUS patients, but is rare or absent in several other B-cell cancers tested (see Example 1). Thus, among B-cell lymphoproliferative disorders, the C1013G/CXCR4 mutation characterizes WM patients. Data are also provided showing that CXCR4 over-expression facilitates in vivo WM cell growth and dissemination (Example 2). The presence of the C1013G/CXCR4 mutation was shown to increase adhesion and proliferation of WM cells in the presence of primary WM BM-MSCs, recapitulating the effects of CXCR4 over-expression of in WM cells (Example 3). Thus, the C1013G/CXCR4 mutation is an activating mutation in WM cells as evidenced by significant tumor proliferation and dissemination to extramedullary organs, leading to disease progression and decreased survival.

Notably, ulocuplumab was shown to effectively target adhesion, migration and proliferative properties of CXCR4-mutated WM cells in the context of the BM microenvironment both in vitro and in vivo (see Example 6). Administration of ulocuplumab led to significant tumor reduction and abrogation of extramedullary dissemination in vivo in a C1013G/CXCR4 WM model. These findings demonstrate that CXCR4 is a critical regulator of WM molecular pathogenesis and is an important therapeutic target. The use of an anti-CXCR4 antibody to successfully target both wild-type and C1013G/CXCR4-mutated WM cells, as described in Examples 5-7, provides a sound basis for translating these observations into clinical trials for WM patients.

Accordingly, the disclosure provides methods for treating a subject afflicted with WM, including C1013G/CXCR4-associated WM, comprising administering to the subject a therapeutically effective amount of an antibody or an antigen-binding portion thereof that specifically binds to a CXCR4 receptor expressed on the surface of a cell, including a WM cell. In certain embodiments of the present methods, the subject is a human WM patient, preferably a human patient afflicted with C1013G/CXCR4-associated WM. In certain preferred embodiments, the antibody or antigen-binding portion thereof binds to a human CXCR4 receptor expressed on a cell surface, such as a human CXCR4 receptor carrying the C1013G mutation expressed on a cell surface. In certain embodiments, the antibody or antigen-binding portion thereof is of an IgG1, IgG2, IgG3 or IgG4 isotype. In certain other embodiments, the antibody or antigen-binding portion thereof is of an IgG1 isotype. In other embodiments, the antibody or antigen-binding portion thereof is of an IgG4 isotype. In further embodiments, the antibody or antigen-binding portion thereof is a monoclonal antibody or an antigen-binding portion thereof. In yet other embodiments, the antibody or antigen-binding portion thereof is a chimeric, humanized or human antibody or an antigen-binding portion thereof. Preferably, the antibody or antigen-binding portion thereof is a human antibody or an antigen-binding portion thereof. In more preferred embodiments, the antibody or fragment thereof is ulocuplumab or a CXCR4-binding fragment thereof.

Importantly, it has been disclosed herein that C1013G/CXCR4-mutated WM cells are resistant to three important classes of drugs used to treat B cell malignancies and that are being being actively tested for treatment of WM, i.e., BTK inhibitors, exemplified by ibrutinib, mTOR inhibitors, exemplified by everolimus, and PI3K inhibitors, exemplified by idelalisib (Example 4). In contrast, it was shown that an anti-CXCR4 antibody is effective in inhibiting proliferation and migration of both C1013G/CXCR4-mutated and unmutated WM cells. These results suggest that mTOR, BTK and PI3K inhibitors will not be highly effective in treating patients whose WM cells harbor the C1013G/CXCR4-mutation, and underscore the utility of an anti-CXCR4 antibody for treating such C1013G/CXCR4-WM variants.

Ulocuplumab has been shown herein to target WM cells, independently of their mutational status, by inhibiting activation of pro-survival signaling pathways, stimulating pro-apoptotic cascades, and inhibiting WM cell dissemination in vivo (Examples 5 and 6). Accordingly, in certain embodiments of the disclosed therapeutic methods, a WM patient is screened for the presence of the C1013G/CXCR4 mutation to thereby identify patients who are not suitable for treatment with a BTK, mTOR or PI3K inhibitor drug, wherein such patients are suitable for treatment with an anti-CXCR4 antibody. Such WM patients may not be good candidates for treatment with a BTK, mTOR or PI3K inhibitor drug, and may instead be treated with an anti-CXCR4 antibody of the disclosure as first-line monotherapy. In certain preferred embodiments of this method, the anti-CXCR4 antibody is ulocuplumab. In other embodiments, the patient afflicted with C1013G/CXCR4-WM is treated with a combination of an anti-CXCR4 antibody, such as ulocuplumab, and an anti-WM agent such as ibrutinib, everolimus, idelalisib, carfilzomib and/or bortezomib. In further embodiments, the C1013G/CXCR4-WM patient is treated with an anti-CXCR4 antibody, alone or in combination with another anti-WM agent, as second- or third-line therapy after the patient has failed one or more treatments. For example, the anti-CXCR4 antibody may be administered after the WM patient has failed first-line treatment with ibrutinib, or the antibody may be administered after the patient has failed both first-line treatment with a chemotherapeutic BDR (bortezomib, dexamethasone and rituximab) or RCD (cyclophosphamide, dexamethasone and rituximab) regimen and second-line treatment with ibrutinib.

Anti-CXCR4 Antibody for Monotherapy in Waldenström's Macroglobulinemia

Exposure of WM cells to BMS-936564 resulted in an increase of caspase-9 and PARP cleavage (Example 5). Neutralization of CXCR4 with BMS-936564 also increased levels of phospho(p)-GSK3-β and p-β-catenin up-regulation, leading to β-catenin degradation. BMS-936564 similarly increased caspase-9- and PARP-cleavage in C1013G/CXCR4-associated WM cells and modulated GSK3-β/β-catenin signaling, leading to up-regulation of p-GSK3-β/p-β-catenin and β-catenin degradation (Example 6). These effects of BMS-936564 are consistent with the activation of apoptotic pathways in WM and C1013G/CXCR4-associated WM cells, and mirror the pro-apoptotic effect of BMS-936564 demonstrated in other B-cell malignancies (WO 2013/071068; Kuhne et al., 2013). Accordingly, in certain embodiments of these methods for treating a WM patient, the anti-CXCR4 antibody or fragment thereof induces apoptosis of a CXCR4- or C1013G/CXCR4-expressing cell.

The apoptotic effect of the disclosed anti-CXCR4 antibodies, a property not exhibited by small-molecule CXCR4 antagonists, e.g., AMD3100, indicates that these antibodies can be used alone, as monotherapy, to treat patients with cancer. Previous studies on the effect of CXCR4 antagonists in in vivo AML and MM tumor models have suggested that these antagonists are effective in enhancing the sensitivity of the tumors cells to chemotherapy (Azab et al., 2009; Zeng et al., 2009). In addition, the data presented herein in Example 6 demonstrate that ulocuplumab, administered as monotherapy, inhibited WM dissemination in mice injected with C1013G/CXCR4 WM cells, evidenced by significant reduction of $CXCR4^+/CD20^+$ cell infiltration in femur, liver, kidney and lung in treated mice compared to control antibody-treated mice. Similarly, Example 7 shows that ulocuplumab inhibited wild-type WM cell dissemination in vivo. These results are consistent with the significant tumor growth inhibition achieved when ulocuplumab was administered as monotherapy in a wide variety of AML, NHL and MM models (WO 2013/071068; Kuhne et al., 2013).

Accordingly, in certain embodiments of the present treatment methods for treating wild-type WM or C1013G/CXCR4-associated WM, the anti-CXCR4 antibody or fragment thereof is administered as monotherapy. In preferred embodiments, the antibody or fragment thereof induces apoptosis of a CXCR4 or C1013G/CXCR4-expressing cell. Thus, this disclosure also provides a method of inducing apoptosis of CXCR4- or C1013G/CXCR4-expressing WM cells comprising administering to a WM subject a therapeutically effective amount of an anti-CXCR4 antibody of the disclosure.

Combination of Anti-CXCR4 and Anti-Cancer Therapy for Treatment of Waldenström's Macroglobulinemia As described in Example 7, each of BMS-936564 and bortezomib significantly reduced tumor cells within the BM and levels of serum IgM. However, BMS-936564 and bortezomib in combination acted synergistically to cause even more significant reductions in tumor cells and serum IgM levels. These results are consistent with previous demonstrations that the CXCR4/CXCL12 axis plays a major role in homing and trafficking of MM cells to the BM, and disruption of the interaction of MM cancer cells with the BM sensitizes these cells to therapeutic agents (Alsayed et al., 2007; Azab et al., 2009; Kuhne et al., 2013; WO 2013/071068).

In certain embodiments of the disclosed methods, the anti-CXCR4 antibody or antigen-binding fragment thereof binds to the CXCR4 receptor and inhibits the activity of the receptor. This disrupts the homing and maintenance of WM stem cells within the BM microenvironment and/or increases mobilization of WM cells from the BM to the periphery, and thereby increases the sensitivity of WM cancer cells to one or more anti-cancer treatments such as radiation treatment or the administration of chemotherapeutic agents.

Accordingly, in certain embodiments, the anti-CXCR4 antibodies of the disclosure are used in combination other cancer treatments, such as surgery and/or radiation, and/or can be co-administered with one or other more therapeutic agents, e.g., a cytotoxic agent, a radiotoxic agent or an immunosuppressive agent, which enhances or augments the therapeutic effect of the anti-CXCR4 antibodies. The antibody can be linked to the agent (as an immunoconjugate) or can be administered separate from the agent. In the latter case (separate administration), the antibody can be administered before, after or concurrently with the agent or can be co-administered with other known therapeutic agents, including conventional chemotherapeutic drugs and antibodies that bind tumor-associated antigens or immunoregulatory targets.

Anti-cancer drugs for use in these methods include, among others, bortezomib, carfilzomib, ibrutinib, idelalisib, panobinostat, dexamethasone, rituximab, thalidomide, cyclophosphamide, lenalidomide, doxorubicin, vincristine, prednisone, fludarabine, chlorambucil, bendamustine, cladribine, alemtuzumab, ofatumumab, everolimus, cisplatin, bleomycin sulfate, carmustine, mitoxantrone, etoposide, cytarabine, ifosfamide, carboplatin, and etoposide. It is demonstrated herein that both the C1013G/CXCR4-mutated and unmutated WM cells were equally sensitive to the proteasome inhibitors, carfilzomib and bortezomib (Example 4). Moreover, a combination of ulocuplumab and bortezomib acted synergistically in reducing WM tumor cells within the BM and in reducing serum IgM levels in vivo, and in inducing toxicity in WM cells in vitro (Example 7). Taken together, these data strongly suggest that a combinatory regimen of ulocuplumab with proteasome inhibitors, e.g., bortezomib or carfilzomib, is highly efficacious in treating WM patients harboring either wild-type CXCR4 or the C1013G/CXCR4 somatic variant. Co-administration of an anti-CXCR4 antibody, or antigen binding fragment thereof, of the present disclosure with anti-neoplastic agents provides at least two anti-cancer agents that operate via different mechanisms to exert a cytotoxic effect to human tumor cells. In addition to the possible synergistic interaction of the anti-CXCR4 antibody and the other agent(s), such co-administration can help overcome problems due to development of resistance to drugs or a change in the antigenicity of the tumor cells that would render them unreactive with the anti-CXCR4 antibody.

Thus, the anti-CXCR4 antibodies of this disclosure may be used to potentiate the effect of chemotherapeutics by their ability to release malignant cells from the protective environment of the BM. As described above, in addition to mobilizing WM cells and increasing their chemosensitization, these antibodies have been shown to have the additional effect of directly killing MM cells by apoptosis and are therefore effective in treating WM, including C1013G/CXCR4-associated WM, when administered as monotherapy.

Dosages

In certain embodiments of the disclosed methods for treating WM, the therapeutically effective amount of the anti-CXCR4 antibody or antigen-binding portion thereof comprises a dose ranging from 0.1 to 20 mg/kg body weight. For example, in certain embodiments the therapeutically effective amount of the antibody or antigen-binding portion thereof comprises a dose of 0.1, 0.3, 0.5, 1, 3, 5, 10 or 20 mg/kg. In preferred embodiments, the dose is 1, 3 or 10 mg/kg. In other embodiments, the antibody or antigen-binding portion thereof is administered at a dosing schedule of once per week, once every two weeks, once every three weeks, or once a month. In preferred embodiments, the antibody or antigen-binding portion thereof is administered at a dosing schedule of once every 7 or 14 days. In certain embodiments, the anti-CXCR4 antibody is administered as monotherapy for the duration of the treatment. In other embodiments, the anti-CXCR4 antibody is administered weekly, in Cycle 1 for the first two weeks as monotherapy, and then in combination with a chemotherapy regimen that includes, for example, bortezomib, dexamethasone and rituximab (BDR), or cyclophosphamide, dexamethasone and rituximab (RCD). In certain preferred embodiments, the antibody or antigen-binding portion thereof is administered intravenously. In other preferred embodiments, the antibody or antigen-binding portion thereof is administered subcutaneously.

For example, for treatment of WM with ulocuplumab in combination with BDR, an exemplary dosage regimen comprises: (1) ulocuplumab (1, 3, or 10 mg/kg) administered as a single 60 minute intravenous infusion on Days 1, 8, 15, 22, and 29 (Cycle 1) and on Days 1, 8, and 15 (Cycle 2 and subsequent cycles); (2) bortezomib (1.3 mg/m$^2$) administered as a 3-5 second intravenous push on Days 15, 18, 22, and 25 (Cycle 1) and on Days 1, 4, 8, 11 (Cycle 2 and subsequent cycles); (3) dexamethasone (20 or 40 mg) administered on Days 15, 16, 18, 19, 22, 23, 25 and 26 (Cycle 1) and on Days 1, 2, 4, 5, 8, 9, 11 and 12 (Cycle 2 and subsequent cycles); and (4) rituximab (375 mg/m$^2$) administered by slow intravenous infusion, e.g., over 90 minutes, on Day 25 (Cycle 1) and on Day 11 (Cycle 2 and subsequent cycles).

When the anti-CXCR4 antibody is used in combination therapy with other anti-WM agents, these agents are typically used at their approved or standard dosages. For example, an exemplary dosage regimen with ibrutinib comprises dosing at 420 mg (three 140-mg capsules) orally once a day until unacceptable toxicity or disease progression.

In another embodiment, the dose of the anti-CXCR4 antibody is a flat-fixed dose that is fixed irrespective of the weight of the patient. For example, the anti-CXCR4 antibody may be administered at a fixed dose of 5, 20, 35, 75, 200, 350, 750 or 1500 mg, without regard to the patient's weight. As used herein, the terms "fixed dose", "flat dose" and "flat-fixed dose" are used interchangeably and refer to a dose that is administered to a patient without regard to the weight or body surface area (BSA) of the patient. The fixed or flat dose is therefore not provided as a mg/kg dose, but rather as an absolute amount of the agent (e.g., the anti-CXCR4 antibody).

Treatment of C1013G/CXCR4-Associated Waldenström's Macroglobulinemia Comprising a Patient Selection Step The C1013G/CXCR4 mutation is shown herein to be an activating mutation in WM (Example 3). Notwithstanding the more aggressive phenotype of C1013G/CXCR4-mutated cells compared to wild-type WM cells, BMS-936564 was found to be equally active in targeting adhesion, migration and proliferative properties of CXCR4-mutated cells (Example 5). Thus, anti-CXCR4 antibodies of this disclosure may have particular applicability in treating C1013G/CXCR4-associated WM, and the therapeutic regimen may include a step for identifying patients who carry the C1013G mutation. Accordingly, in one aspect, this disclosure provides a method for treating a subject afflicted with C1013G/CXCR4-associated WM comprising (a) selecting a subject that is a suitable candidate for treatment, the selecting comprising: (i) providing a test tissue sample obtained from WM tissue in the subject; (ii) assessing whether cells in the WM test tissue sample carry the C1013G mutation in the CXCR4 gene; and (iii) selecting the subject as a suitable candidate based on a determination that the WM cells carry the C1013G mutation in the CXCR4 gene; and (b) administering to the selected subject a therapeutically effective amount of an antibody of the disclosure or an antigen-binding portion thereof that specifically binds to a CXCR4 receptor expressed on the surface of a C1013G/CXCR4-associated WM cell. In certain embodiments of the present methods, the anti-CXCR4 antibody is administered in combination with an anti-WM agent, e.g., bortezomib or carfilzomib, that is also effective in treating WM patients harboring the C1013G/CXCR4 somatic variant. In any of the present methods, a test tissue sample comprises a biopsy sample of tumor tissue or a sample of tumor cells found in the periphery.

This disclosure also provides a method for treating a subject afflicted with C1013G/CXCR4-associated WM comprising administering to the subject a therapeutically effective amount of an antibody of the disclosure or an antigen-binding portion thereof that specifically binds to a CXCR4 receptor expressed on the surface of a C1013G/CXCR4-associated WM cell, the subject having been selected on the basis that the WM cells of the subject are determined to carry the C1013G mutation in the CXCR4 gene.

This disclosure further provides a method for selecting a WM patient for treatment with an antibody of the disclosure or an antigen-binding portion thereof that specifically binds to a CXCR4 receptor expressed on the surface of a WM cell, which method comprises: (a) optionally providing a test tissue sample obtained from WM tissue in the patient; (b) assessing whether cells in the WM test tissue sample carry the C1013G mutation in the CXCR4 gene; and (c) selecting the patient for treatment based on a determination that the WM cells carry the C1013G mutation in the CXCR4 gene.

In another aspect, this disclosure provides a method for determining a therapeutic regimen comprising an anti-CXCR4 antibody of the disclosure or an antigen-binding portion thereof for treating C1013G/CXCR4-associated WM in a subject, which method comprises: (a) optionally providing a test tissue sample obtained from WM tissue in the subject; (b) assessing whether cells in the WM test tissue sample carry the C1013G mutation in the CXCR4 gene; and (c) determining the therapeutic regimen based on the determination that the WM cells carry the C1013G mutation.

In certain embodiments of the present methods, the C1013G mutation is detected by a polymerase chain reaction (PCR) assay, a reverse transcriptase-polymerase chain reaction (RT-PCR) assay, a nucleic acid hybridization assay, or by DNA sequencing. In further embodiments, the PCR assay is a real-time allele-specific PCR (AS-PCR) assay. In further embodiments, the DNA sequencing is whole genome DNA sequencing.

In any of the disclosed methods comprising screening for the C1013G/CXCR4 mutation in a test tissue sample, it should be understood that the step comprising the provision of a test tissue sample from a patient is an optional step. That is, in certain embodiments the method includes this step, and in other embodiments, this step is not included in the method. It should also be understood that in certain embodiments the "assessing" step to determine whether cells in the WM test tissue sample carry the C1013G mutation is performed by a transformative method of assaying for the presence of the mutation, for example by performing a polymerase chain reaction (PCR) assay. In other embodiments, no transformative step is involved and the presence of the mutation is assessed by, for example, reviewing a report of test results from a laboratory. In certain embodiments, the steps of the methods up to, and including, assessing whether the cells carry the C1013G/CXCR4 mutation provides an intermediate result that may be provided to a physician or other medical practitioner for use in selecting a suitable candidate for therapy and/or administering a therapeutic agent(s) to the patient. In certain embodiments, the steps that provide the intermediate result may be performed by a medical practitioner or someone acting under the direction of a medical practitioner. In other embodiments, these steps are performed by an independent laboratory or by an independent person such as a laboratory technician.

Another aspect of this disclosure relates to a therapeutic regimen for treating a patient afflicted with C1013G/CXCR4-associated WM, which regimen is determined by the method described above comprising (a) optionally providing a test tissue sample obtained from WM tissue in the subject; (b) assessing whether cells in the WM test tissue sample carry the C1013G mutation in the CXCR4 gene; and (c) determining the therapeutic regimen based on the determination that the WM cells carry the C1013G mutation. In certain embodiments, the therapeutic regimen comprises administering the anti-CXCR4 antibody of the disclosure or antigen-binding portion thereof to the patient at: (a) a dose of at least twice, at least three times, or at least five times, the dose administered in treating a WM patient carrying the wild-type CXCR4 gene; and/or (b) a frequency at least two times, at least three times, or at least five times higher than the frequency administered in treating a WM patient carrying the wild-type CXCR4 gene.

Preferred Anti-CXCR4 Antibodies for Treating Waldenström's Macroglobulinemia

The therapeutic methods disclosed herein comprise administering to a WM patient an anti-CXCR4 antibody of the disclosure. This antibody binds specifically to wild-type CXCR4 or the C1013G/CXCR4 variant expressed on a WM cell surface, end exhibits certain structural and functional properties that are beneficial to therapeutic efficacy. For example, a desirable structural characteristic is that the antibody comprises the CDRs or variable regions of F7 (ulocuplumab), F9, D1 or E2 (as identified in WO 2008/060367), or cross-competes with any of these antibodies for binding to the same epitope region of CXCR4. Desirable functional characteristics include high-affinity binding to human CXCR4 expressed on a cell surface, inhibiting $CXCR4^+$ tumor cell proliferation and/or inducing $CXCR4^+$ tumor cell apoptosis in vivo. In certain preferred embodiments of the disclosed therapeutic methods, the anti-CXCR4 antibody or portion thereof comprises the CDR1, CDR2 and CDR3 domains in a heavy chain variable region comprising consecutively linked amino acids, the sequence of which is set forth in SEQ ID NO: 25, and the CDR1, CDR2 and CDR3 domains in a light chain variable region comprising consecutively linked amino acids, the sequence of which is set forth in SEQ ID NO: 29.

In other preferred embodiments, the anti-CXCR4 antibody or portion thereof comprises a heavy chain variable region comprising consecutively linked amino acids, the sequence of which is set forth in SEQ ID NO: 25, and a light chain variable region comprising consecutively linked amino acids, the sequence of which is set forth in SEQ ID NO: 29.

In yet other preferred embodiments, according to an delineation of CDR sequences by the Kabat system (Kabat et al., 1991; Johnson and Wu, 2000), the anti-CXCR4 antibody or portion thereof comprises a heavy chain variable region CDR1 comprising consecutively linked amino acids having the sequence set forth in SEQ ID NO: 1, a heavy chain variable region CDR2 comprising consecutively linked amino acids having the sequence set forth in SEQ ID NO: 5, a heavy chain variable region CDR3 comprising consecutively linked amino acids having the sequence set forth in SEQ ID NO: 9, a light chain variable region CDR1 comprising consecutively linked amino acids having the sequence set forth in SEQ ID NO: 13, a light chain variable region CDR2 comprising consecutively linked amino acids having the sequence set forth in SEQ ID NO: 17, and a light chain variable region CDR3 comprising consecutively linked amino acids having the sequence set forth in SEQ ID NO: 21. In more preferred embodiments, the antibody or fragment thereof is ulocuplumab or a CXCR4-binding fragment thereof.

One aspect of the disclosed invention is the use of an anti-CXCR4 antibody of the disclosure or antigen-binding portion thereof for the preparation of a medicament for treating a subject afflicted with WM or C1013G/CXCR4-associated WM. This disclosure an anti-CXCR4 antibody of the disclosure or antigen-binding portion thereof for use in treating a subject afflicted with WM or C1013G CXCR4-associated WM.

Therapeutic Kits

Also within the scope of the present disclosure are kits comprising an anti-CXCR4 antibody of antigen-binding fragment or composition thereof and instructions for use, e.g., instructions comprising administration schedules to allow a medical practitioner or patient to administer the antibody or composition thereof to a WM patient. Accordingly, this disclosure provides a kit for treating C1013G/CXCR4-associated WM in a subject, the kit comprising (a) one or more doses of any of an anti-CXCR4 antibody of the disclosure or an antigen-binding portion thereof and (b) instructions for using the anti-CXCR4 antibody or fragment thereof in any of the therapeutic methods described herein. For example, in certain embodiments the anti-CXCR4 antibody or antigen-binding portion thereof in the kit comprises the CDR1, CDR2 and CDR3 domains in a heavy chain variable region having the amino acid sequence set forth in SEQ ID NO: 25, and the CDR1, CDR2 and CDR3 domains in a light chain variable region having the amino acid sequence set forth in SEQ ID NO: 29. In preferred embodiments, the anti-CXCR4 antibody is ulocuplumab. Optionally, the kit includes multiple packages of the single-dose pharmaceutical compositions each containing an effective amount of the anti-CXCR4 antibody for a single administration in accordance with the methods described herein. The kit can further contain one or more additional therapeutic reagents as described herein, such as a chemotherapeutic or radiotoxic agent, or one or more additional antibodies that target different antigens. In certain embodiments, the anti-CXCR4 antibody is co-packaged with one or more other therapeutic agents in unit dosage form.

Instruments or devices necessary for administering the pharmaceutical composition(s) also may be included in the kits. For instance, a kit may contain one or more syringes. In certain embodiments, the one or more syringes are pre-filled with an amount of the anti-CXCR4 antibody. Kits also typically include a label indicating the intended use of the contents of the kit, along with the instructions for use. The term label includes any writing, or recorded material supplied on or with the kit, or which otherwise accompanies the kit.

The present invention is further illustrated by the following examples, which are merely illustrative and should not be construed as limiting the scope of this disclosure in any way as many variations and equivalents will become apparent to those skilled in the art upon reading the present disclosure. The contents of all figures and all references, GenBank entries, patents and published patent applications cited throughout this application are expressly incorporated herein by reference.

Example 1

Screening of Patients with B-Cell Lymphoproliferative Disorders for C1013/CXCR4 Mutation Patients with Different B-Cell Lymphoproliferative Disorders were Screened for the Presence of the C1013/CXCR4 Variant.

Clinical Samples

Tumor samples were collected from 418 patients with different B-cell lymphoproliferative disorders (B-LPDs), distributed as follows: WM (n=131); IgM MGUS (n=40); diffuse large B-cell lymphoma (n=75); splenic marginal zone lymphoma (n=14); B-cell chronic lymphocytic lymphoma (n=37, including 16 with M-component); hairy cell leukemia (n=35); MM (n=36, 3 of IgM isotype); IgA/IgG MGUS (n=22); lymphoplasmacytic lymphoma with no WM criteria (n=13); amyloidosis (n=6); and B-LPD not otherwise specified (n=9). Diagnosis was made according to the latest WHO classification of tumors of hematopoietic and lymphoid tissues (Campo et al., 2011). Thirty-two healthy volunteers were also included in the study as controls.

Immunophenotypic Analysis and Clonal Cell Quantification in Diagnostic Tissues

Immunophenotypic evaluation was done conventionally using panels of monoclonal antibodies previously described (Paiva et al., 2013), and following the general recommendations of the EuroFlow group for the immunophenotypic evaluation of Hematological Malignancies (van Dongen et al., 2012). These cases were immunophenotyped using 4-color combinations that included up to 20 different antigens in addition to surface IgM (sIgM) and cytoplasmic Ig lambda and Kappa (cyIgλ and cyIgκ). The percentage of clonal cells was counted with the tube including the sIgM/CD25/CD19/CD38 MoAb. Data acquisition was performed in a FACSCalibur flow cytometer (Becton Dickinson Biosciences [BDB] San Jose, Calif.) using the FACSDiva software (version 6.1; BDB) and a two-step acquisition procedure for total and CD19+-only events. Data analysis was performed using the Infinicyt software (Cytognos; Salamanca, Spain). After immunophenotypic analysis and clonal cell quantification in diagnostic tissues, detection of the C1013G/CXCR4 variant was performed using real-time allele specific PCR (AS-PCR). Ten cases of extramedullary WM were also included in these studies. Approval was obtained from the Dana-Farber Cancer Institute and the University Hospital of Salamanca Institutional Review Boards for these studies. Informed consent was provided according to the Declaration of Helsinki.

Real-Time AS-PCR for Identification of CXCR4 C1013G Mutation

A real-time AS-PCR assay was developed based on the use of two reverse primers differing in the two last nucleotides (at 3' position) so that each primer is specific to either the wild-type or the mutated allele, as described (Paiva et al., 2013). In order to prevent the amplification of the non-matching primer (thereby increasing specificity), an additional nucleotide mismatch (C>G) was introduced next to the mutated nucleotide. The specific length and position of the primers were calculated with the Oligo 6.0 software (Molecular Biology Insights, Cascade, Colo.). Reverse primers were: 5'-GACTCAGACTCAGTGGAAACAGATG-3' (reverse wild-type primer) and 5'-GACTCAGACTCAGTGGAAACAGAAC-3' (reverse mutated primer). The common forward primer was 5'-TTTCTTCCACTGTTGTCTGAACC-3', to generate a 165 bp PCR product. In addition, a specific TaqMan® probe was designed using the Primer Express® Software v3.0.1 (Applied Biosystems, Foster City, Calif., USA), that yielded the following reporter, sequence and quencher: 6FAM:5'-TATGCTTTCCTTGGAGCCA-3':NFQ-MGB.

For real-time AS-PCR development, each experiment required two different PCR reactions: one for the detection of the CXCR4 C1013G mutation (with the mutated reverse primer) and the other one as a control of the DNA quality (using the wild-type reverse primer). Each reaction was carried out in a final volume of 20 al, containing 300 nM of each primer, 200 nM of the probe, 1× of the TaqMan® Universal PCR Master Mix (Applied Biosystems, Foster City, Calif., USA) and 20 ng of genomic DNA. Experiments were performed in a StepOnePlus® Real-Time PCR System (Applied Biosystems) and consisted of an initial denaturation step of 10 min at 95° C., followed by 50 cycles of 95° C. for 15 s and 60° C. for 60 s. Data were analyzed with StepOne™ Software v2.1 (Applied Biosystems), which provides a CT value that was considered as the cycle in which the fluorescence begins to be distinguished from the background.

Results

C1013G/CXCR4 Variant Occurs in Patients with WM

The C1013G/CXCR4 mutation was detected in 28.2% of the WM patients (37/131) and in 20% IgM-MGUS patients (8/40). See Table 1. In addition, the variant was detected in 7% of patients with splenic marginal zone lymphoma (1/14) and 1.3% of patients with diffuse large B-cell lymphoma (1/75), whereas it was absent in B-cell chronic lymphocytic leukemia, hairy cell leukemia, MM and IgG/IgA MGUS (Table 1), suggesting a potential role of this variant in supporting the molecular pathogenesis of WM as well as of the IgM-MGUS precursor stage. The C1013G/CXCR4 variant results in a single nucleotide change C→G in CXCR4, leading to a predicted stop codon in place of a serine at amino acid position 338 (S338X). This has been previously linked to truncation of the C-terminal domain of the CXCR4 (Alapi K et al., 2007), resulting in its impaired intracellular translocation.

Figure 2B:
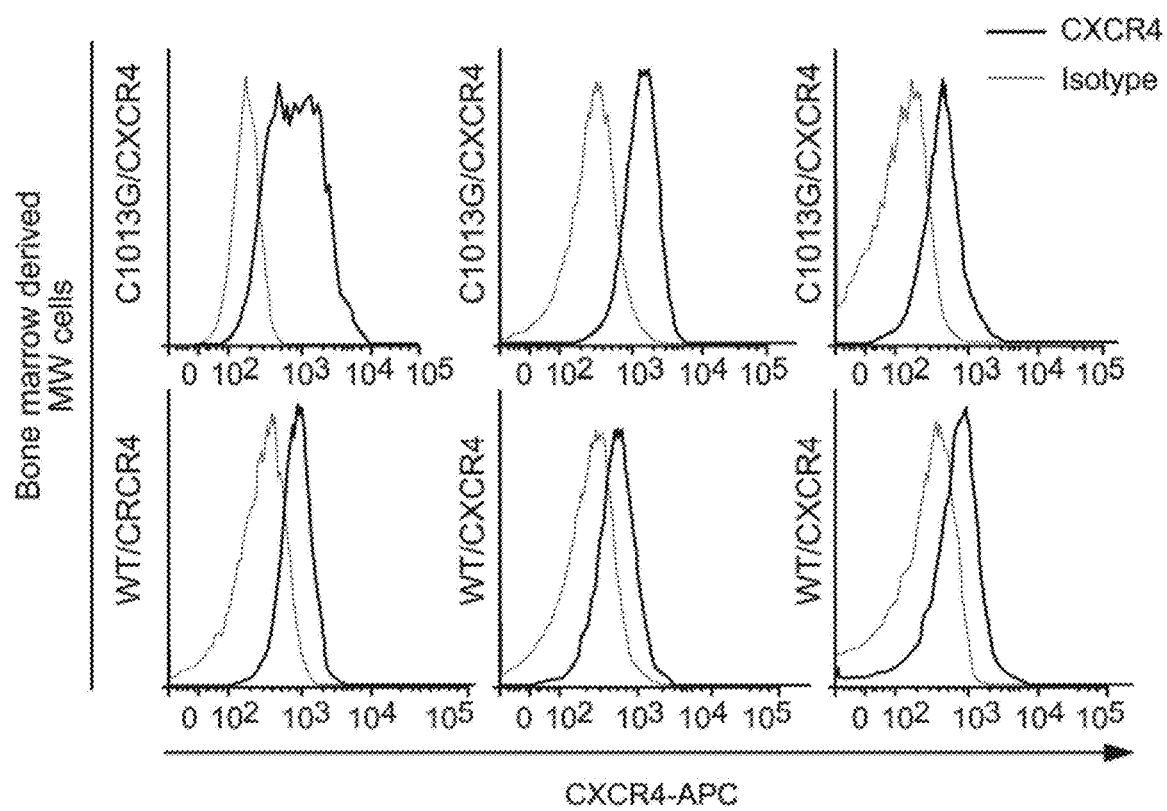

To further prove that the observed variant may indeed induce CXCR4 changes on the surface of WM cells, the CXCR4 surface expression on independent primary WM patient BM-derived CD191 cells was evaluated, either carrying the variant (n=3) or not (n=8), and higher surface expression was found in patients harboring the C1013G/CXCR4 variant compared with wild-type/CXCR4 patients (FIG. 2). Moreover, 10 patients with confirmed extramedullary WM histological diagnosis were also evaluated for the presence of the somatic variant: patients with lung (3/3) and kidney (1/1) involvement presented with mutated C1013G/CXCR4, but this mutation was absent in small bowel (2/2) and soft tissues (4/4), as detected by AS-PCR on genomic DNA (Table 2), indicating that this mutation may be more prevalent in patients with extramedullary involvement.

TABLE 1

Waldenström's macroglobulinemia patients present with C1013G/CXCR4 somatic mutation

| Patient | No. of patients screened (N = 418) | C1013G/CXCR4 Number | % |
|---|---|---|---|
| Waldenström's macroglobulinemia | 131 | 37 | 28.2 |
| IgM MGUS | 40 | 8 | 20 |
| Diffuse large cell lymphoma | 75 | 1 | 1.3 |
| Splenic marginal zone Lymphoma | 14 | 1 | 7 |
| B-CLL (16 with monoclonal component) | 37 | 0 | 0 |
| Hairy cell leukemia | 35 | 0 | 0 |
| Multiple myeloma (3 with IgM) | 36 | 0 | 0 |
| IgA/IgG MGUS | 22 | 0 | 0 |
| Lymphoplasmacytic lymphoma (with no WM criteria) | 13 | 0 | 0 |
| Amyloidosis | 6 | 0 | 0 |
| B-cell chronic lymphoproliferative disorder, NOS | 9 | 0 | 0 |
| Healthy volunteers | 32 | 0 | 0 |

C1013G/CXCR4 variant occurs in 28% of patients with WM, being either absent or present in a minority of patient with B-cell lymphoproliferative disorders.

B-CLL, B-cell chronic lymphocytic leukemia; MGUS, monoclonal gammopathy of undetermined significance; NOS, not otherwise specified.

TABLE 2

C1013G/CXCR4 variant is present in lung and kidney tissues of patients with extramedullary WM disease

|  | C1013G/CXCR4 | Wild type CXCR4 |
|---|---|---|
| Lung (n = 3) | 3/3 | 0 |
| Kidney (n = 1) | 1/1 | 0 |
| Small bowel (n = 2) | 0 | 2/2 |
| Soft tissues (n = 4) | 0 | 4/4 |

Example 2

Effect of CXCR4 Over-Expression on WM Cell Growth and Dissemination

In order to dissect the in vivo functional relevance of the C1013G/CXCR4 variant in supporting WM biology, CXCR4 (GFP$^+$)-over-expressing WM cells (CXCR4$^+$) were first to provide insight into the role of CXCR4 in WM in vivo.

Immunohistochemistry

Murine tissues (BM, liver, kidney, lung and lymph nodes) were analyzed and quantified for the expression of human CD20 and human CXCR4. These tissues were fixed in formalin 10%, ethanol 70% was used as storage solution; and embedded in paraffin. Paraffin sections were incubated with anti-human-CXCR4 (Abcam, Cambridge, Mass.), and anti-human-CD20 (Dako, Carpinteria, Calif.) monoclonal antibodies, using the Leica Bond III automated staining platform (Leica Biosystems, Buffalo Grove, Ill.). Secondary antibody was provided as part of the Bond III Refine Detection Kit (Leica Biosystems) and sections were incubated with a diaminobenzidine (DAB)-peroxidase substrate provided in the Bond III Refine Detection Kit, counterstained with hematoxylin-eosin, dehydrated, mounted and digitally photographed (Nikon Eclipse 80i, Nikon, Melville, N.Y.). Quantification of CD20 and CXCR4 staining was performed using NIS Elements software (Nikon, Melville, N.Y.).

Tissue Immunofluorescence

Tissue immunofluorescence imaging was performed for the evaluation of GFP$^+$/CXCR4 over-expressing WM cells or RFP$^+$/scramble WM cells on femurs, liver and kidneys harvested from mice, as described (Hsieh et al., 2012). Cells of interest were either BCWM.1-GFP+ or BCWM.1-RFP+. Nuclear stain DAPI was added to each slide. Slides were analyzed using a fluorescence microscope (Nikon Eclipse 80i; objective 40× plan fluor 0.75NA). MM.1S-GFP+ cells were counted from 4 separate fields per slide. Images were taken using the Hamamatsu OrcaER camera and the NISElement software. Image J was used to merge the two different channels.

ELISA

Human serum IgM levels were determined by using a human IgM ELISA assay (ZeptoMetrix, Buffalo, N.Y.), according to the manufacturer's protocol.

In Vitro Cell Adhesion, Migration and Proliferation Studies

Adhesion of WM cells to primary WM BM-MSCs was evaluated by an in vitro adhesion assay using calcein AM-labeled MM cells. The degree of fluorescence was measured using a spectrophotometer (485-520), as previously described (Roccaro et al., 2010). Adhesion of WM cells to fibronectin was evaluated by using an in vitro adhesion assay to fibronectin, following the manufacturer's recommendations (EMD Biosciences, San Diego, Calif.), as described (Roccaro et al., 2013). Migration of WM cell lines was evaluated towards either SDF-1α or primary WM BM-MSCs using transwell migration plates (Corning Life Sciences, Tewksbury, Mass.) as previously described (Roccaro et al., 2010; Sacco et al., 2011; Azab et al., 2012). WM cell proliferation was assessed by evaluating DNA synthesis, measured by [$^3$H]-thymidine ([$^3$H]-TdR; Perkin Elmer, Boston, Mass.) uptake, after 48 h of coculture with primary BM-MSCs as previously described (Roccaro et al., 2010; Sacco et al., 2011; Azab et al., 2012). Cell toxicity was evaluated by measuring 3-(4,5-dimethylthiazol-2-yl)-2,5-diphenyltetrazolium bromide (Chemicon International, Temecula, Calif.), as described (Roccaro et al., 2010; Sacco et al., 2011; Azab et al., 2012).

Loss- and Gain-of Function Studies

CXCR4 gain- or loss-of-function studies have been performed using WM cell lines (BCWM.1; MWCL1) either alone or in the context of primary WM BM-MSCs, as previously described (Roccaro et al., 2010; Sacco et al., 2011). Briefly, CXCR4 was knocked-down in WM cells using short hairpin RNAs (shRNAs); clones 171, 649) and lentivirus-mediated infection; scramble probe was used as a control containing the target sequence (clones 171, 649) or scramble control, according to manufacturer's specifications (Thermo Scientific, Waltham, Mass.). Transduction efficiency was verified by quantitative reverse transcription PCR (qRT-PCR) and by evaluating the detection of GFP expressing cells using a fluorescence microscope (Nikon Eclipse 80i, Nikon, Melville, N.Y.).

Over-expression of CXCR4 was obtained in WM cells using either precision LentiORF/CXCR4/GFP (CXCR4$^+$) or scramble probe/RFP used as control (Thermo Scientific). Over-expression efficiency was confirmed by qRT-PCR and by detecting GFP- and RFP-expressing cells with a fluorescence microscope (Nikon Eclipse 80i, Nikon, Melville, N.Y.).

Statistics

Certain of the statistical methods described are also used in other Examples. P values provided for the in vitro assays are based on T-tests (two-tailed; $\alpha$ 0.05) or on ANOVA. P values are provided for each figure. Drug synergism was analyzed by isobologram analysis using the CalcuSyn software program (Biosoft, Ferguson, Mo.), as described 25-27. Kaplan-Meier curves were obtained using GraphPad Prism and P value was calculated based on log-rank test (Roccaro et al., 2010; Sacco et al., 2011; Roccaro et al., 2008).

Results

Functional Relevance of CXCR4 in WM In Vivo

Figure 3:
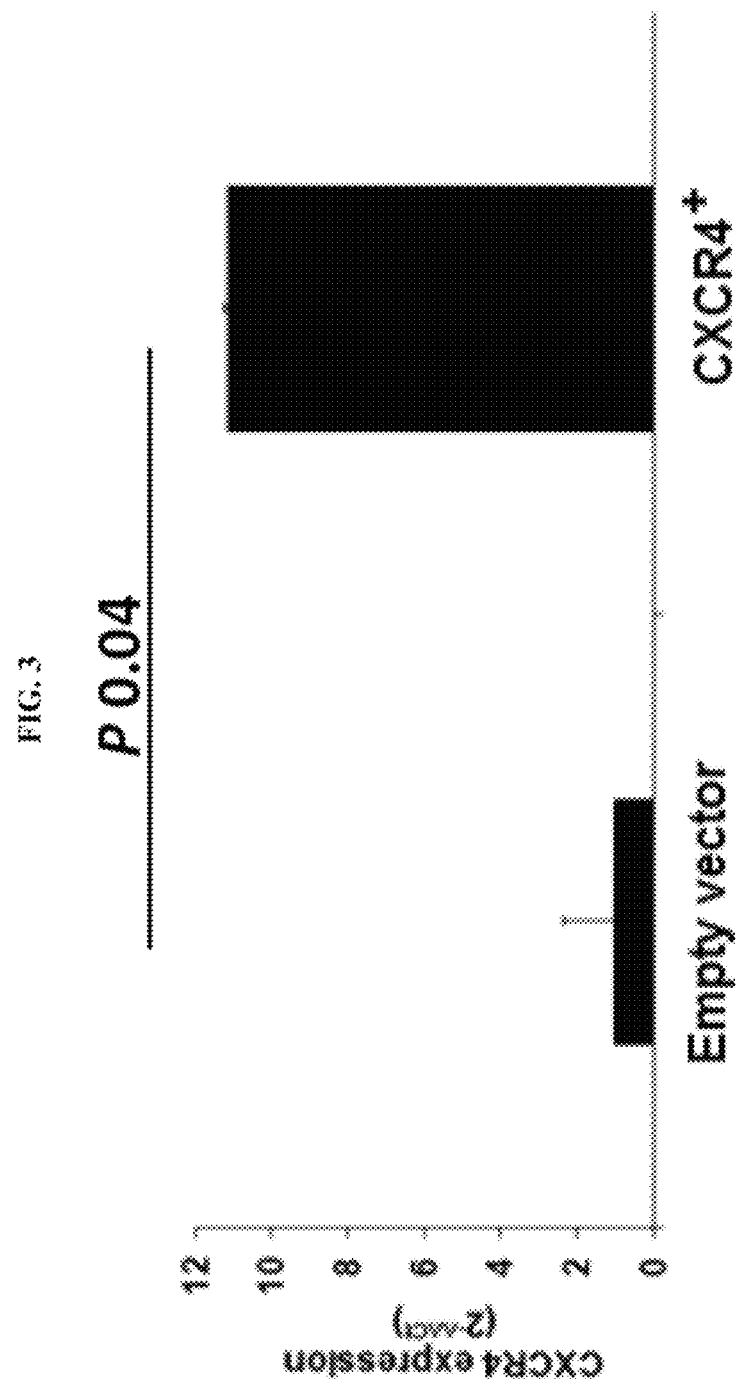
FIG. 3 shows the efficiency of CXCR4 over-expression in WM cells. BCWM.1 cells were infected with either precision LentiORF/CXCR4/GFP (CXCR4$^+$) or with an empty vector/RFP control. Human CXCR4 expression levels were evaluated by qRT-PCR, using the ΔΔCt method, with normalization to GAPDH. P indicates P value.
Figure 4B:
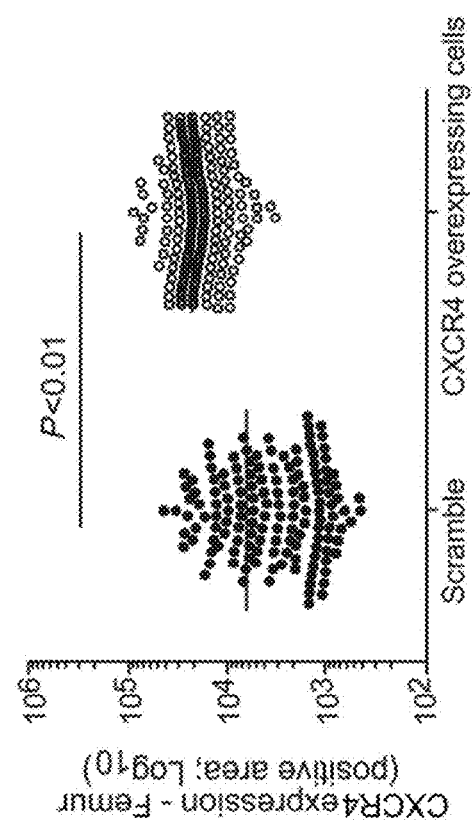
FIGS. 4A-4H.
Figure 4A:
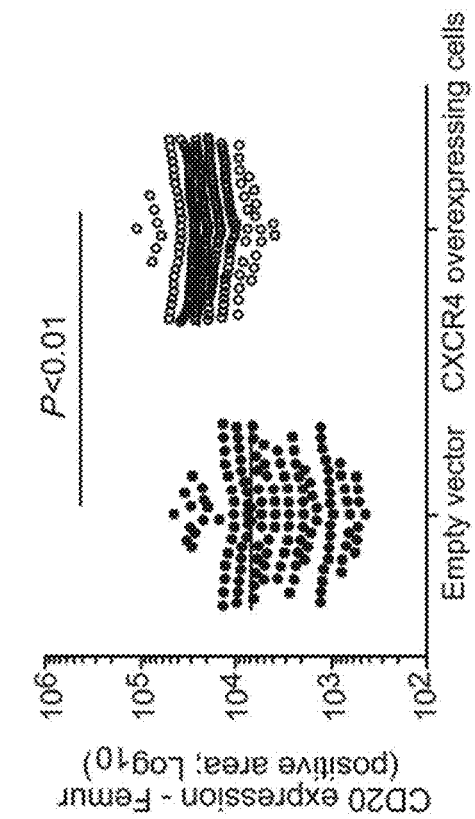
Figure 4D:
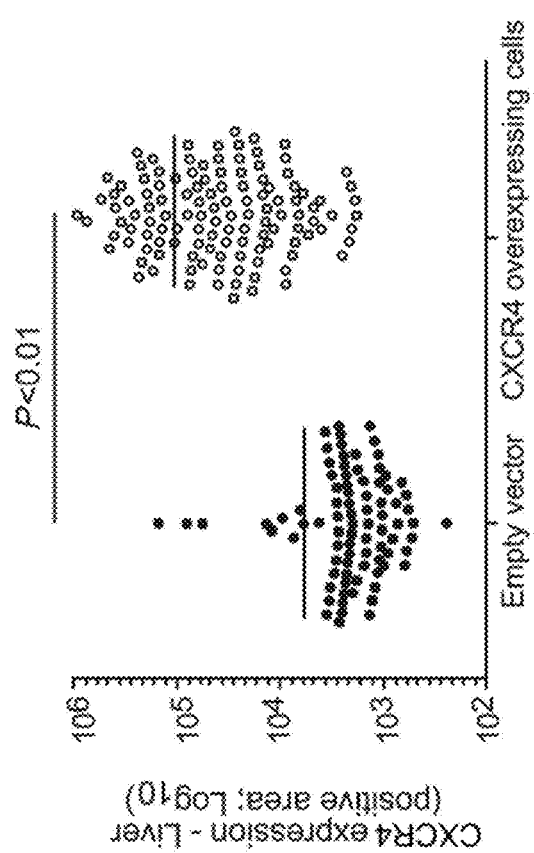
Figure 4C:
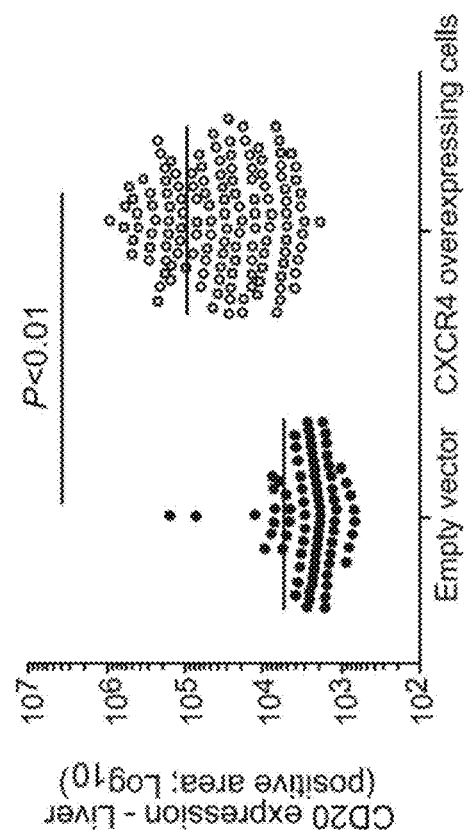
Figure 4F:
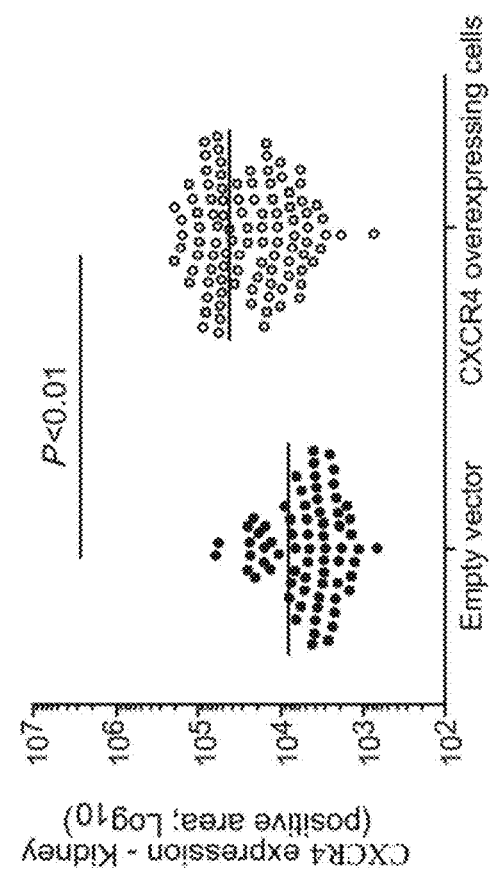
Figure 4E:
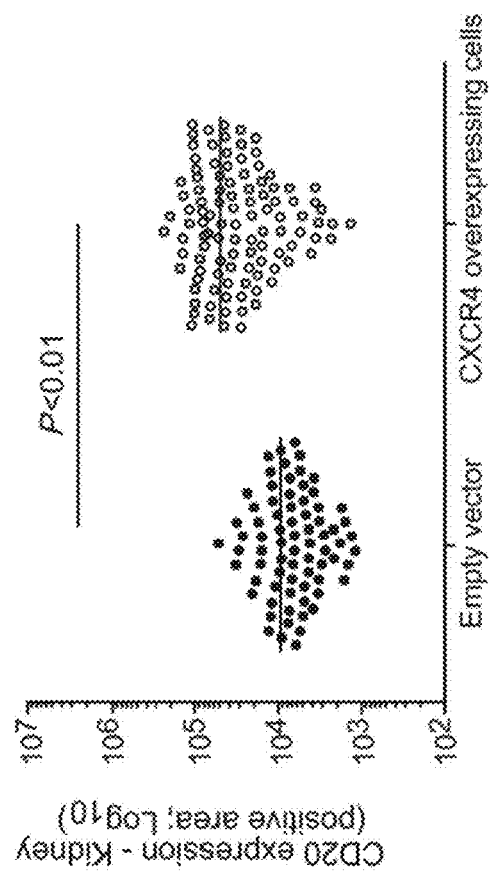
Figure 4G:
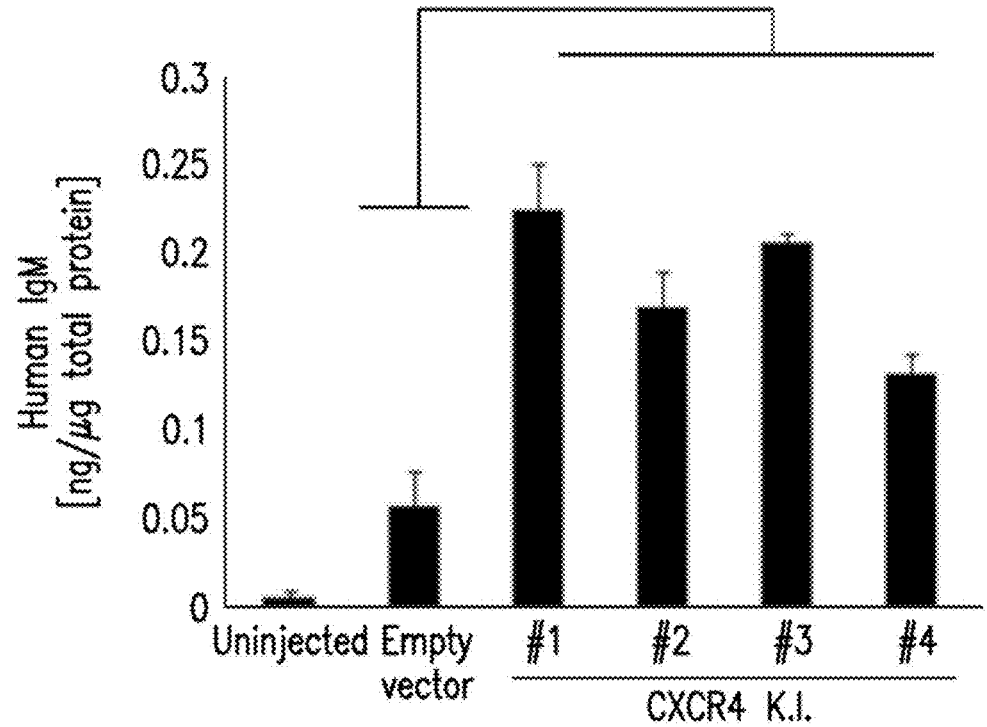
Figure 4H:
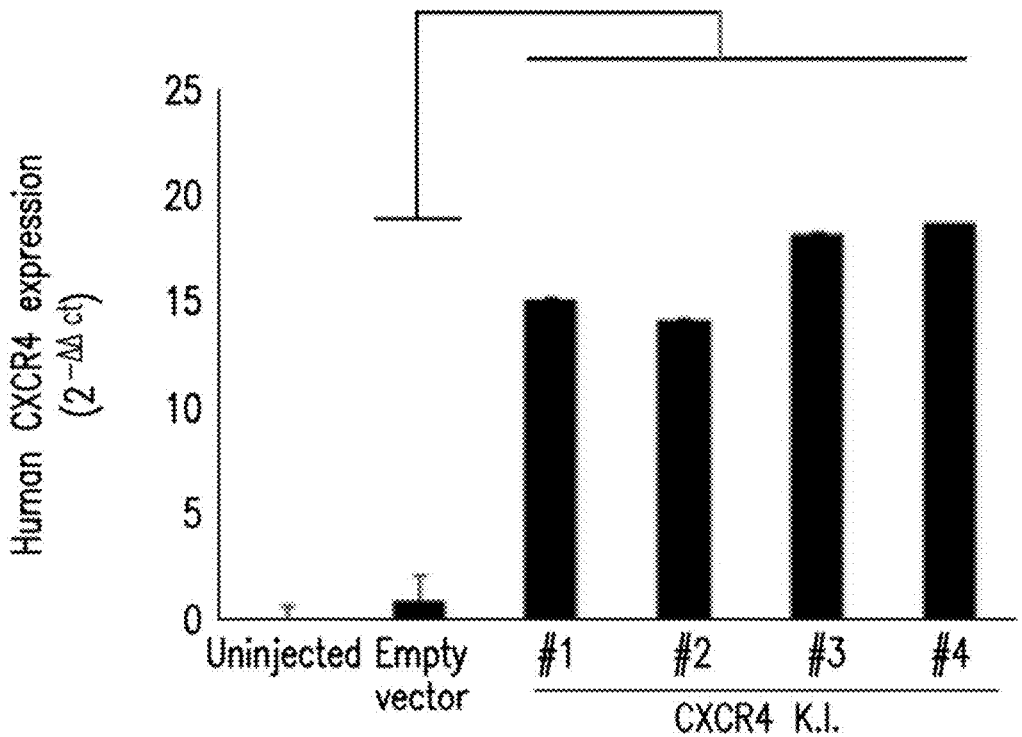

Both CXCR4$^+$/GFP$^+$ cells and empty vector/RFP$^+$ cells were injected into SCID/Bg mice. The efficiency of the infection was confirmed by qRT-PCR (FIG. 3) and immunofluorescence imaging (data not shown; Roccaro et al., 2014). Both CXCR4$^+$/GFP$^+$ cells and empty vector/RFP$^+$ cells were injected into SCID/Bg mice. Because of disease progression, mice were euthanized after 3 weeks, demonstrating that the over-expression of CXCR4 in WM cells led to a more aggressive phenotype as evidenced by a significantly higher involvement of organs in CXCR4$^+$ cell-injected mice compared to empty vector cell-injected mice (P<0.01; FIGS. 4 A-C).

Figure 5D:
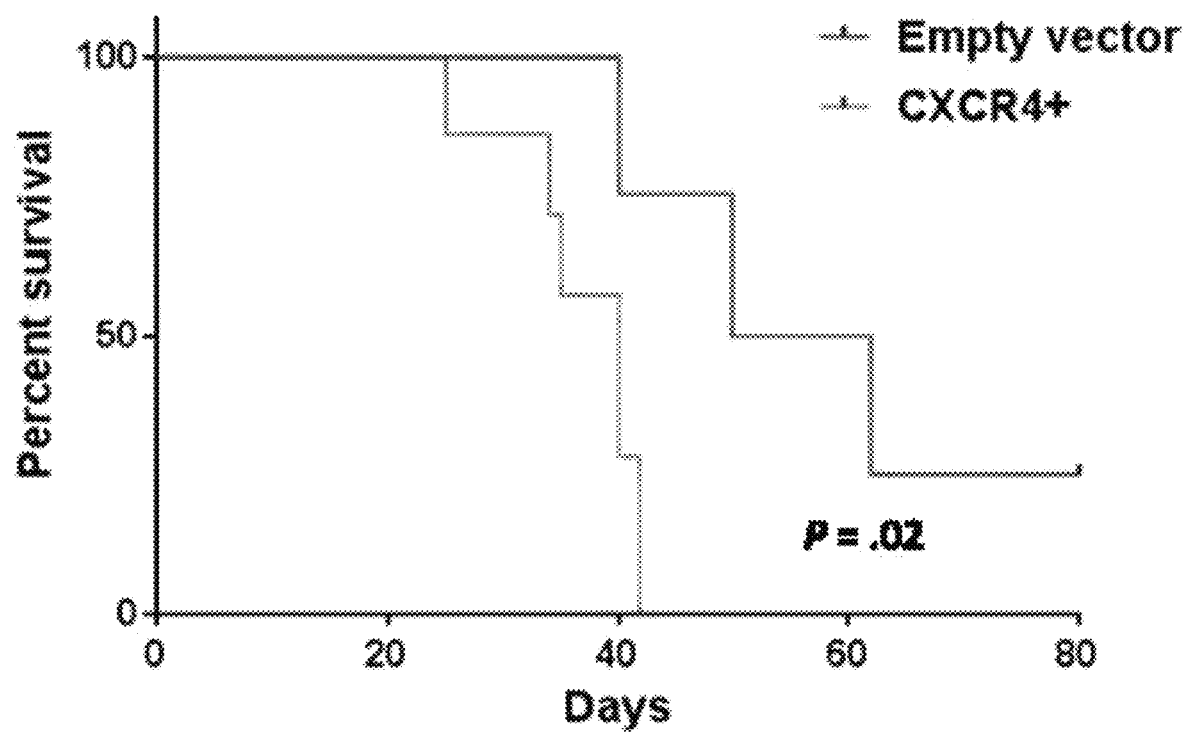

Ex vivo studies demonstrated that CXCR4$^+$ WM cells disseminated and proliferated more rapidly in the BM and other organs including liver and kidneys (FIG. 4; FIGS. 5A-C). These findings were also confirmed by immunofluorescence imaging, showing higher infiltration of GFP$^+$ compared to RFP$^+$ cells, representative of CXCR4$^+$ and empty vector infected cells, respectively (data not shown; Roccaro et al., 2014). Importantly, reduced survival was observed in CXCR4$^+$ cell-harboring mice compared to empty vector cell-injected ones (P=0.02; FIG. 5D). In addition, CXCR4$^+$ cell-injected mice presented with an increased serum IgM secretion, compared to either uninjected or empty vector cell-injected mice (P=0.02; FIG. 4D). The presence of CXCR4$^+$ cells ex vivo was also confirmed by performing qRTPCR on the BM cells harvested from the femurs of either CXCR4$^+$ cell- or empty vector-injected mice (FIG. 4E).

Figure 5E:
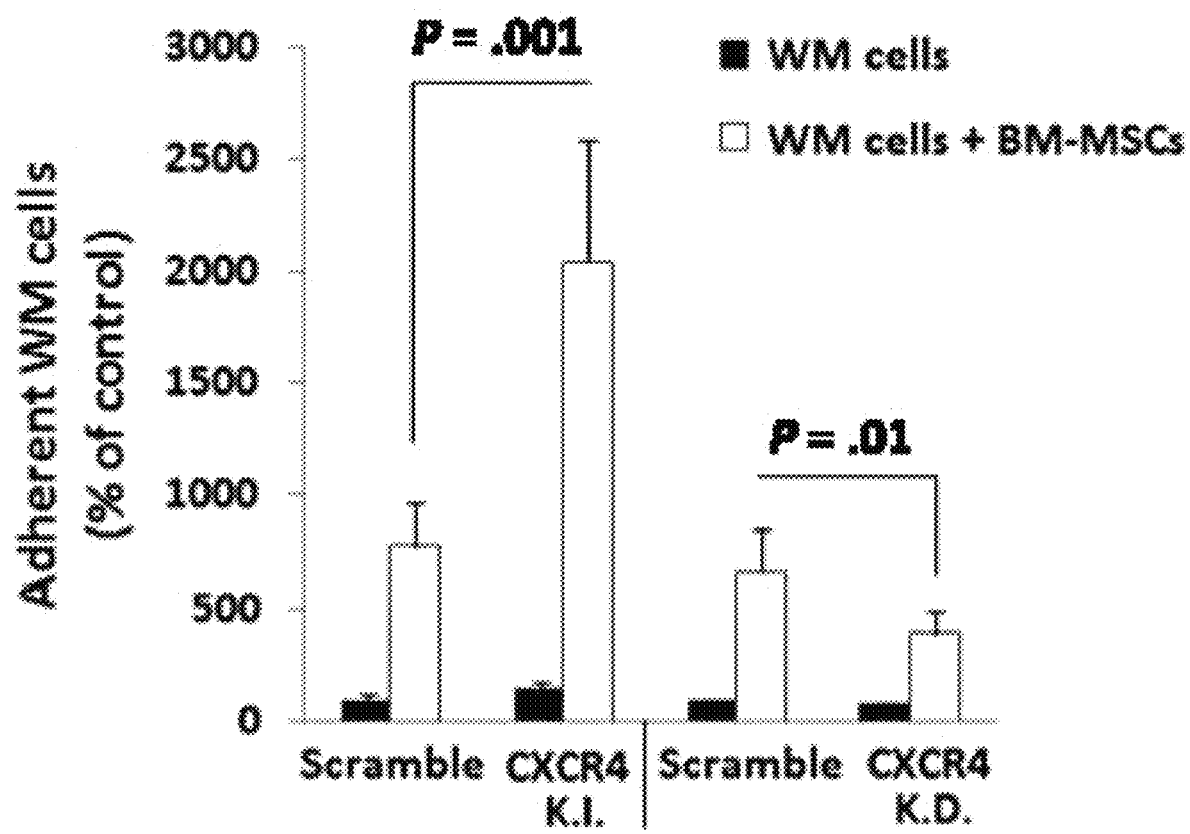
Figure 5F:
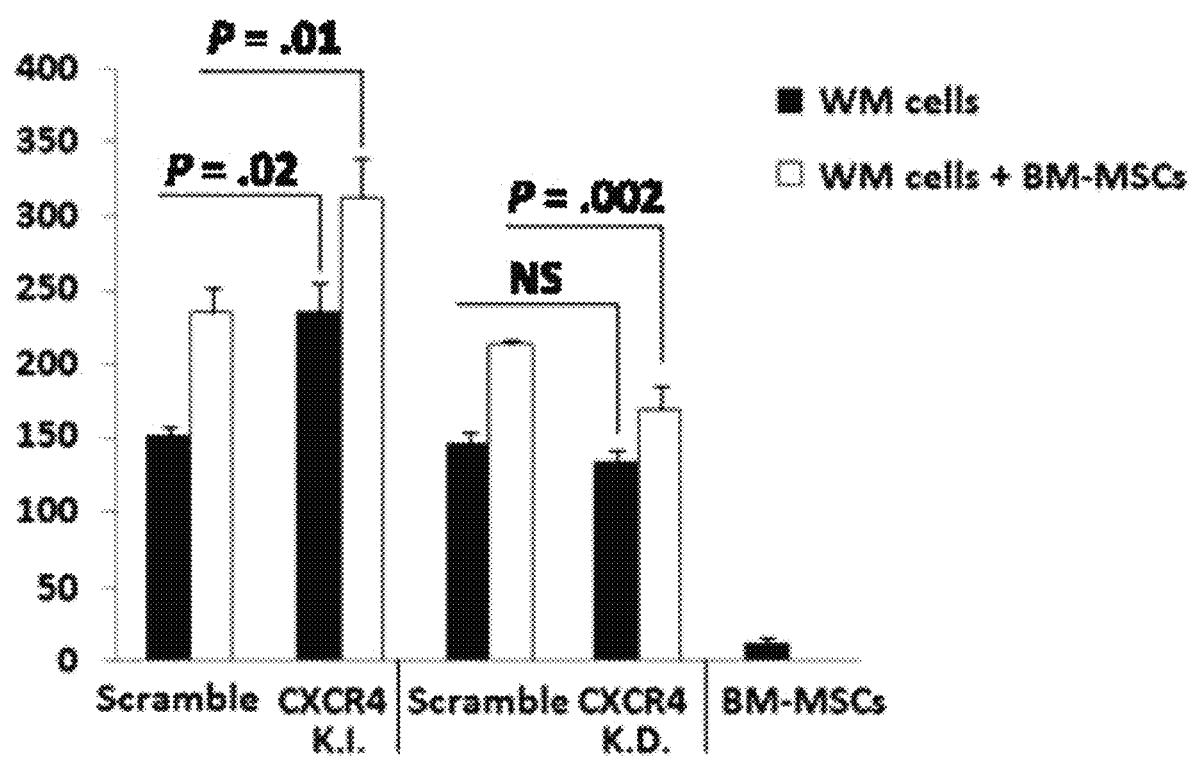
Figure 6:
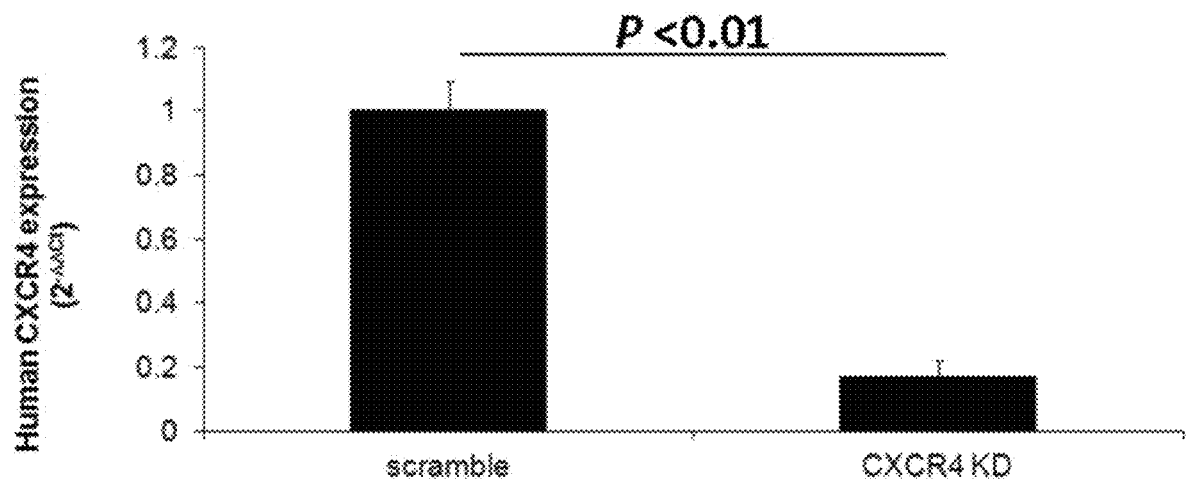
FIG. 6 shows the efficiency of CXCR4 knock-down in infected WM cells. BCWM.1 cells were infected with either CXCR4-shRNA/GFP (CXCR4 K.D.) or scramble probe/GFP as control. Human CXCR4 expression levels were evaluated by qRT-PCR, using the ΔΔCt method, with normalization to GAPDH. P indicates P value.

The in vitro sequelae due to CXCR4 gain of function in WM cells were delineated by comparing CXCR4$^+$ cells to CXCR4-knockdown cells. Efficiency of infection was confirmed at the mRNA level (FIG. 6) and by immunofluorescence imaging (data not shown; Roccaro et al., 2014). The ability of WM cells to adhere to primary WM BM stromal cells (BM-MSCs) and to proliferate when in the context of BM-MSCs was shown to be enhanced in CXCR4$^+$ WM cells, and inhibited in the case of CXCR4 knock-down WM cells (FIG. 5E, F). Similarly, CXCR4-overexpression led to increased adhesion capabilities of WM cells to fibronectin, as opposed to CXCR4-silenced cells that presented with inhibited WM cell adhesion to fibronectin (FIG. 7A, B). Taken together these findings indicate that CXCR4 is crucial in facilitating in vivo WM cell growth and dissemination.

Example 3

Effect of C1013G/CXCR4 Mutation on WM Pathogenesis

The question of whether the C1013G/CXCR4 variant actively supports WM pathogenesis, leading to disease progression, was elucidated.

C1013G/CXCR4 Mutagenesis

A C1013G/CXCR4 variant was generated in WM cell lines (BCWM.1; MWCL1) by site-directed mutagenesis using a QuickChange XL site-directed mutagenesis kit (Stratagene, Agilent Technologies, Santa Clara, Calif.), according to the manufacturer's instructions. Cells infected with a control vector were considered as control and are described herein as "control cells." Detection of the C1013G/CXCR4 variant in WM infected cells was evaluated by performing allele-specific PCR on either genomic DNA or cDNA isolated from infected cells. (Forward primer: 5'-TTTCTTCCACTGTTGTCTGAACC-3'; Reverse wild-type primer: 5'-GACTCAGACTCAGTGGAAACA-GATG-3'; Reverse mutated primer: 5'-GACTCA-GACTCAGTGGAAACAGAAC-3'). Data were further confirmed by DNA sequencing.

Gene Expression Studies

Gene expression profiling was performed on C1013GCXCR4-mutated BCWM.1 cells using a HG-U133 plus 2 Array (GSE50683). RNA was isolated using a RNeasy kit (Qiagen). Data were normalized using d-Chip software. Differentially expressed gene signatures were analyzed using Gene Set Enrichment Analysis (GSEA) as previously reported (Subramanian et al., 2005). Gene sets were downloaded from a publically available source (Broad Institute, Cambridge, Mass.).

Results

Figure 8A:
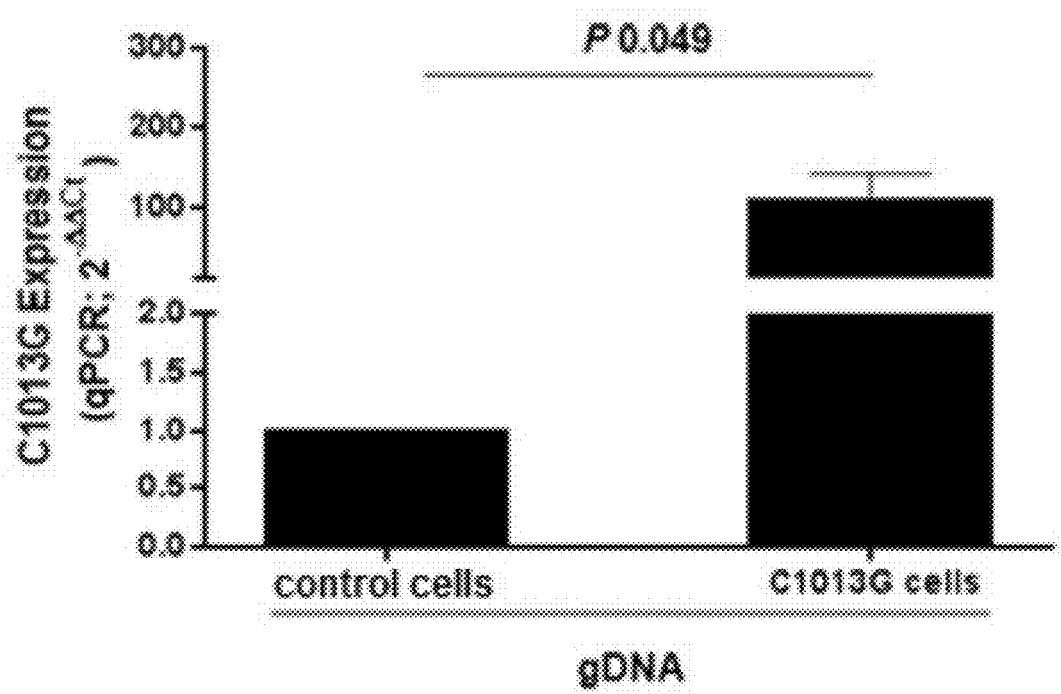
FIGS. 8A-8E.
Figure 8B:
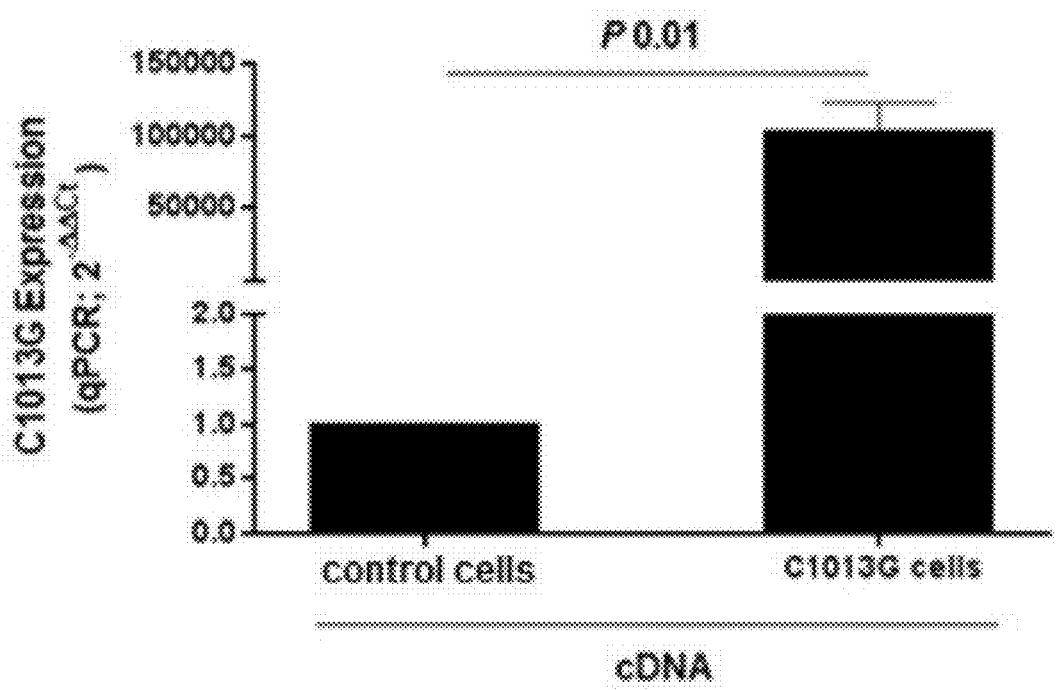
Figure 8C:
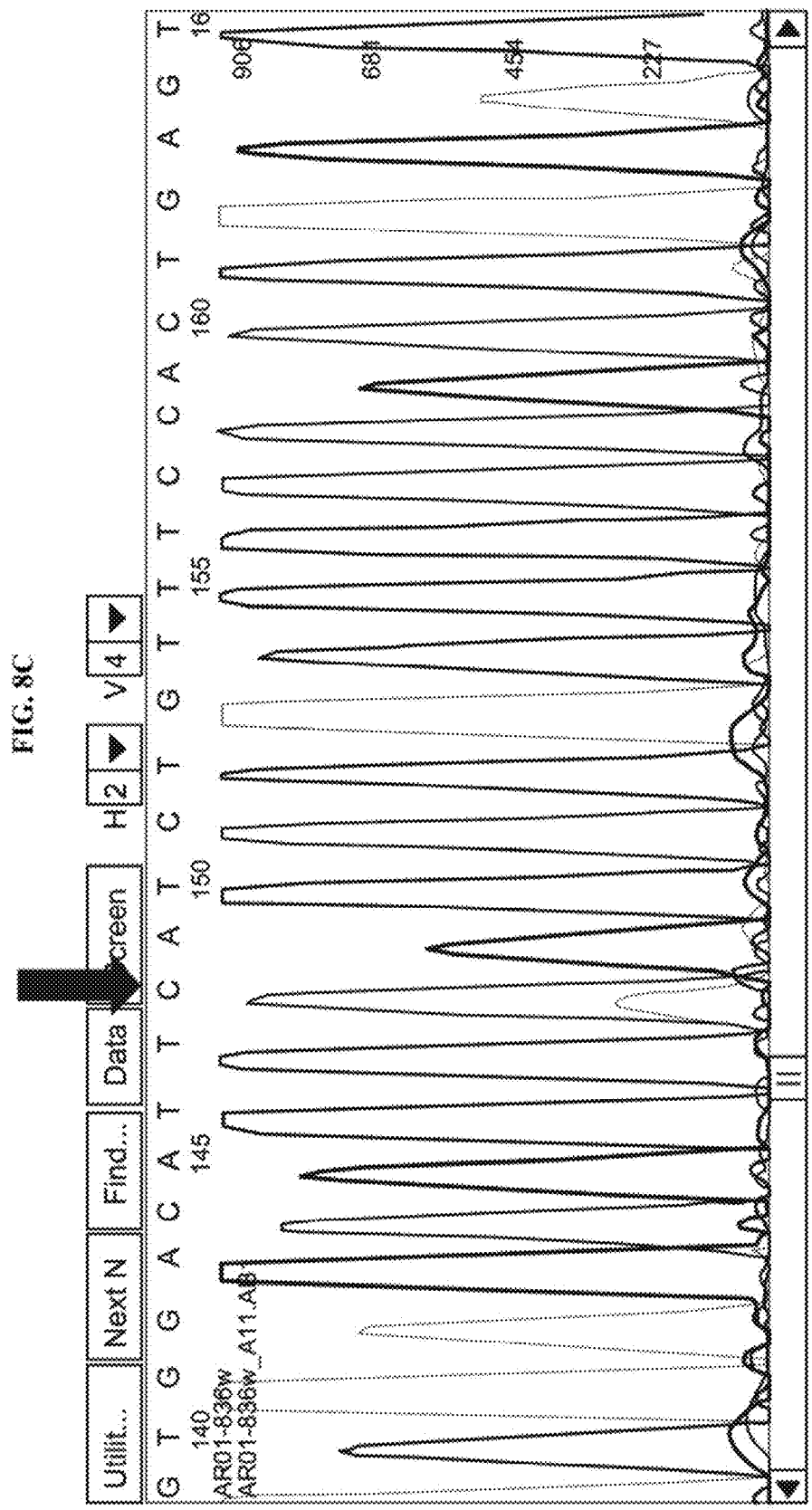

Stably C1013G-mutated WM cells (C1013G/CXCR4-WM) were generated and control vector-infected WM cells were used as control. The mutagenesis efficiency was confirmed at the genomic DNA and complementary DNA (cDNA) levels by quantitative PCR (qPCR) and qRT-PCR, respectively, and further validated by Sanger DNA sequencing (FIGS. 8A-C).

Figure 8D:
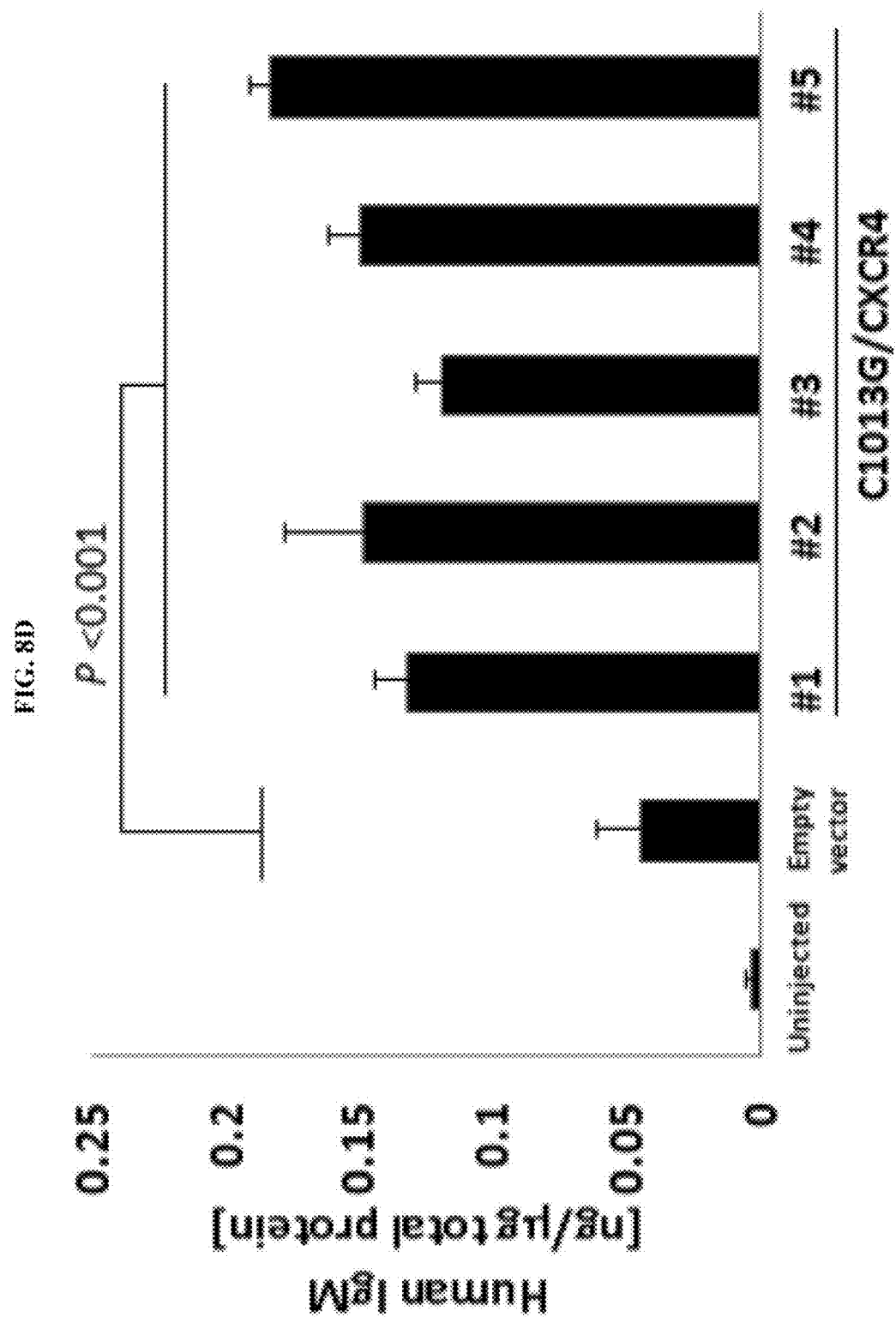
Figure 8E:
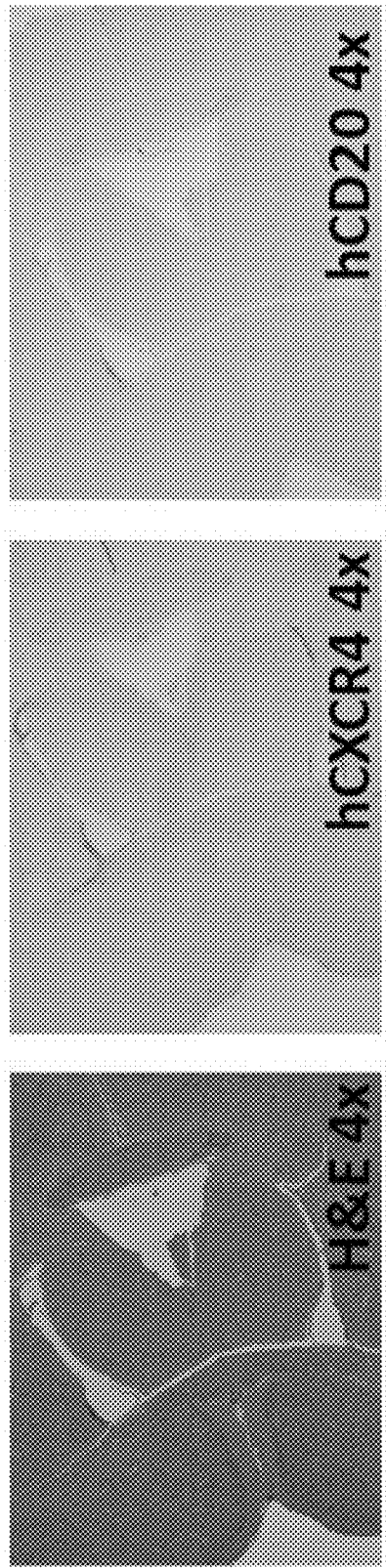
Figure 9F:
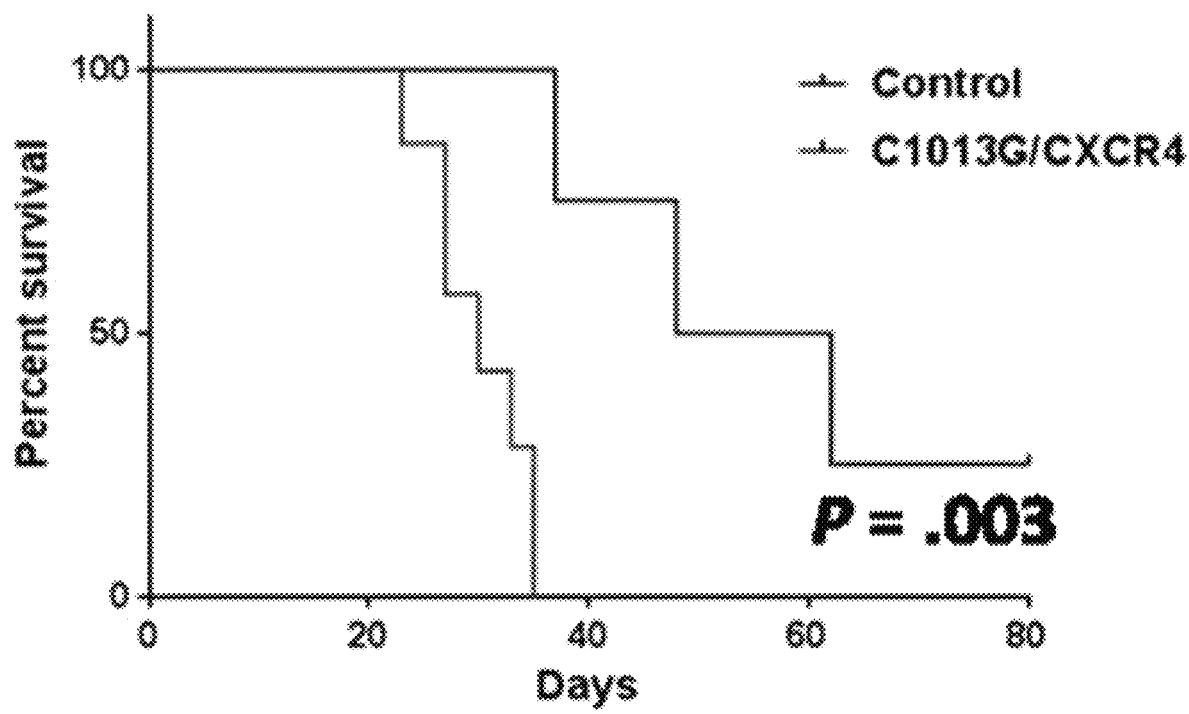
Figure 10A:
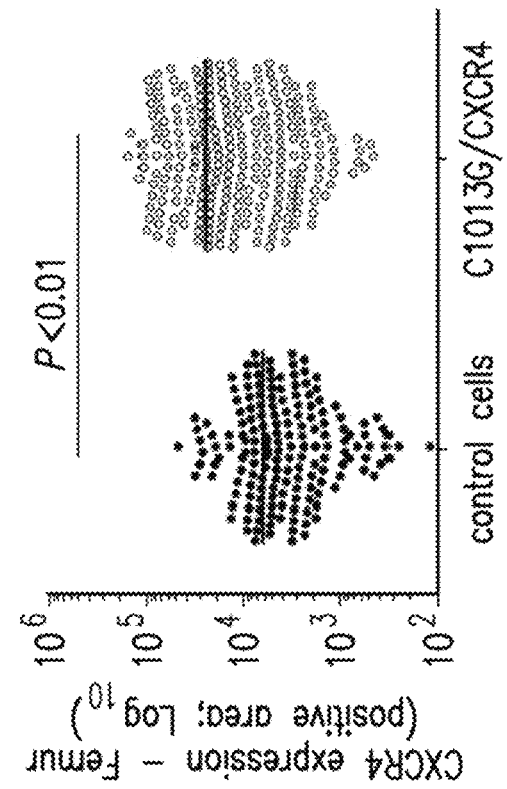
FIGS. 10A-10H.
Figure 10B:
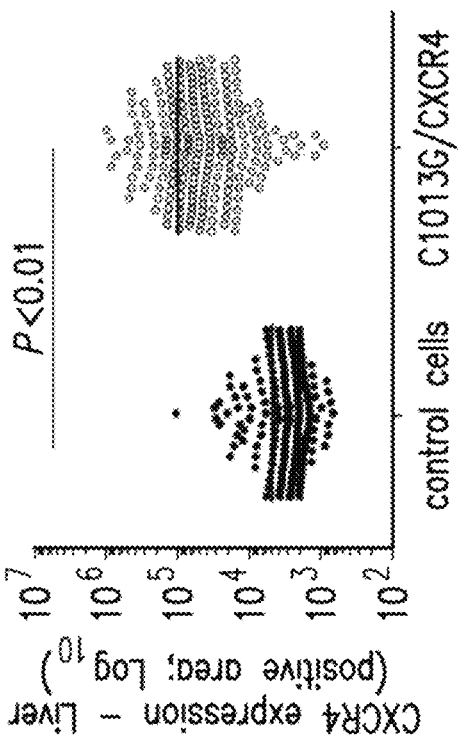
Figure 10C:
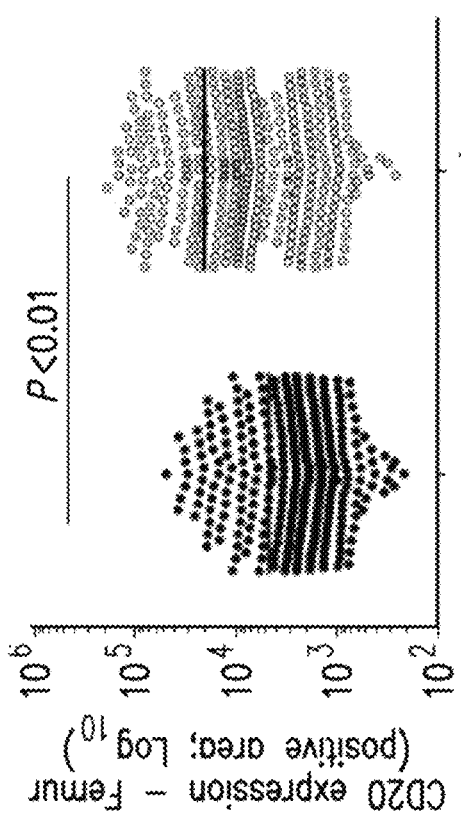
Figure 10D:
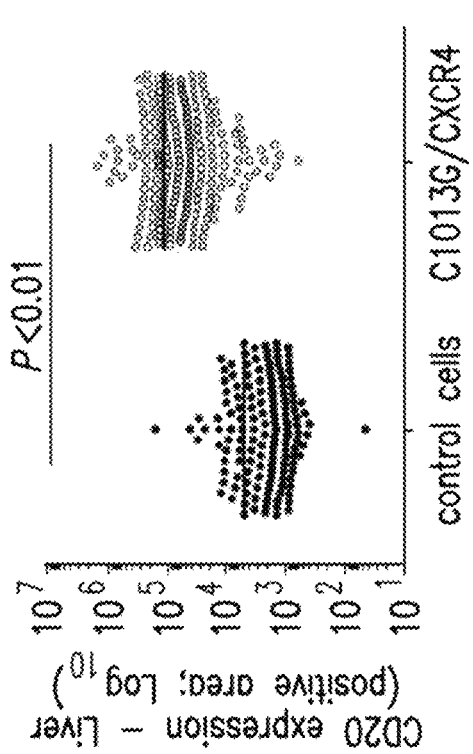
Figure 10E:
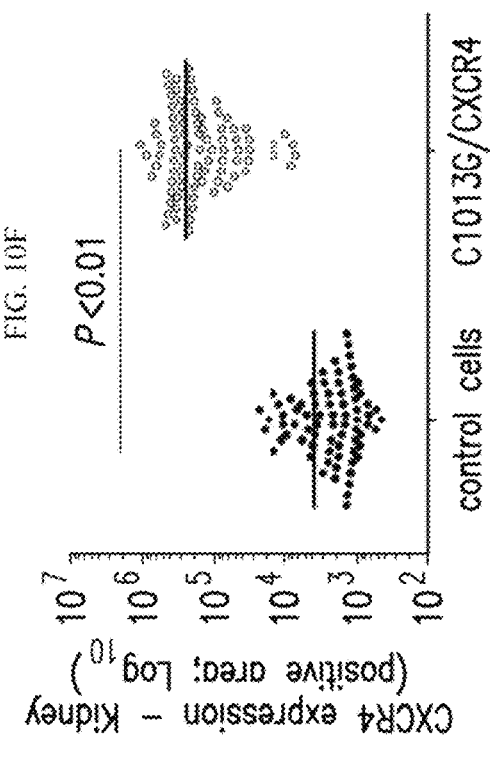
Figure 10G:
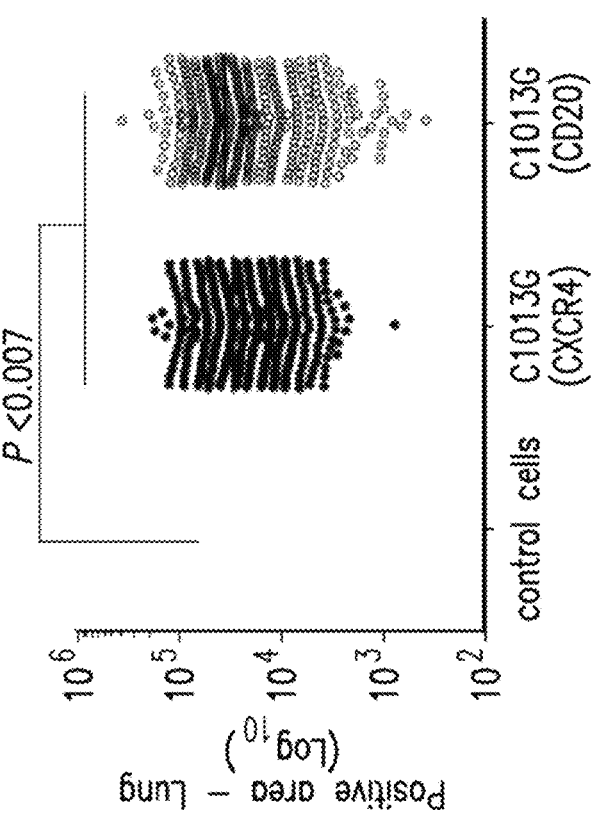
Figure 10F:
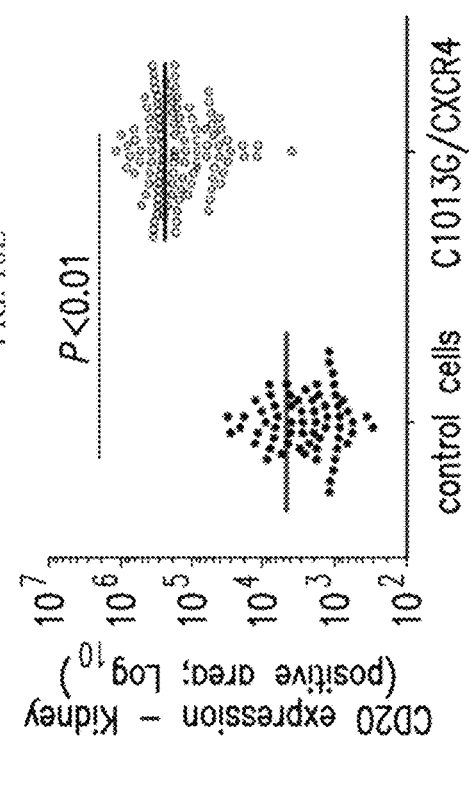
Figure 10H:
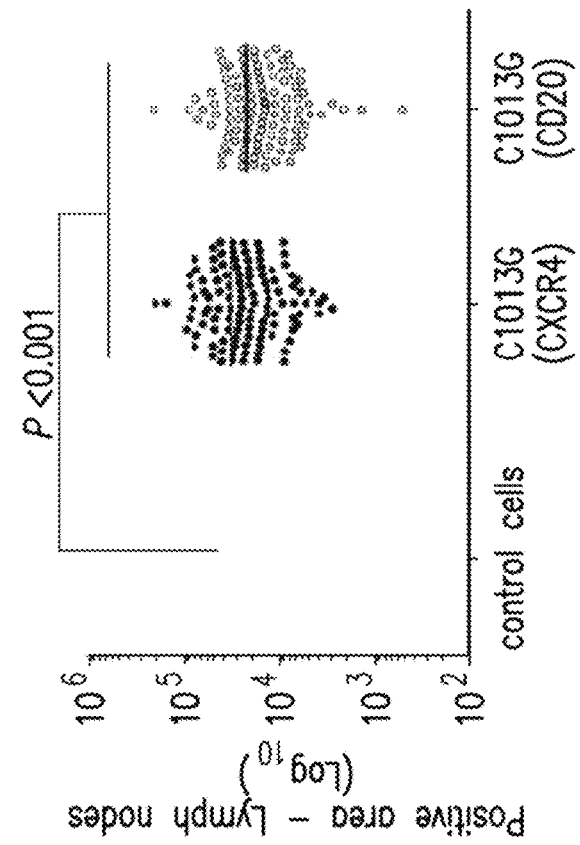

The in vivo phenotype induced by WM cells harboring the mutation was subsequently examined. Mice injected with C1013G/CXCR4-WM cells presented with a significant dissemination of tumor cells to distant organs and increased serum IgM secretion (FIG. 8D), thus recapitulating the effect observed in mice injected with CXCR4$^+$ over-expressing WM cells. In addition to the already demonstrated involvement of liver, kidney and BM, C1013G/CXCR4-WM cell-injected mice presented with enlarged lymph nodes and lung involvement. Dissemination to central nervous system was not observed. Histopathology analysis showed the presence of CXCR4- and CD20-positive cells in all the tissues examined, with the exception of the brain (FIG. 8E; FIGS. 9A-E), and the CXCR4 and CD20 positivity was higher in C1013G/CXCR4-WM cell-injected mice compared to control cell-injected mice (P<0.05; FIG. 10). Importantly, C1013G/CXCR4-WM cell-injected mice presented with decreased overall survival (P=0.003; FIG. 9F).

Figure 11A:
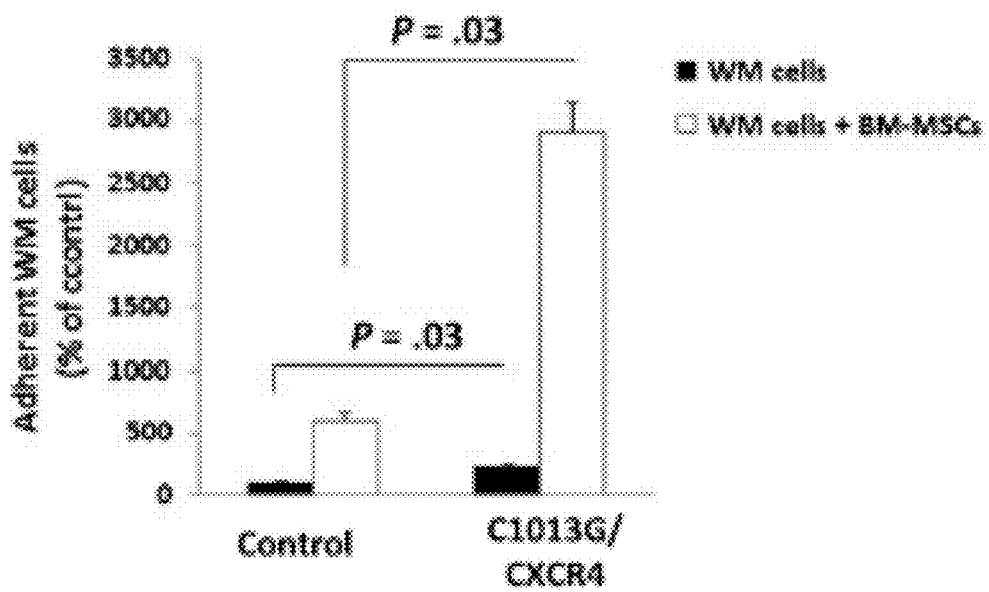
FIGS. 11A-11D.
Figure 11B:
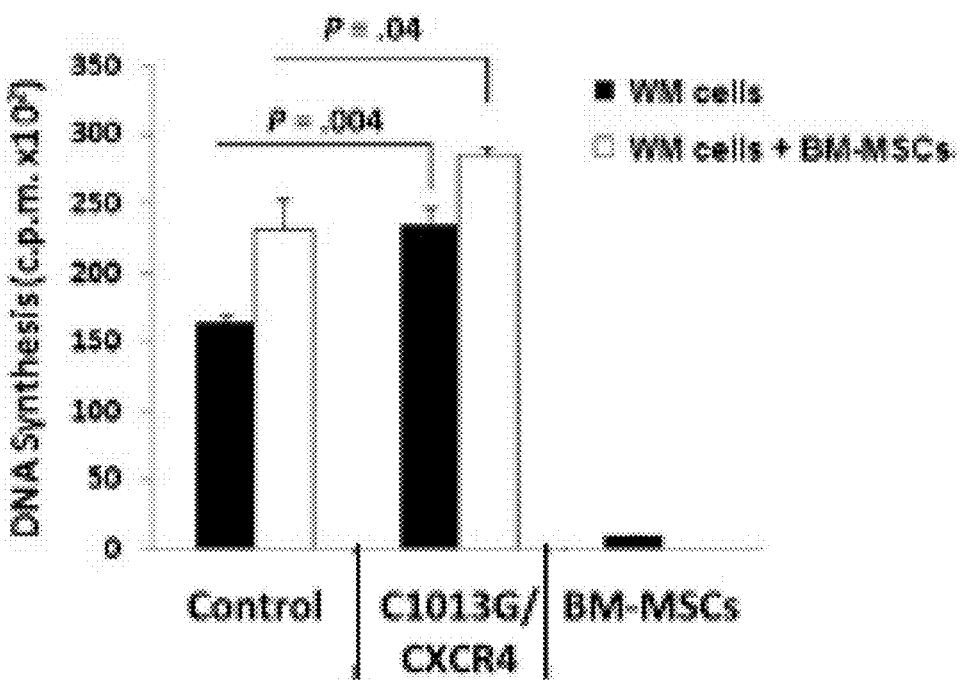
Figure 11C:
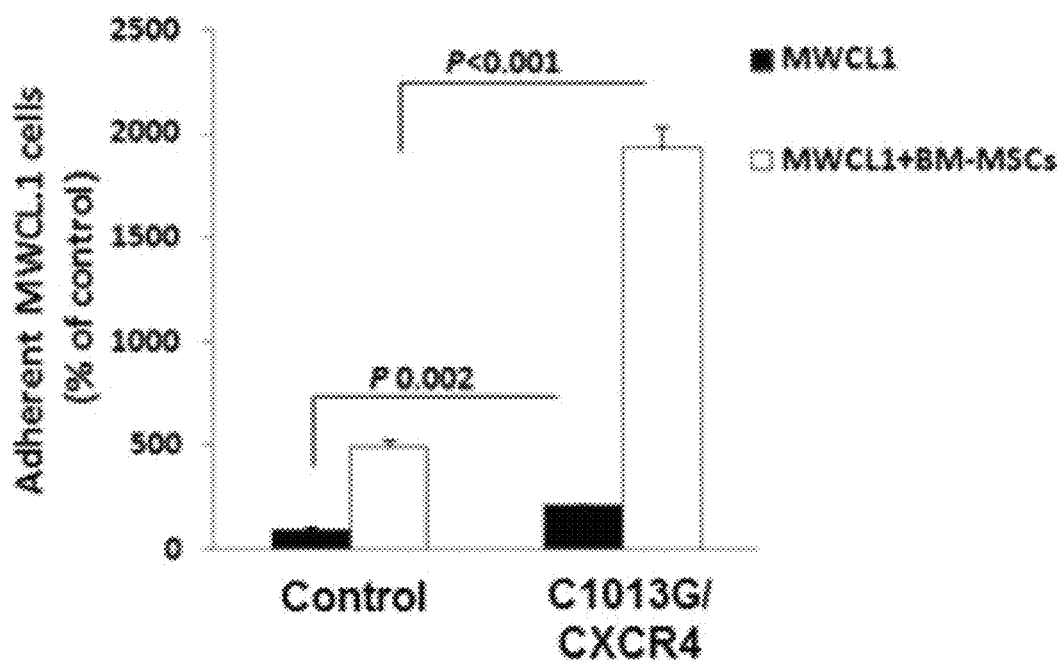
Figure 11D:
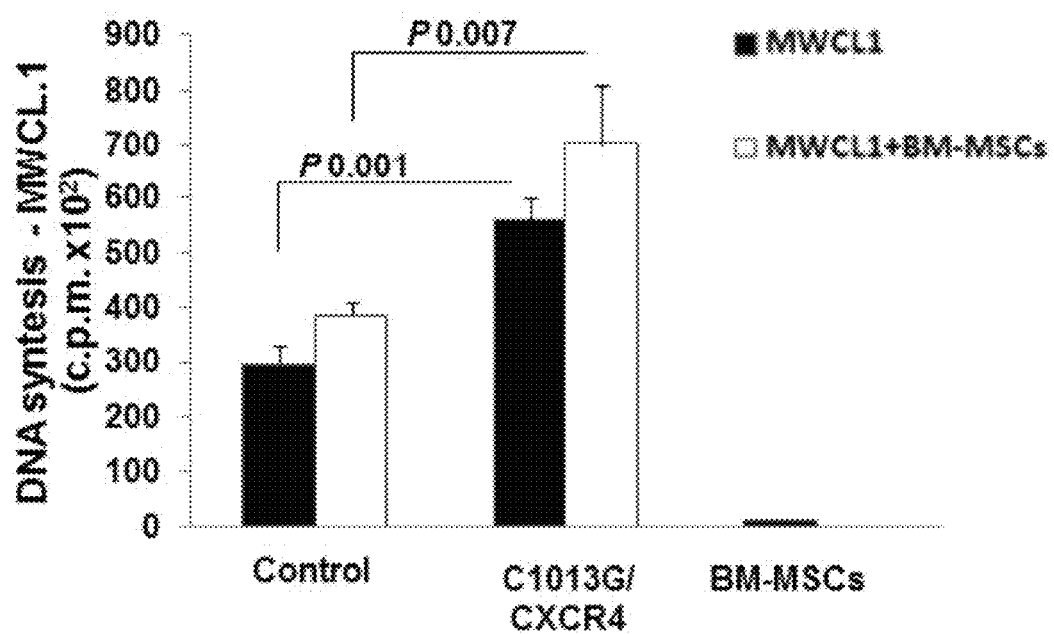

C1013G/CXCR4-WM cells (BCWM.1) were further characterized in vitro, showing increased adhesion and cell proliferation in the presence of primary WM BM-MSCs, thus confirming the C1013G/CXCR4 variant was able to reproduce the effects of over-expression of CXCR4 in WM cells (FIGS. 11A, B). Similar findings were validated using a different WM cell line (MWCL1; FIGS. 11C, D).

Figure 12C:
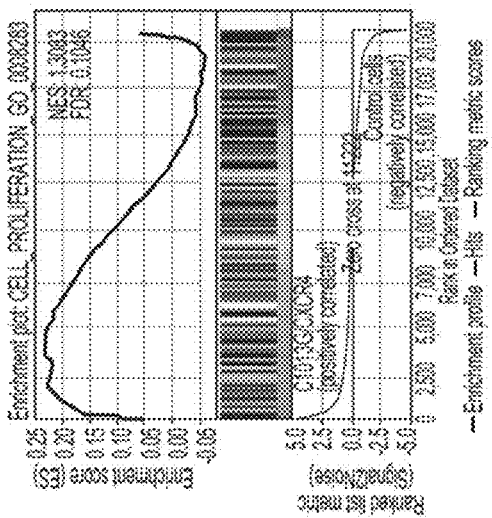
FIGS. 12A-12M.
Figure 12B:
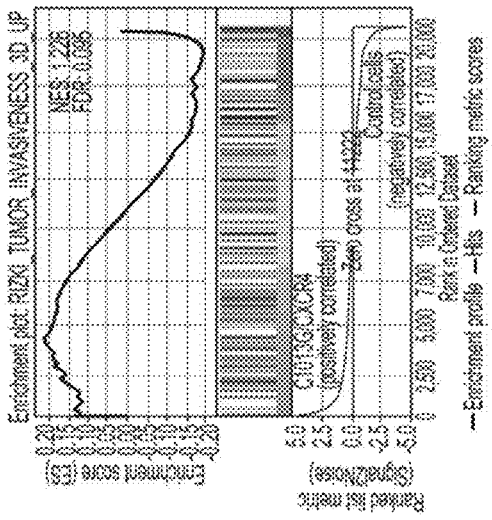
Figure 12A:
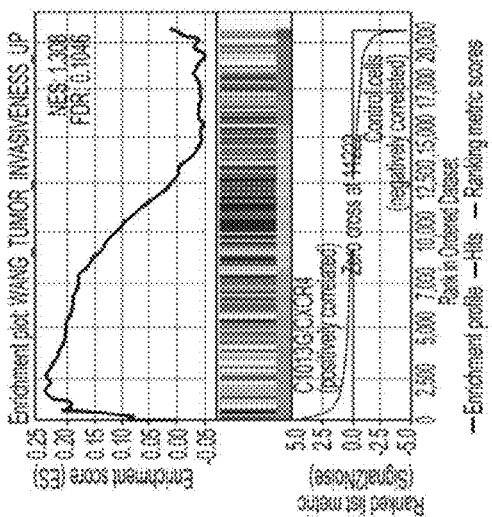
Figure 12F:
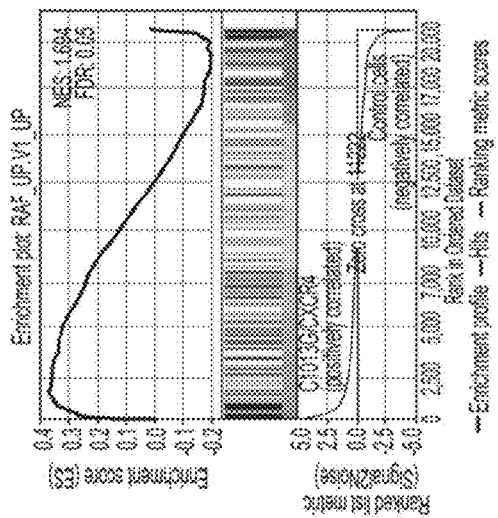
Figure 12E:
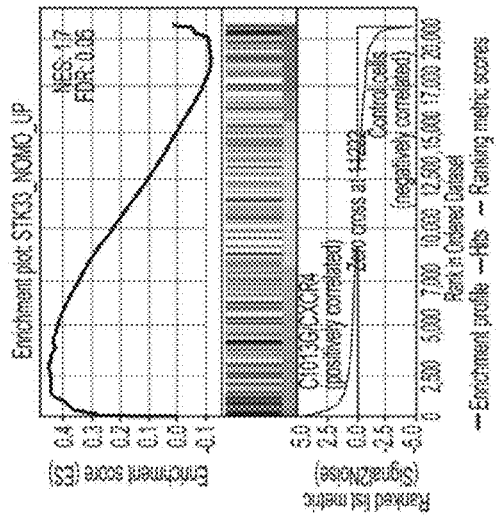

To better explain the ability of the C1013G/CXCR4 variant to facilitate in vivo WM cell dissemination, mutated cells were characterized at the mRNA level. Using GSEA, it was demonstrated that genes related to invasiveness, cell proliferation, antiapoptosis, and oncogenicity (Rizki A et al., 2008; Wang et al., 2007), were all enriched in C1013G/CXCR4-WM cells compared to the WM control vector-infected cells, consistent with the more aggressive phenotype of mutated cells compared to the control cells (FIG. 12A). These in vivo observations together with the changes observed at mRNA level indicate that the C1013G/CXCR4-WM variant acts as an activating mutation in WM cells.

WM patients were profiled at mRNA levels using qRT-PCR and several genes related to the mitogen-activated protein kinase, BTK, and PI3K pathways, that are known to support WM biology (Chng et al., 2008; Gutierrez et al., 2007), were found to be significantly upregulated in C1013G/CXCR4-mutated WM patients (n=10) compared with CXCR4/wild-type WM patients (n=30) (Table 3). Importantly, those changes were equally enriched in C1013G/CXCR4-mutated BCWM1 cells compared with the control vector-infected cells, thus further confirming that the C1013G/CXCR4-engineered BCWM.1 cells are representative for what observed in primary WM tumor cells (FIG. 12B).

Example 4

Resistance of C1013G/CXCR4-WM Variant to Conventional Anti-WM Agents

The sensitivity of WM cells harboring the C1013G/CXCR4 variant to conventionally used anti-WM small molecules was investigated.

Materials and Methods

Reagents

Everolimus, idelalisib, ibrutinib, bortezomib, and carfilzomib were purchased from Selleck Chemicals (Houston, Tex.). Drugs were dissolved in dimethylsulfoxide and subsequently diluted in cell culture medium (10% fetal bovine serum) immediately before use. The maximum final concentration of dimethylsulfoxide (0.1%) did not affect cell proliferation and did not induce cytotoxicity on the cell lines tested.

TABLE 3

Upregulation of genes in C1013G/CXCR4-WM patients

| Gene | Fold Change (WM patients C1013G/CXCR4 vs. unmutated) | P-value |
|---|---|---|
| ARID1A | 2,388 | 0.02 |
| BLNK | 5,598 | 0.012 |
| BTK | 2,291 | 0.019 |
| CCND1 | 5,567 | 0.026 |
| CD79A | 2.021 | 0.049 |
| CTNNBL1 | 1,989 | 0.046 |
| GSK3B | 2,288 | 0.014 |
| IRAK4 | 2,413 | 0.029 |
| IRF3 | 3,595 | 0.027 |
| ITPR1 | 2,824 | 0.018 |
| MAP3K1 | 1,809 | 0.010 |
| MAP3K7 | 3,004 | 0.002 |
| MAPK14 | 1.566 | 0.039 |
| MAPK1 | 2,039 | 0.012 |
| MAPK8 | 1,628 | 0.032 |

TABLE 3-continued

Upregulation of genes in C1013G/CXCR4-WM patients

| Gene | Fold Change (WM patients C1013G/CXCR4 vs. unmutated) | P-value |
|---|---|---|
| NREP | 2,359 | 0.038 |
| OSBPL3 | 3,178 | 0.025 |
| PAX5 | 1,911 | 0.016 |
| PI3KCB | 2,228 | 0.023 |
| POU2AF1 | 2,198 | 0.046 |
| RAF1 | 1,618 | 0.023 |
| RELA | 1,809 | 0.036 |
| SMEK1 | 2,152 | 0.014 |

Upregulation of genes in WM patients harboring the C1013G/CXCR4 mutation (n=10) is compared with CXCR4/wild-type WM patients (n=30).

BMS936564/MDX-1338 and the control human IgG4 isotype control were obtained from Bristol-Myers Squibb (Redwood City, Calif.).

Gene Set Enrichment Analysis

GSEA was performed as described in Example 3.

Results

Figure 12D:
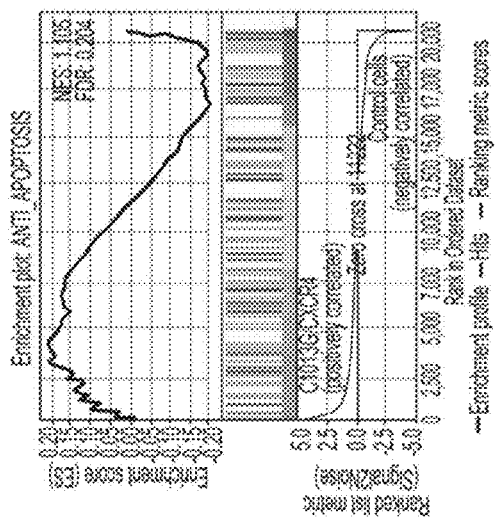
Figure 12G:
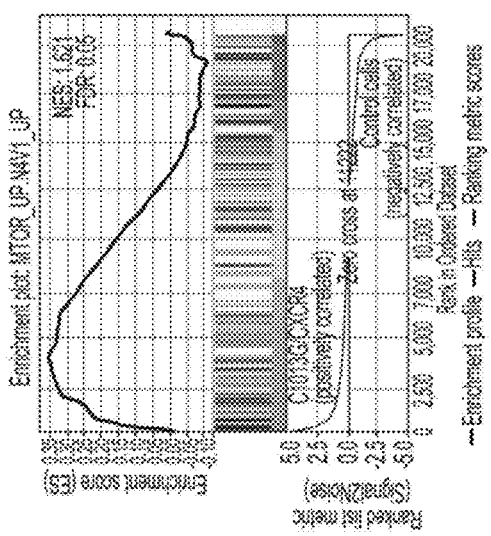
Figure 12H:
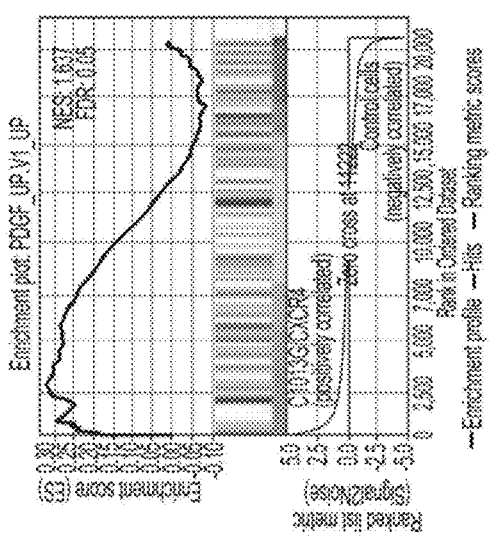
Figure 12I:
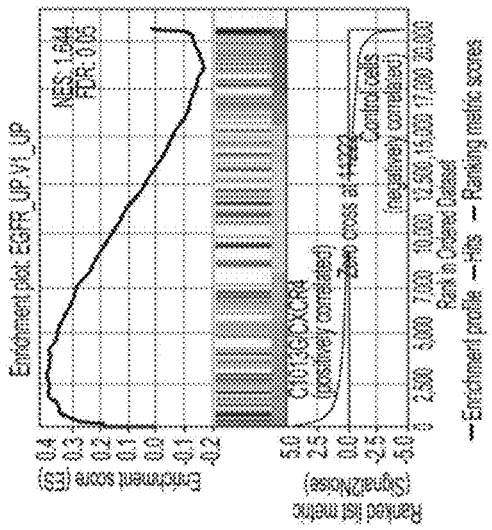
Figure 12J:
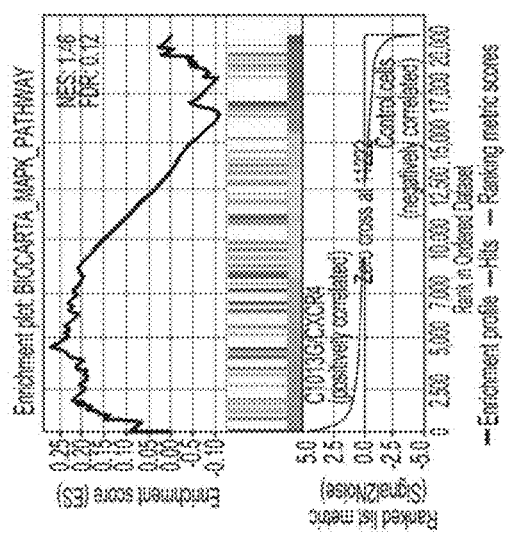
Figure 12K:
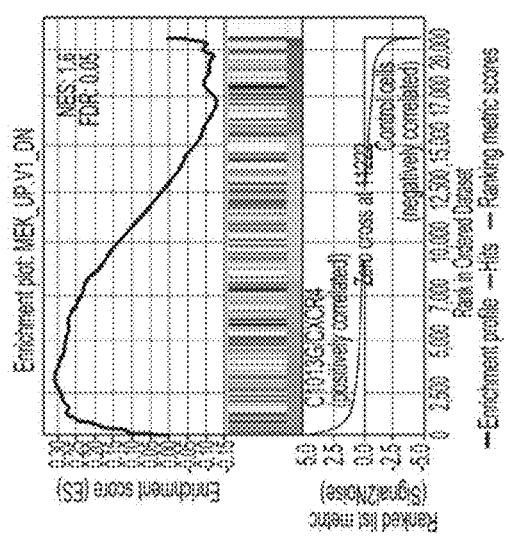
Figure 12L:
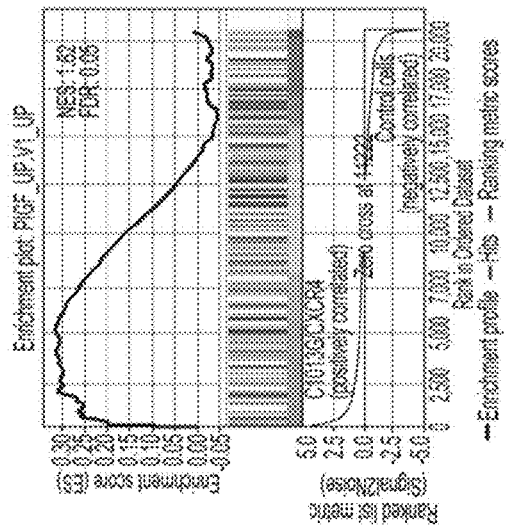
Figure 12M:
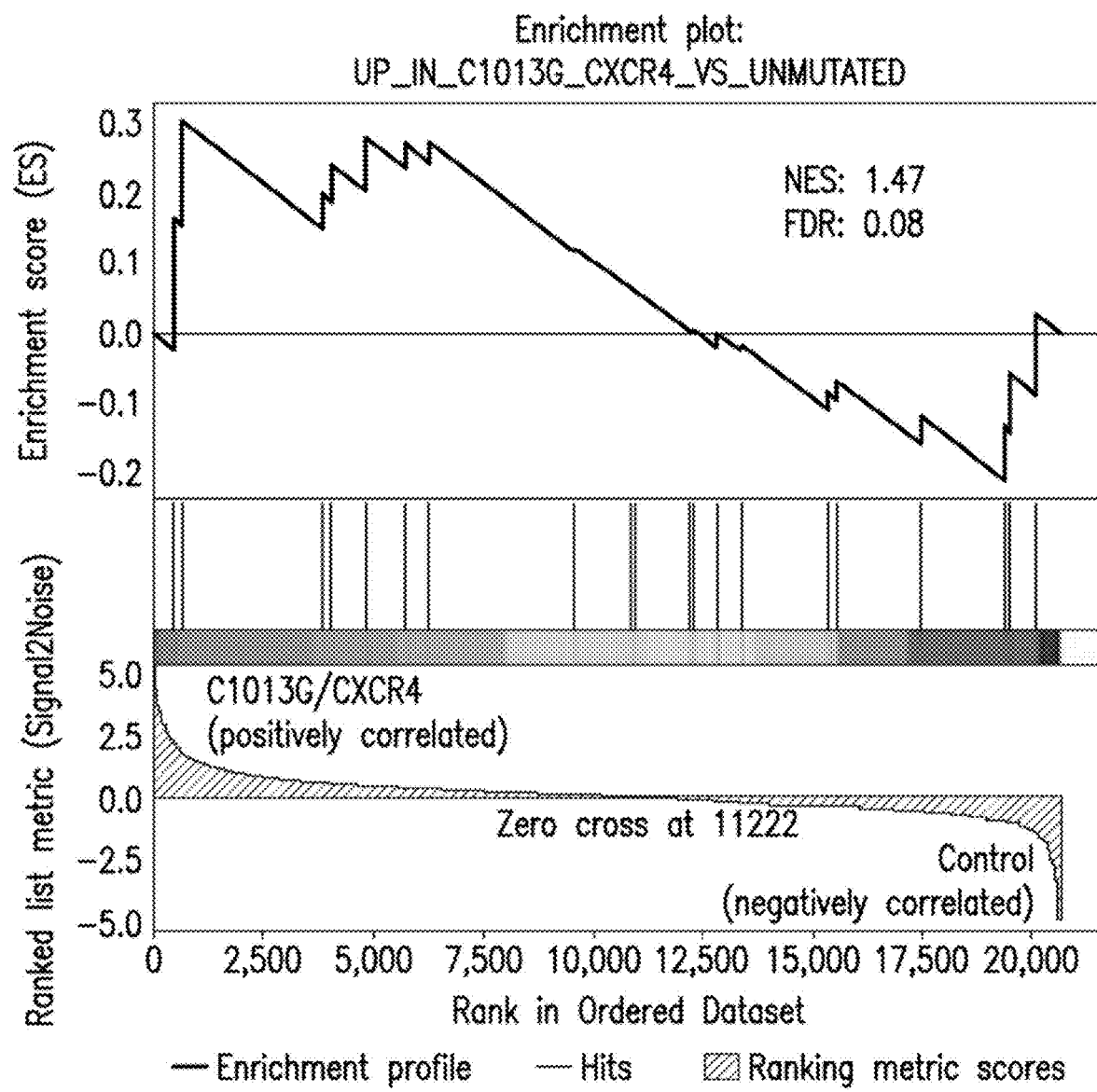
Figure 13A:
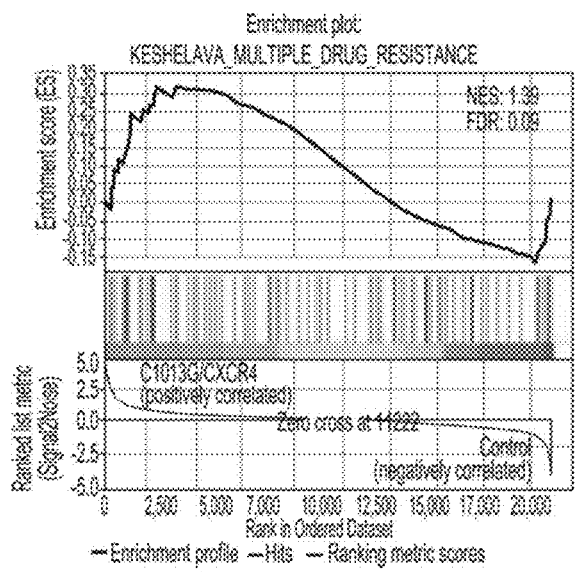
FIGS. 13A-13G.
Figure 13B:
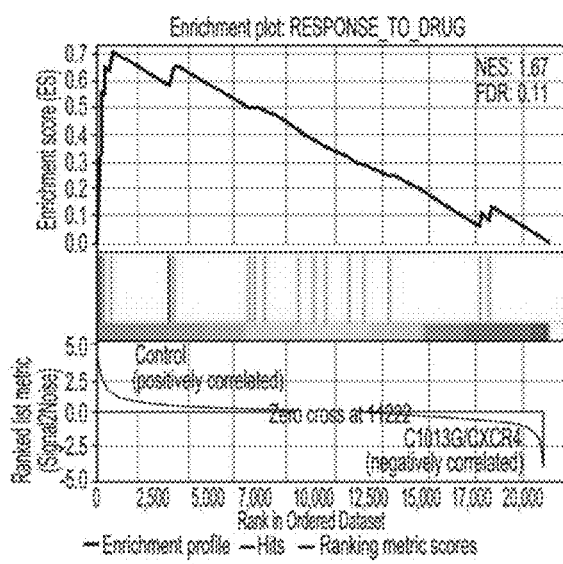
Figure 13C:
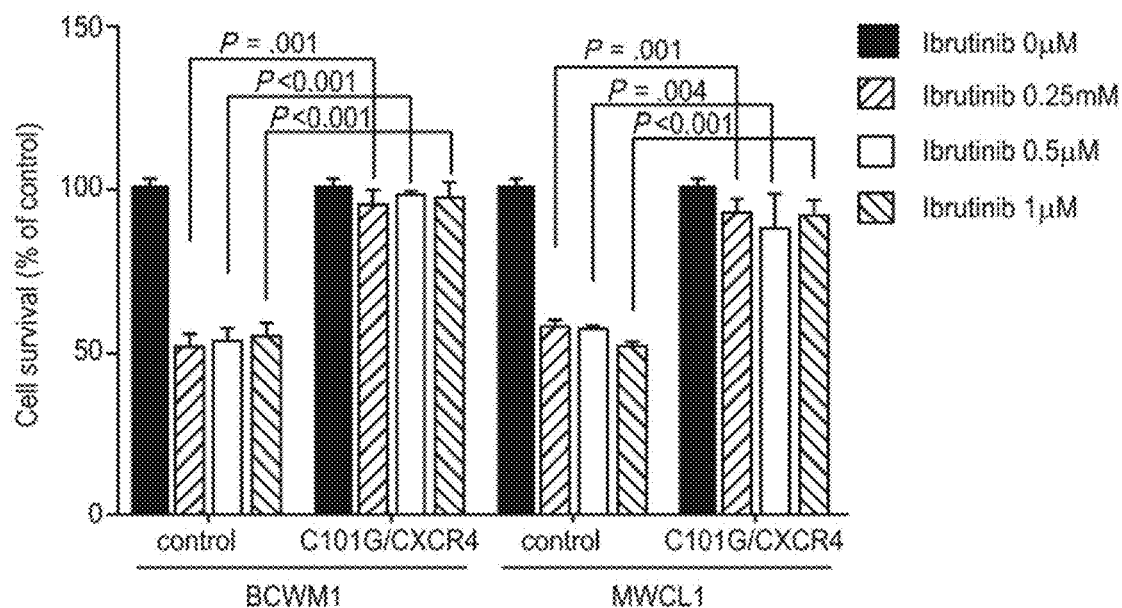
Figure 13D:
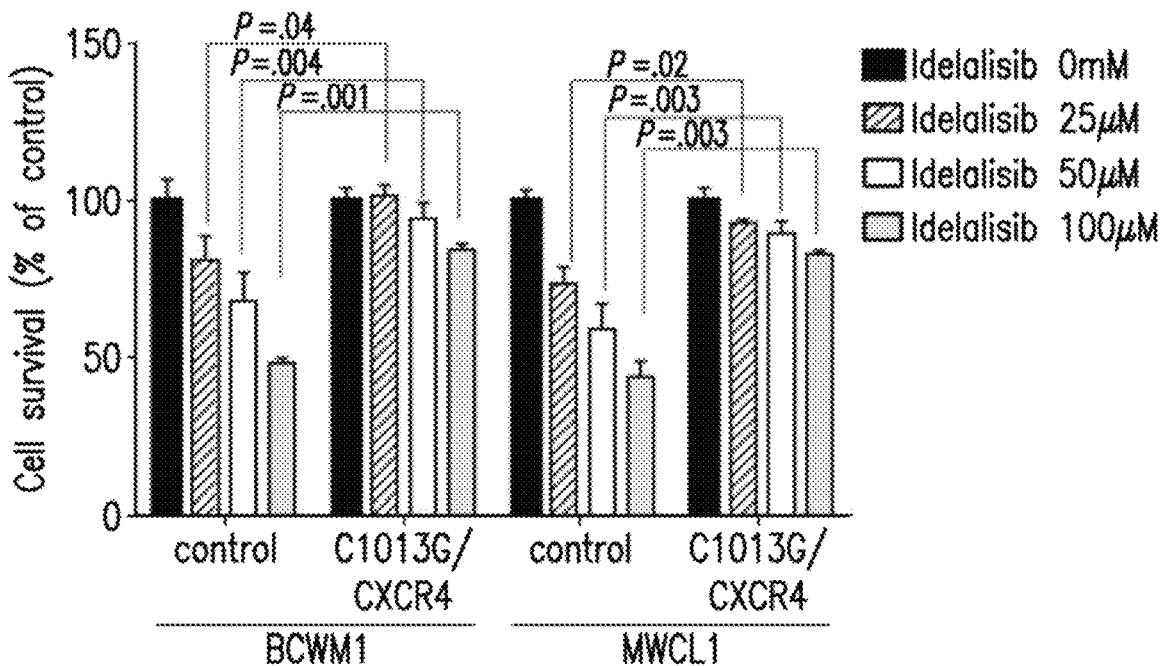
Figure 13E:
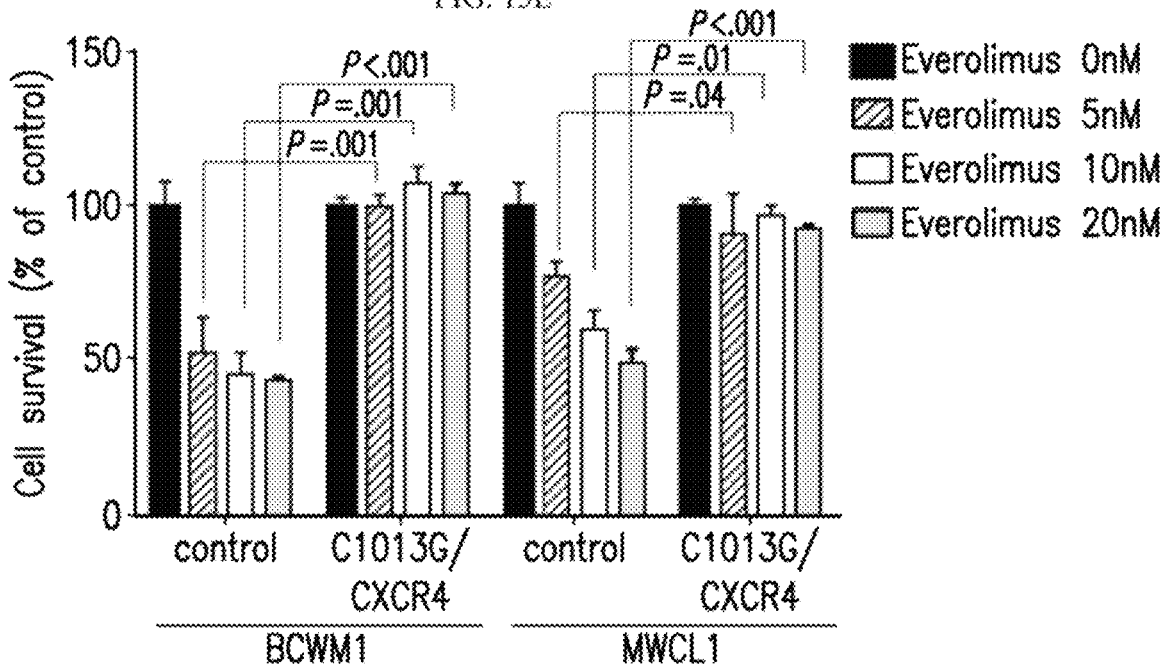
Figure 13F:
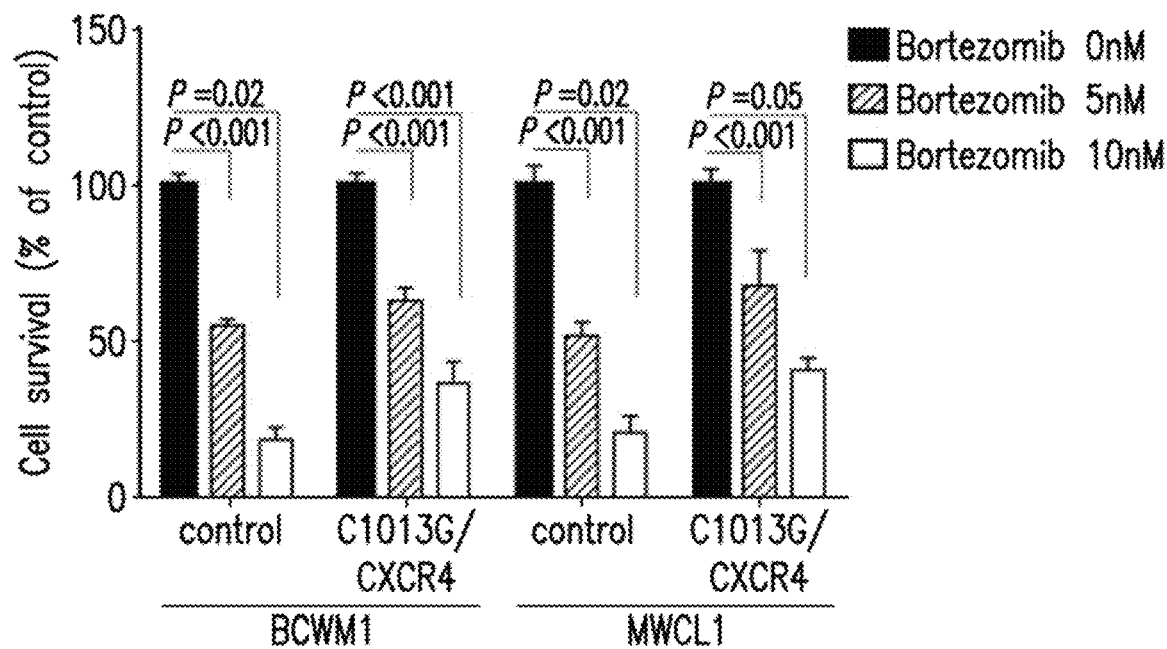
Figure 13G:
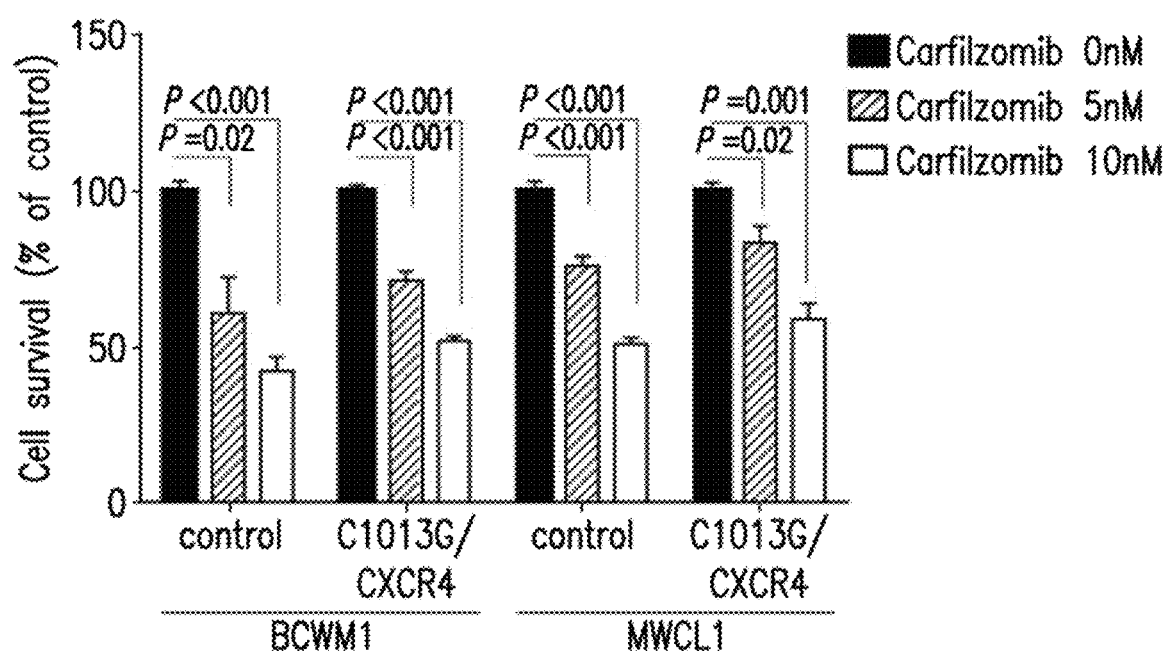

GSEA studies showed that genes related to drug resistance were enriched in WM cell line harboring the mutation, whereas genes related to drug responsiveness were enriched in WM control cells (FIG. 13A). This prompted an investigation into whether novel anti-WM agents may alter their antitumor efficacy in the context of CXCR4-mutated WM cells. It was found that WM cells harboring the C1013G/CXCR4 somatic variant presented with resistance to BTK as well as PI3K and mTOR inhibitors (FIGS. 12B-D). These data are in support of recent data indicating that WM patients with WHIM-like mutated CXCR4 presented with resistance to ibrutinib-based therapy (Cao et al., 2013; Treon et al., 2013). Importantly, proteasome inhibitors were equally effective in exerting toxicity against both C1013G/CXCR4-mutated WM cells and control cells (FIGS. 13E-F).

Example 5

Targeting of WM Cells by Anti-CXCR4 Antibody BMS-936564

Based on the biological relevance of CXCR4 in supporting WM progression, the anti-CXCR4 human monoclonal antibody BMS-935564 (designated F7 in WO 2008/060367; also known as ulocuplumab or MDK-1338) was tested for activity in targeting WM cells. Assays for measuring adhesion, migration and proliferation of WM cells were performed as described in Example 2, and gene expression studies were conducted were performed as described in Example 3.

Immunoblotting

Protein lysates were obtained from WM cells by homogenization under nondenaturing conditions in lysis buffer (Cell Signaling Technology, Beverly, Mass.) supplemented with 5 mM NaF, 2 mM $Na_3VO_4$, 1 mM PMSF (polymethilsulfonyl fluoride), 5 µg/mL leupeptine, and 5 µg/mL aprotinin. Whole-cell lysates were subjected to sodium dodecyl sulfate-polyacrylamide gel electrophoresis (SDS-PAGE) and transferred to polyvinylidene difluoride (PVDF) membrane (Bio-Rad Laboratories, Hercules, Calif.). The antibodies used for immunoblotting included: anti-phospho (p)-ERK, anti-ERK, anti-p-Akt, anti-Akt, anti-p-Src, anti-Src, anti-caspase-9, anti-PARP, anti-p-β-catenin, anti-β- catenin, anti-p-GSK3, anti-GAPDH and anti-α-tubulin antibodies (Cell Signaling, Danvers, Mass.).

Results

Figure 14A:
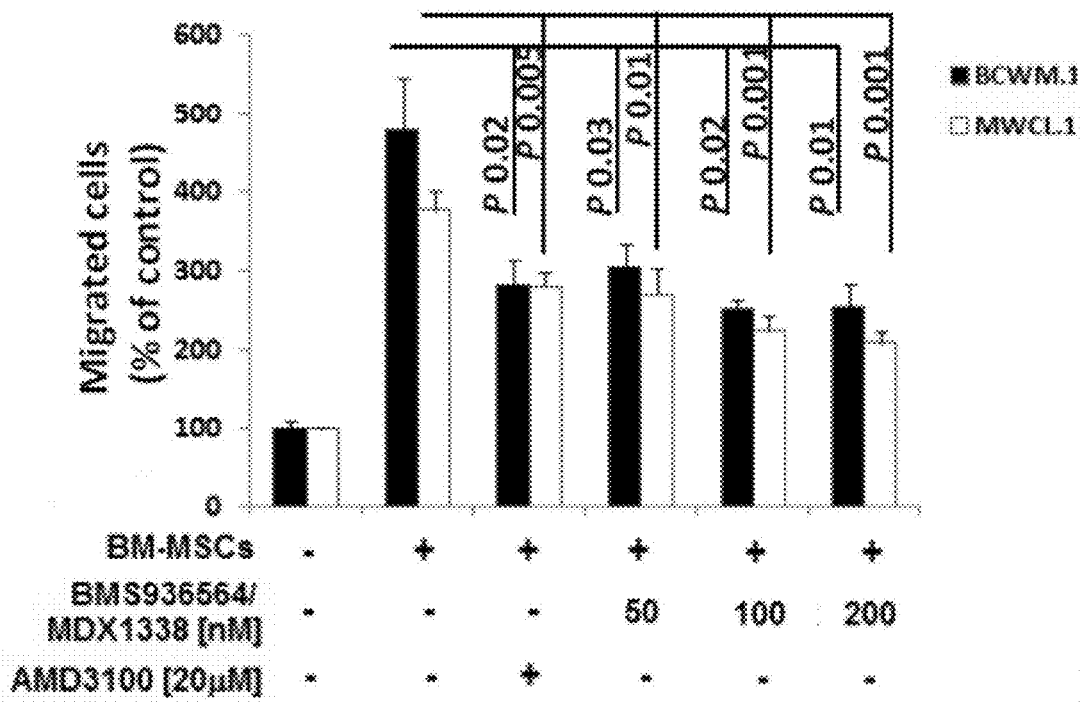
FIGS. 14A and 14B.
Figure 14B:
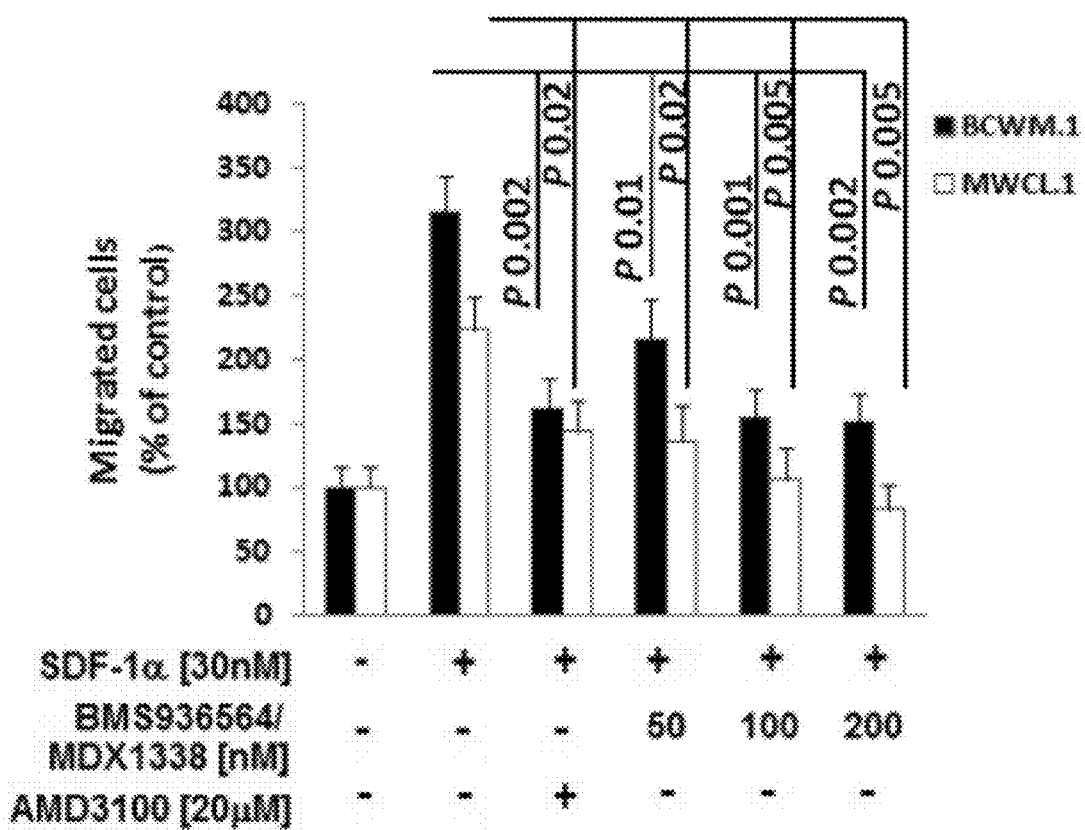

BMS-936564 was shown to inhibit migration of WM cell lines towards either primary WM BM-MSCs or SDF-1 (FIGS. 14A, B).

Figure 15A:
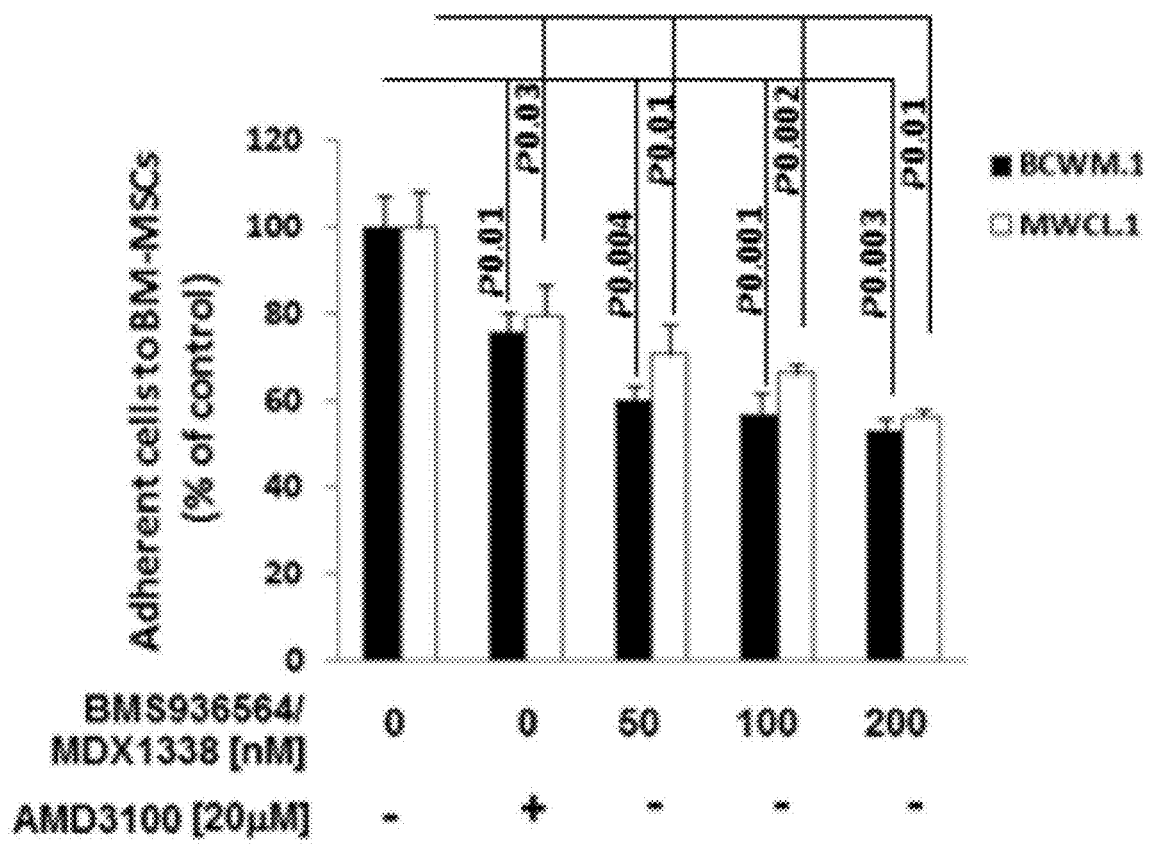
FIGS. 15A-15C.
Figure 15B:
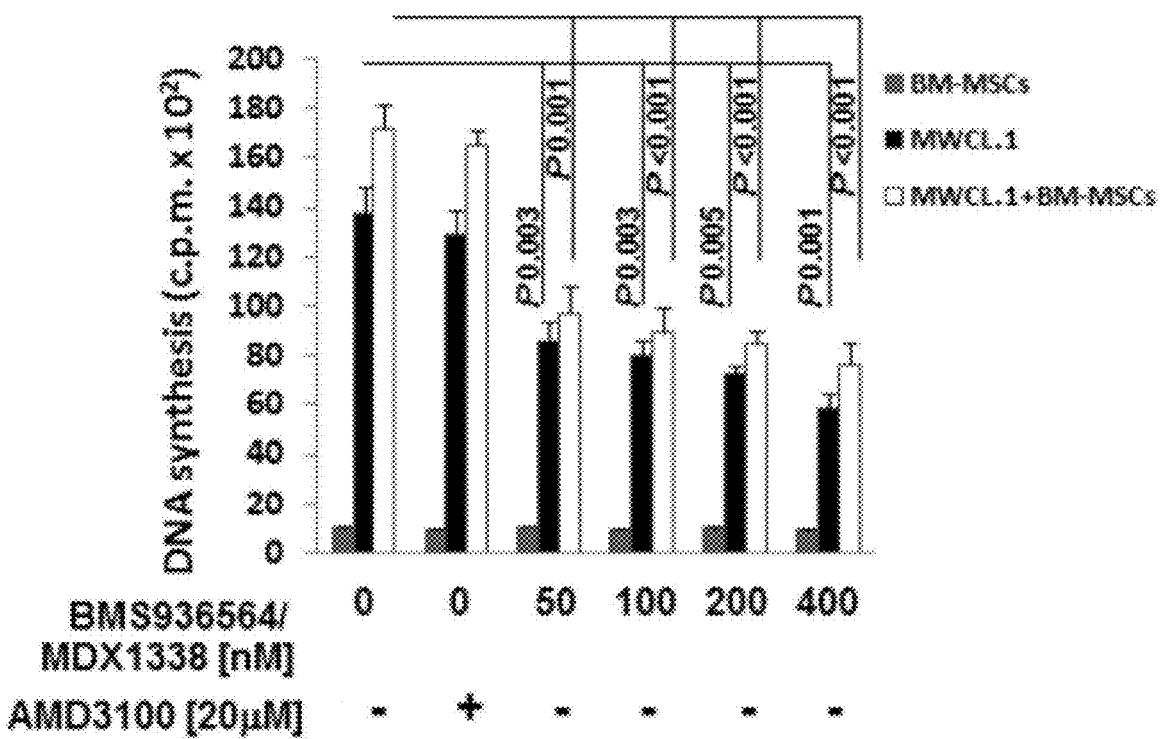
Figure 15C:
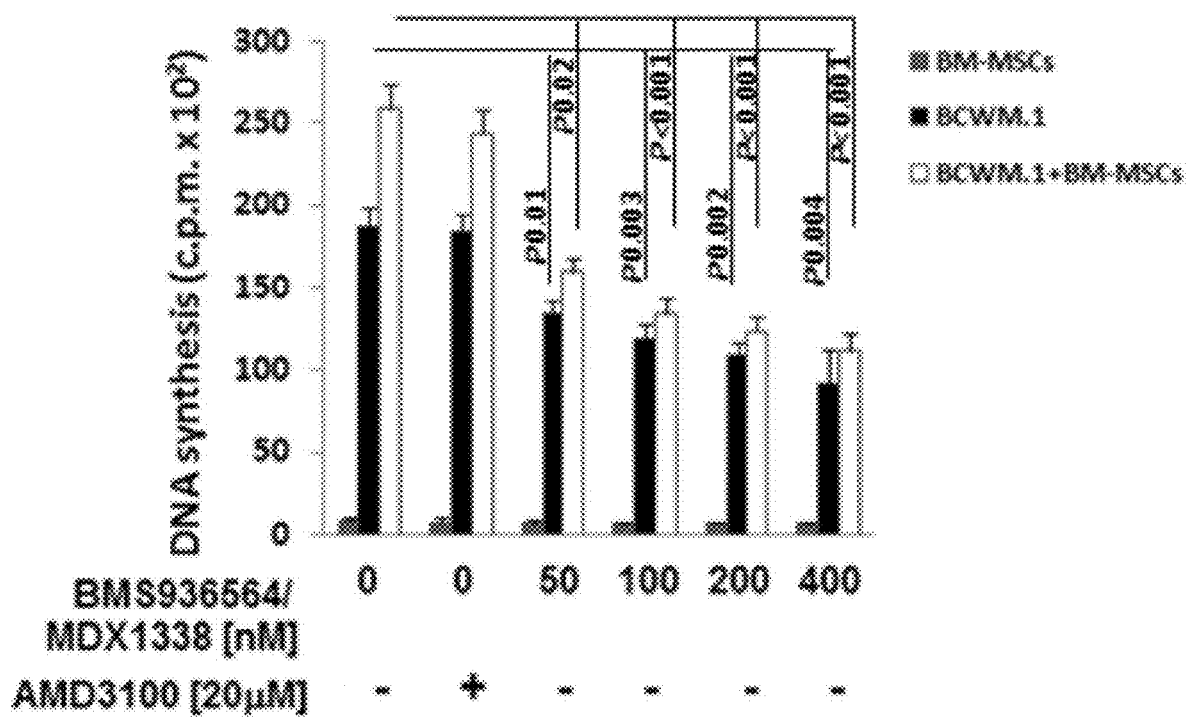

Similarly, BMS-936564-dependent inhibition of WM cell adhesion to WM BM-MSCs and inhibition of WM cells proliferation in presence of WM BM-MSCs were demonstrated (FIGS. 15A-C).

Figure 16:
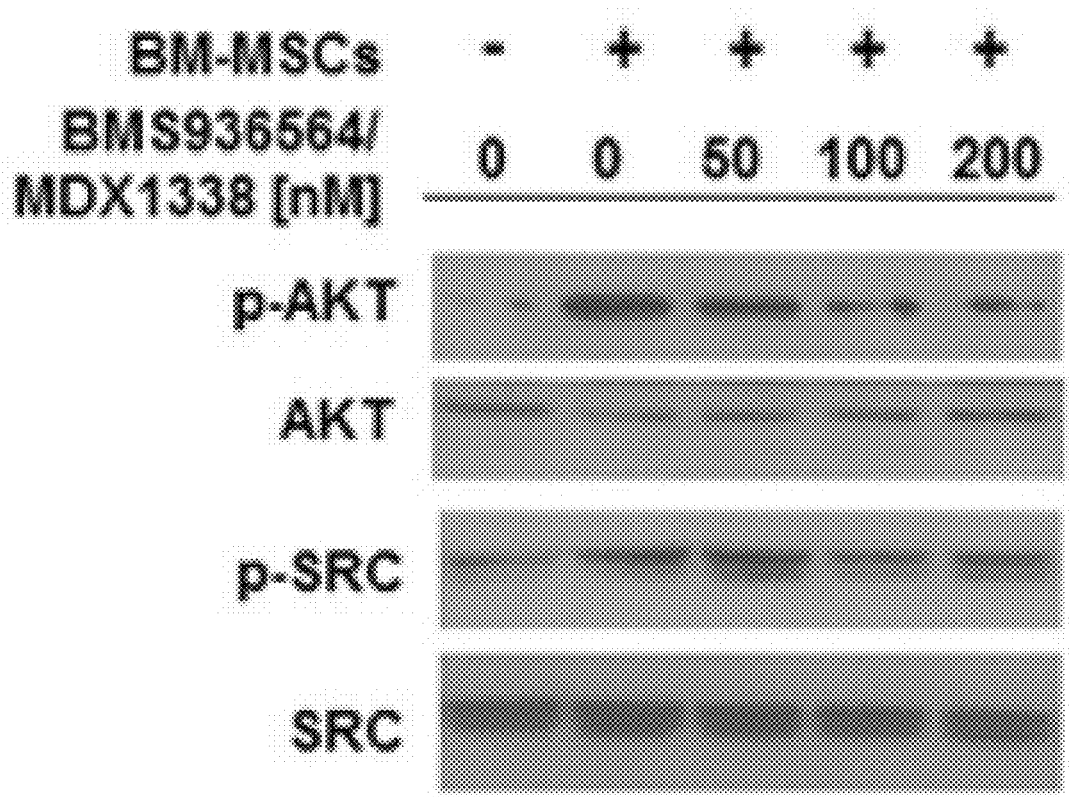
FIG. 16 shows the effect of BMS-936564 on WM cell signaling. BCWM.1 cells were exposed to BMS-936564 for 6 h in presence or absence of primary WM BM-MSCs. The BCWM.1 cells were then harvested and cell lysates were subjected to western blot analysis using anti-phospho(p)-ERK1/2, anti-ERK1/2, anti-p-Akt, anti-Akt, anti-p-SRC, and anti-SRC antibodies. BCWM.1 cells cultured in the absence of WM BM-MSCs were used as control. Bars indicate standard deviation.

To dissect the possible role of BMS-936564 in affecting WM signaling, WM cells were cultured in the absence or presence of primary WM BM-MSCs, with increasing concentrations of the anti-CXCR4 antibody. A drug-dependent inhibition of p-Akt, p-ERK, and p-Src was observed in WM cells cultured in the context of BM-MSCs, suggesting the ability of BMS-936564 to target WM cells even in the context of the BM milieu (FIG. 16).

Figure 17A:
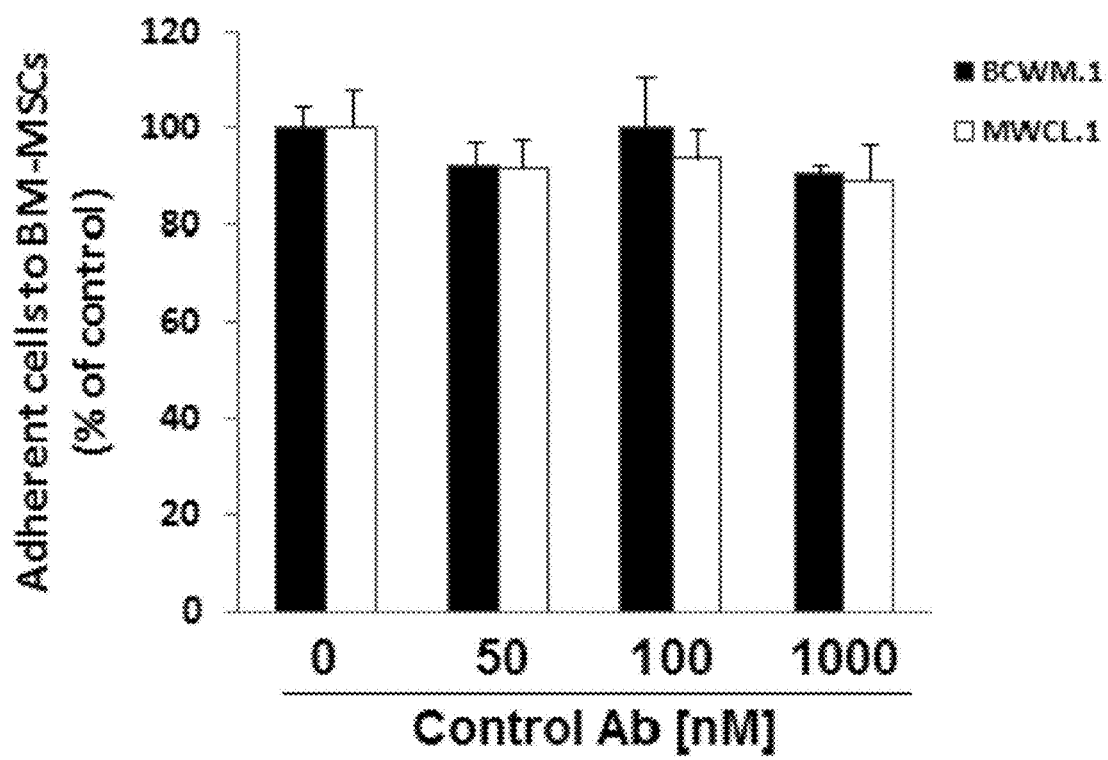
FIGS. 17A and 17B.
Figure 17B:
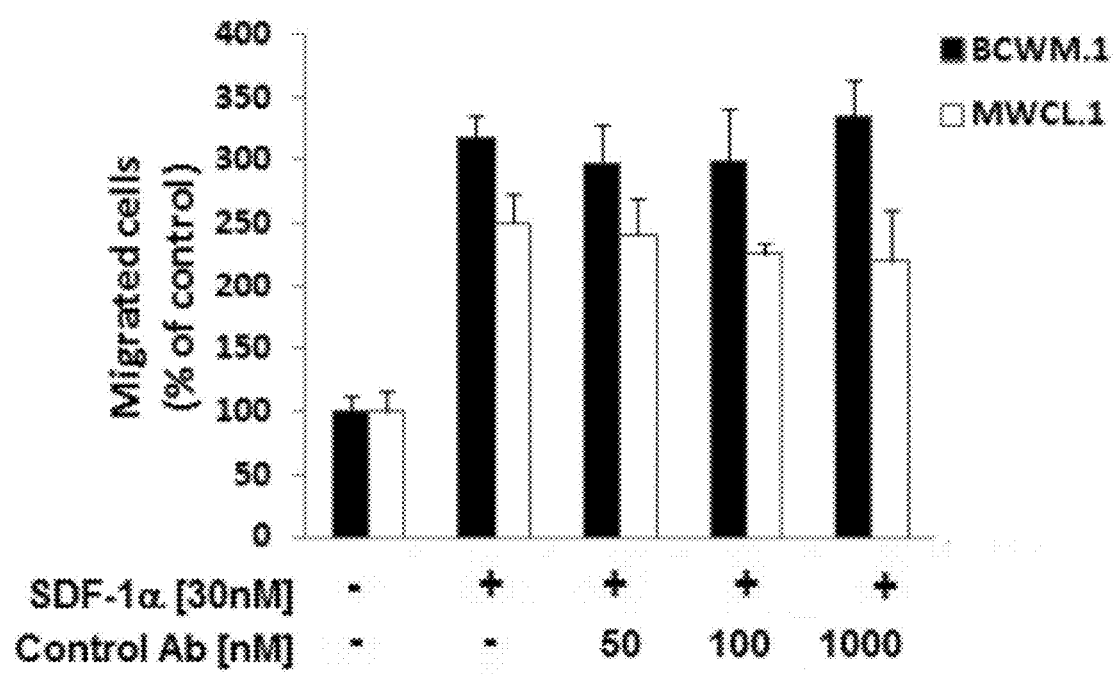

Isotype control did not exert any effect on adhesion and migration of WM cells in vitro (FIGS. 17A, B).

Figure 18B:
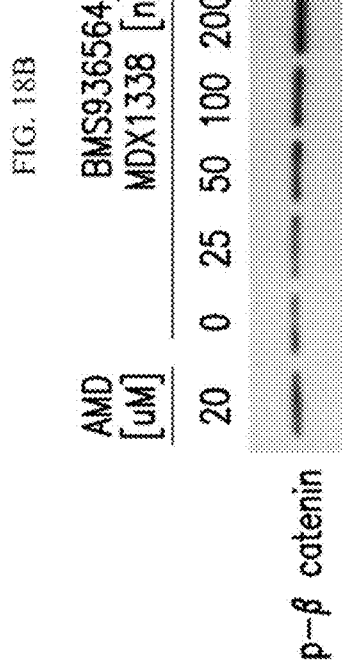
FIGS. 18A and 18B.
Figure 18A:
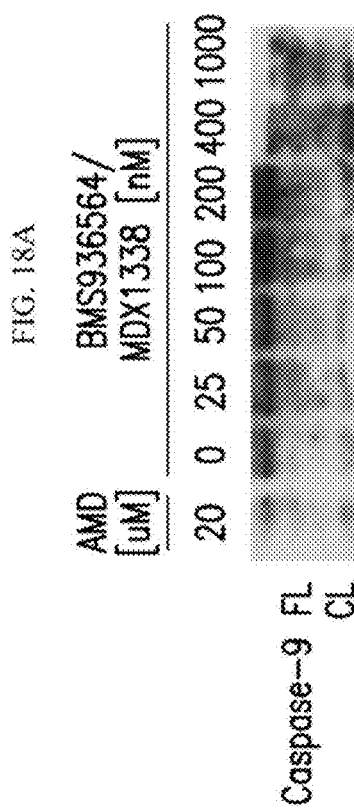
Figures 19A, 19B:
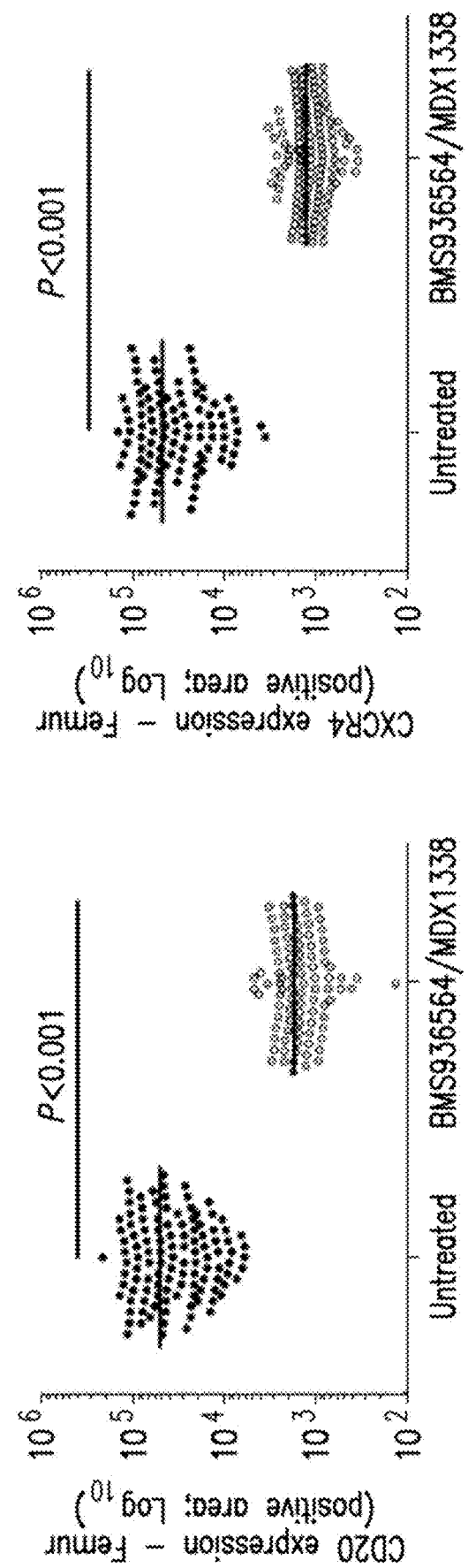
FIGS. 19A-19J.
Figure 19C:
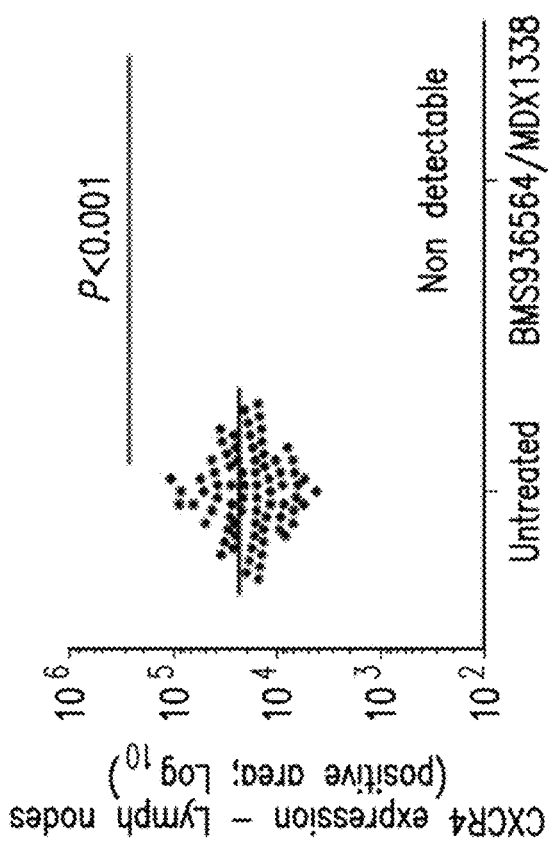
Figure 19D:
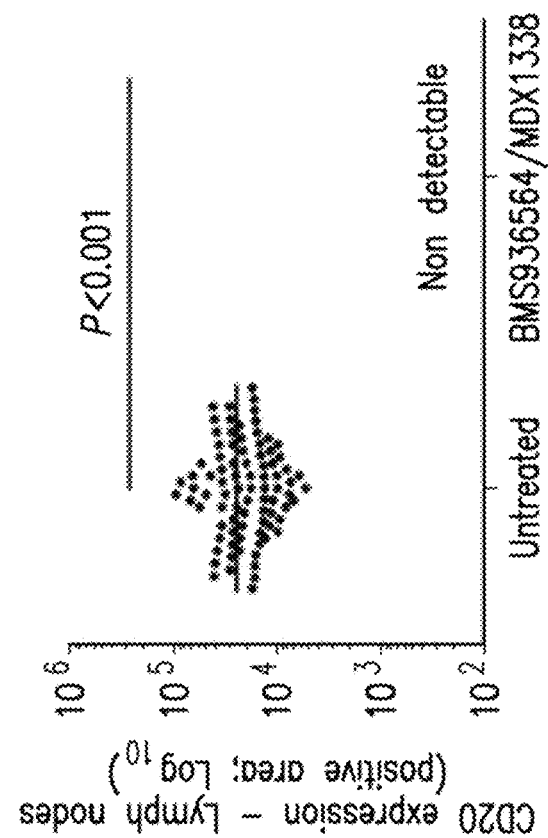
Figure 19F:
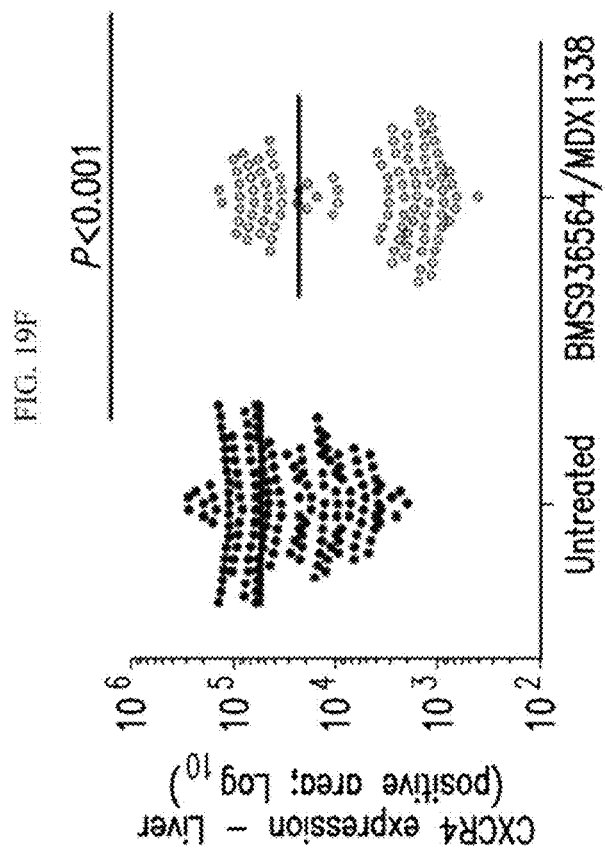
Figure 19E:
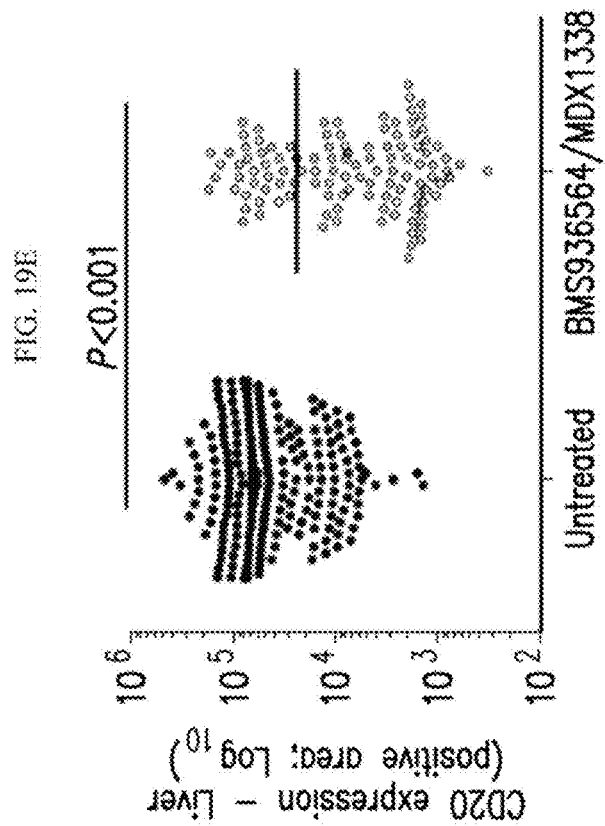
Figure 19H:
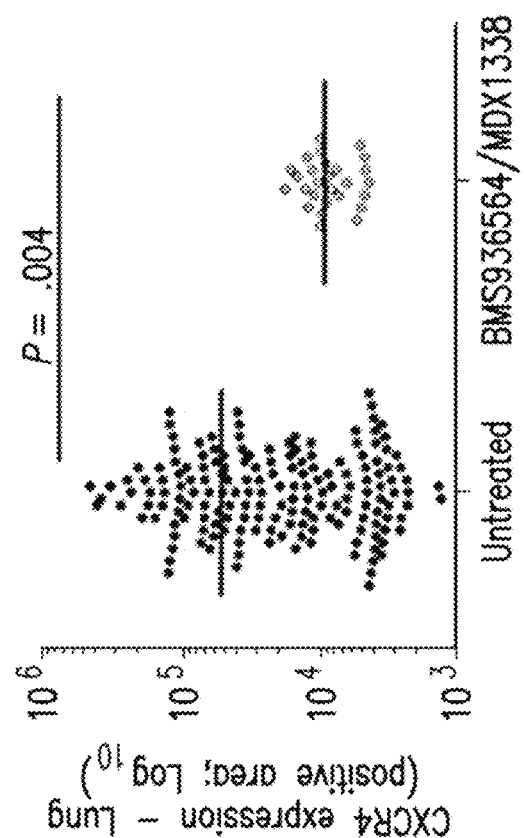
Figure 19G:
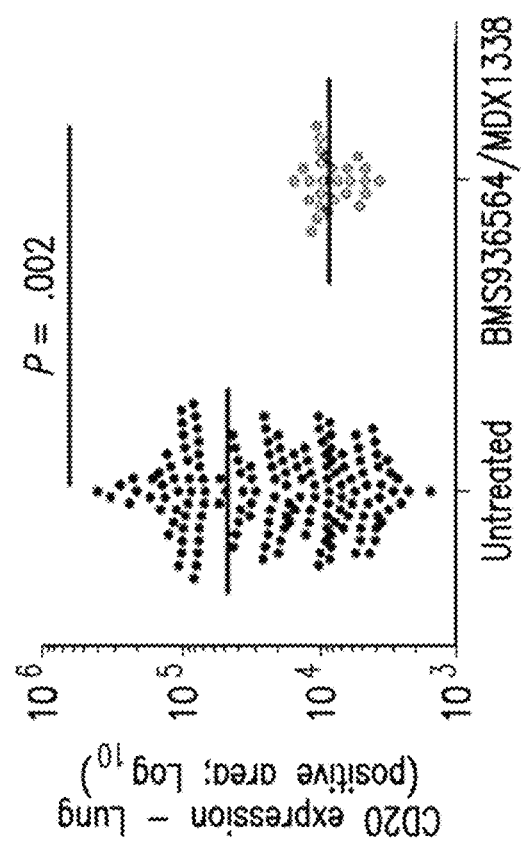
Figure 19J:
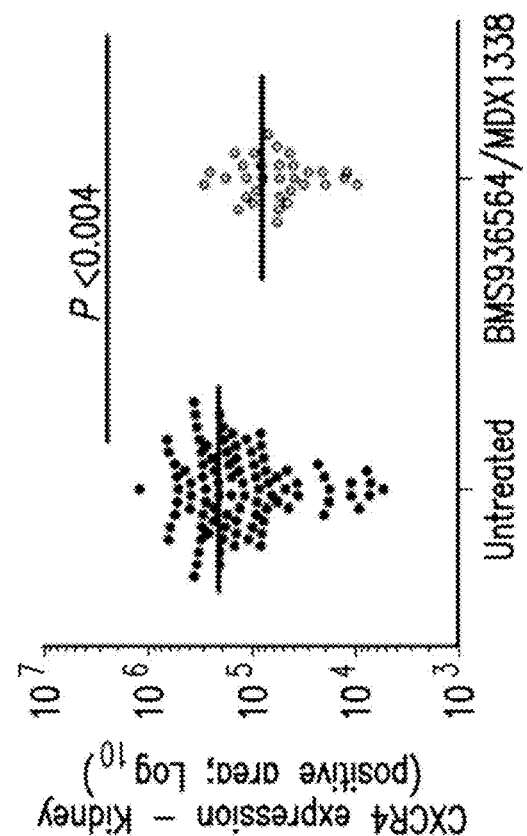
Figure 19I:
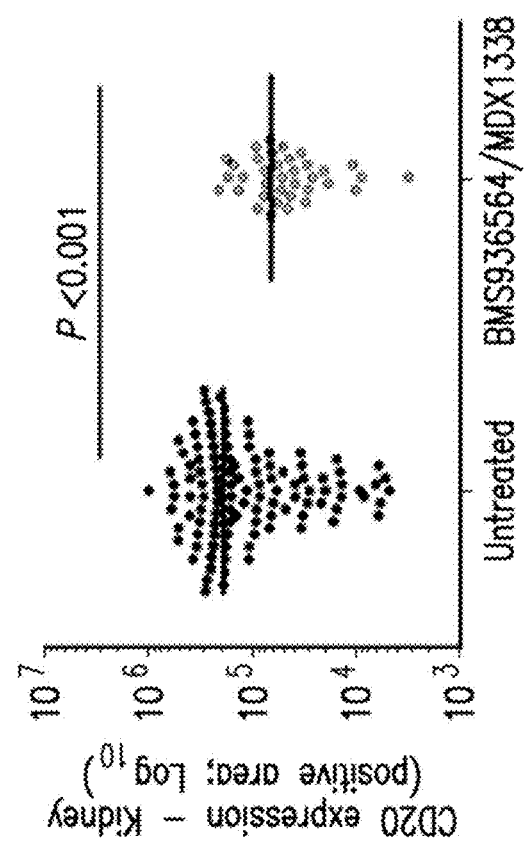

BMS-936564 may exert a pro-apoptotic effect in B-cell malignancies (WO 2013/071068; Kuhne et al., 2013). WM cells were therefore exposed to BMS-936564, which resulted in an increase of caspase-9 and PARP cleavage (FIG. 18).

The interaction between SDF 1/CXCR4 and β-catenin has been previously shown in models of metastatic solid tumors (Wang et al., 2011). In addition, phosphorylated-GSK3β is known to facilitate β-catenin degradation (Wang et al., 2011; Polakis, 2001). The effect of BMS-936564 on β-catenin was therefore investigated. It was found that by neutralizing CXCR4 with BMS-936564, WM cells present with increased phospho(p)-GSK3-β, and p-β-catenin up-regulation, leading to β-catenin degradation (FIG. 19). These findings may explain, at least in part, the possible mechanisms of BMS-936564-induced apoptosis in WM cells.

Example 6

Effect of BMS-936564 on C1013G/CXCR4-WM Cells In Vitro and In Vivo

In Vivo Studies

SCID/Bg mice (n=5/group) were injected with BCWM.1 infected with either precision LentiORF/CXCR4/GFP (CXCR4+)- or empty vector probe/RFP (control)-infected BCWM.1 cells. After three weeks, mice were euthanized and organs harvested. Hematoxylin-eosin staining, immunohistochemistry for human-CD20 and -CXCR4 were performed on explanted organs. Independent experiments were conducted to evaluate differences in survival (SCID/Bg mice, n=7/group). Similar studies were conducted using C1013/CXCR4-mutated cells and control vector-infected cells (control cells). In vivo homing studies were performed using BCWM.1-mCherry+ cells: cells were injected intravenously into SID/Bg mice and treated with either BMS-936564 or control antibody (10 mg/kg, intraperitoneally; 3-4 times per week for 3 weeks). The ability of BMS-936564 to modulate WM homing to BM, spleen and lymph nodes was evaluated ex vivo at the third week on explanted tissues, by using a fluorescence microscope (Nikon Eclipse 80i, Melville, N.Y.) (Roccaro et al., 2013).

The activity of BMS-936564 was tested in SCID/Bg mice injected with C1013G/CXCR4-mutated cells. Mice controls were treated with isotype control antibody (n=5 mice/group; BMS-936564 or control antibody (10 mg/kg, intraperitoneally; 3-4 times per week for 3 weeks).

Results

Figure 20A:
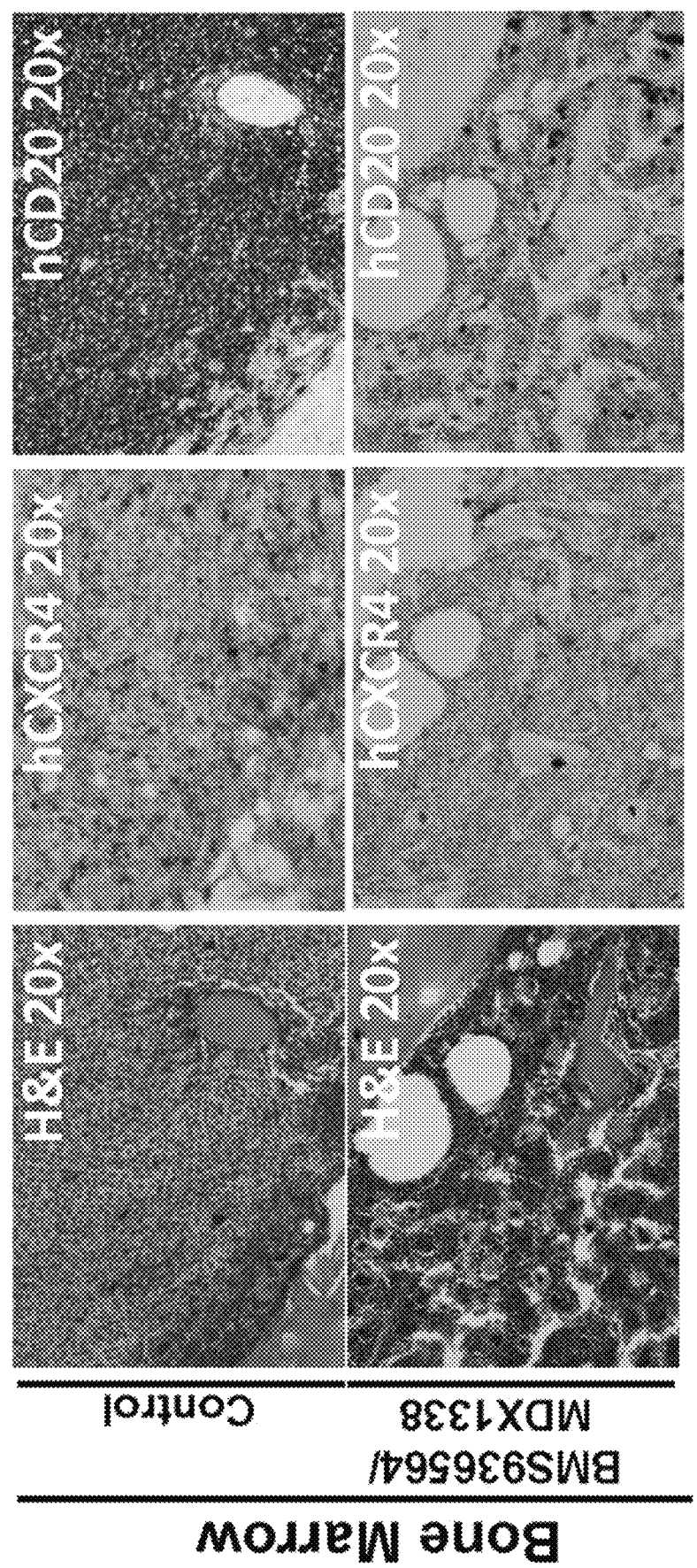
FIGS. 20A-20E.
Figure 20B:
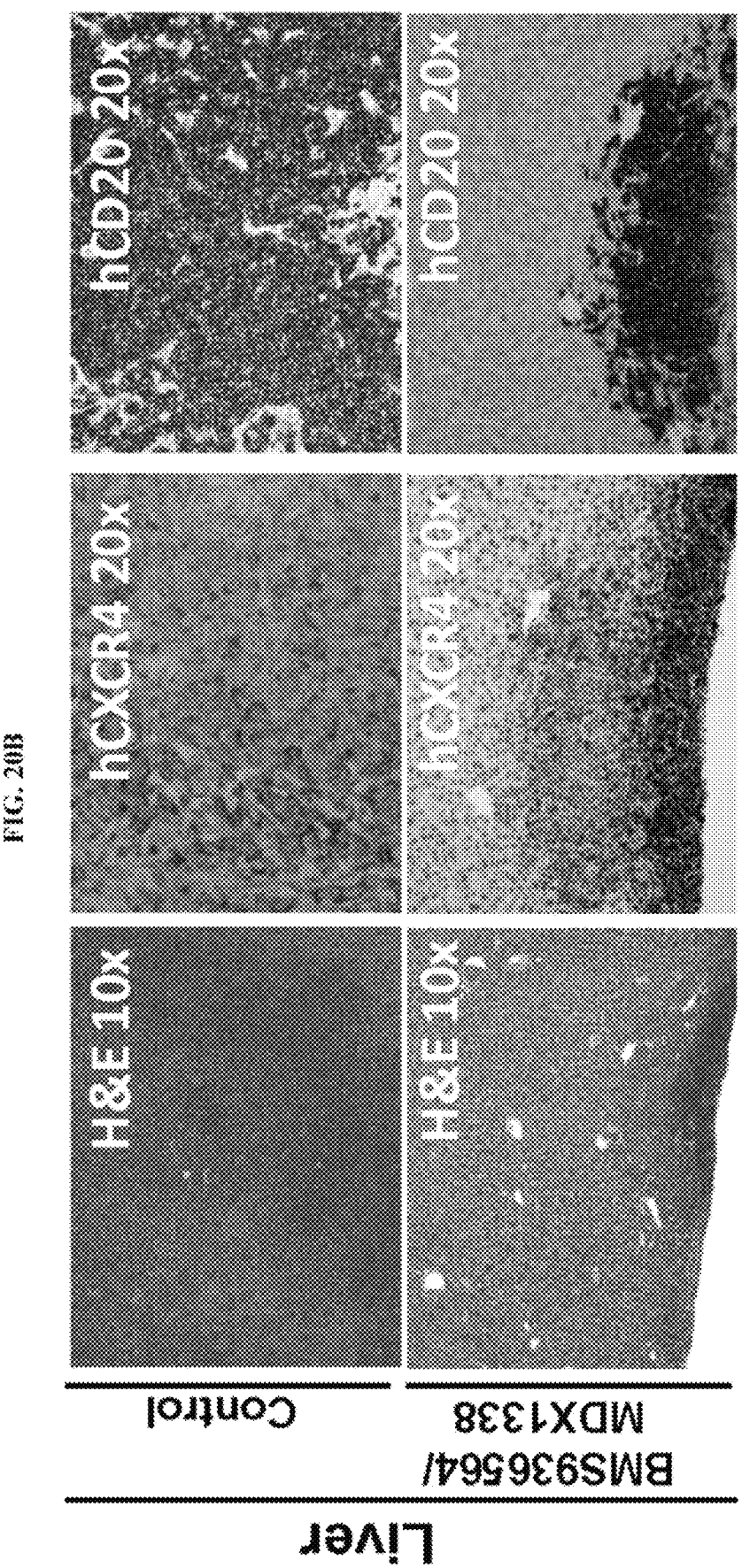
Figure 20C:
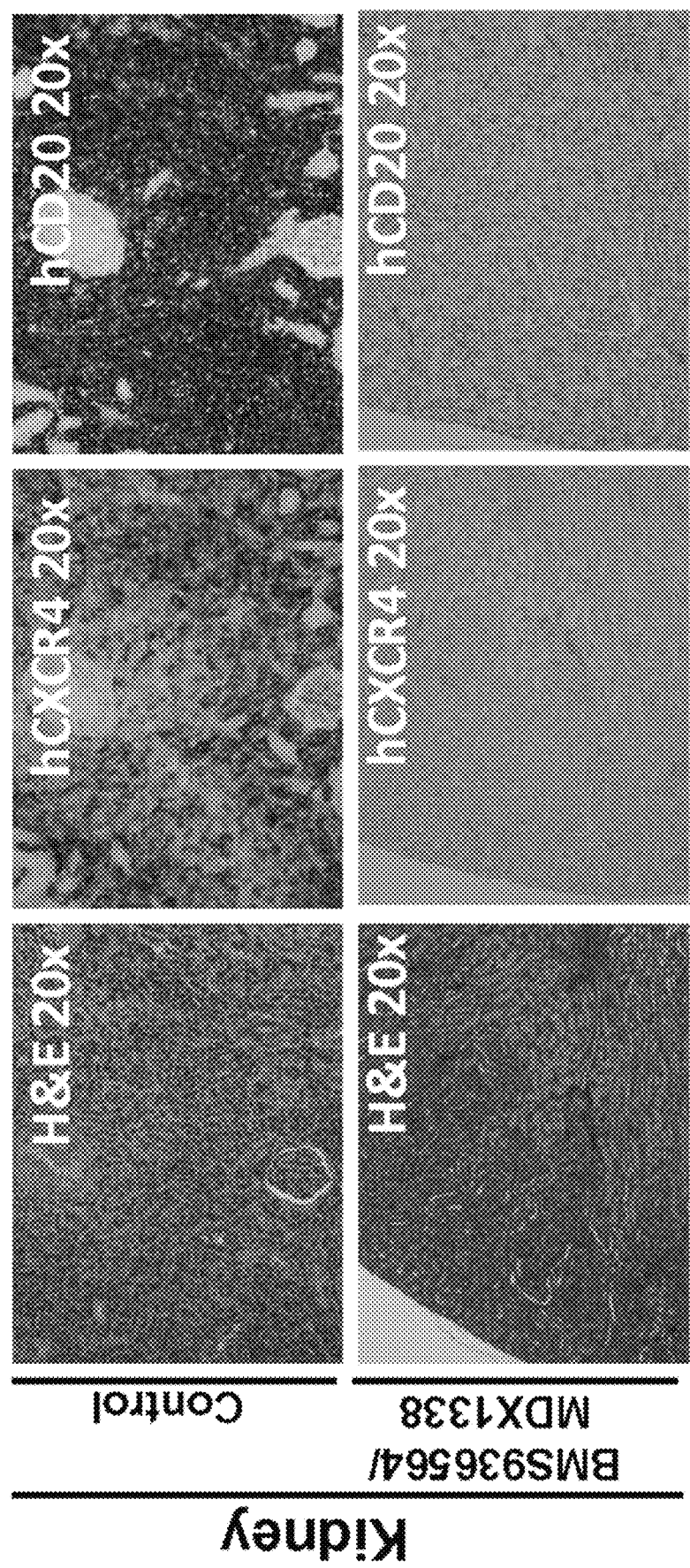
Figure 20D:
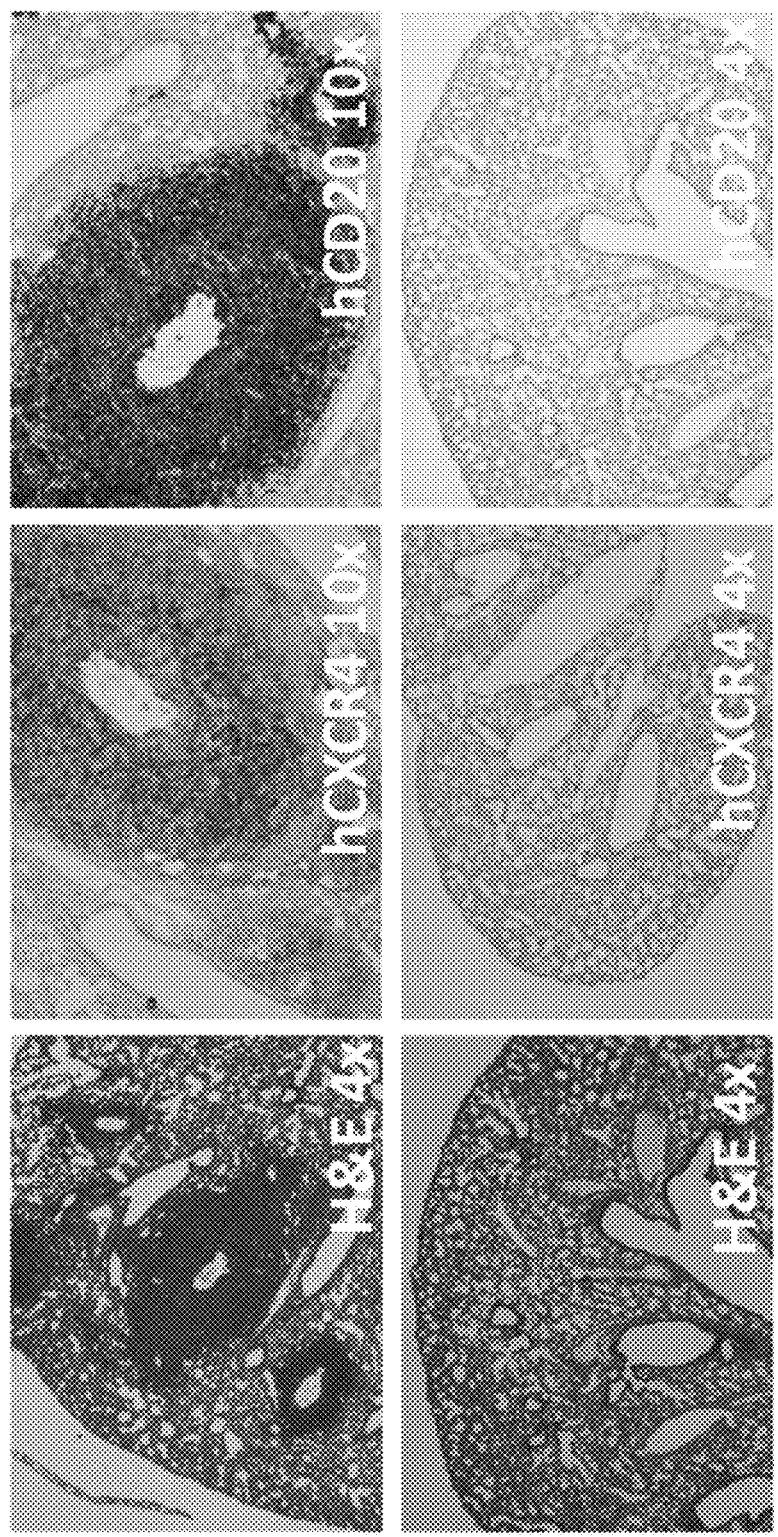
Figure 20E:
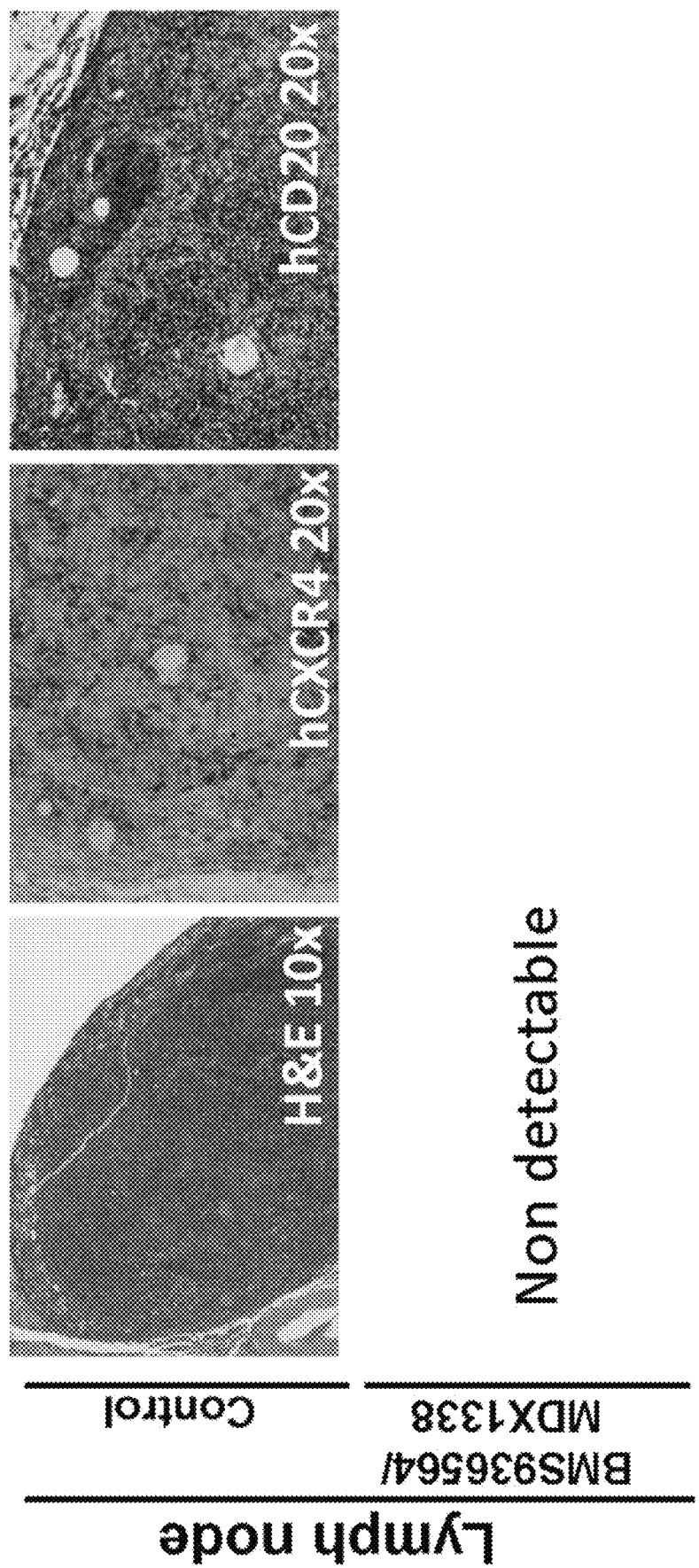
Figure 21A:
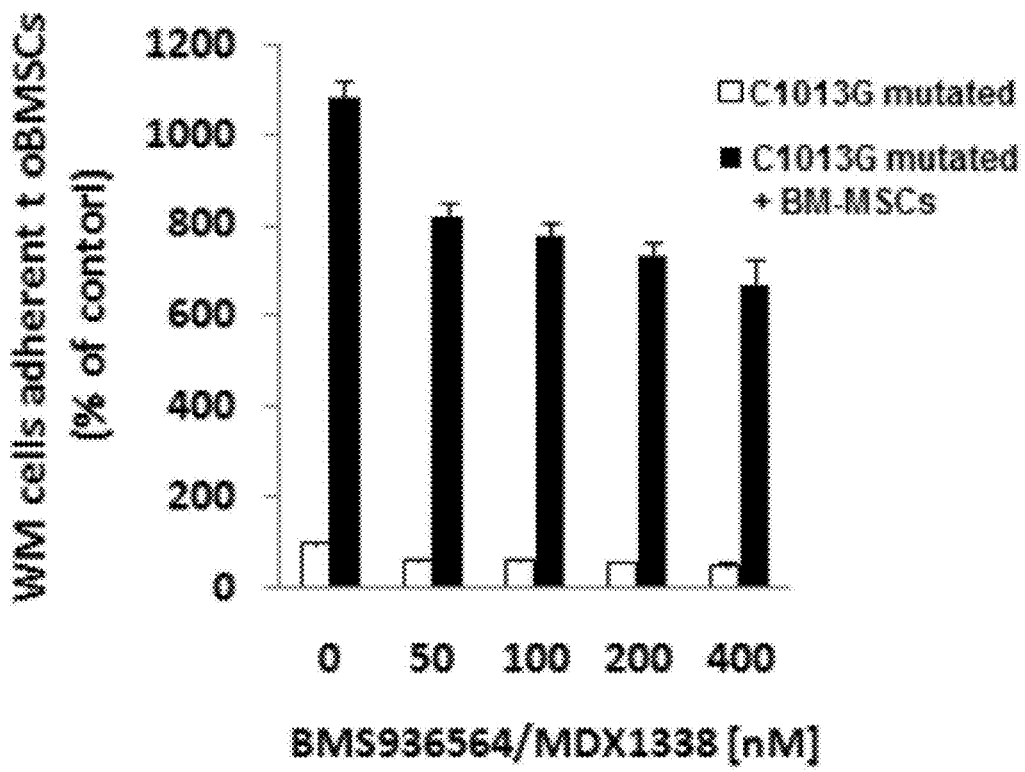
FIGS. 21A-21D.
Figure 21B:
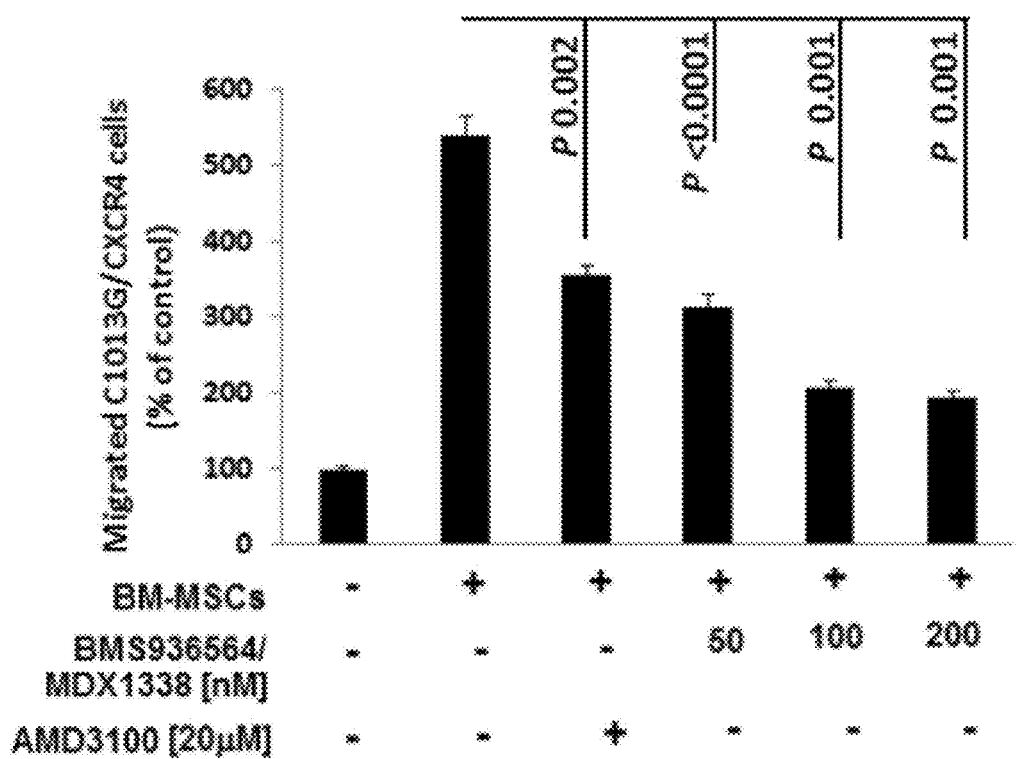
Figure 21C:
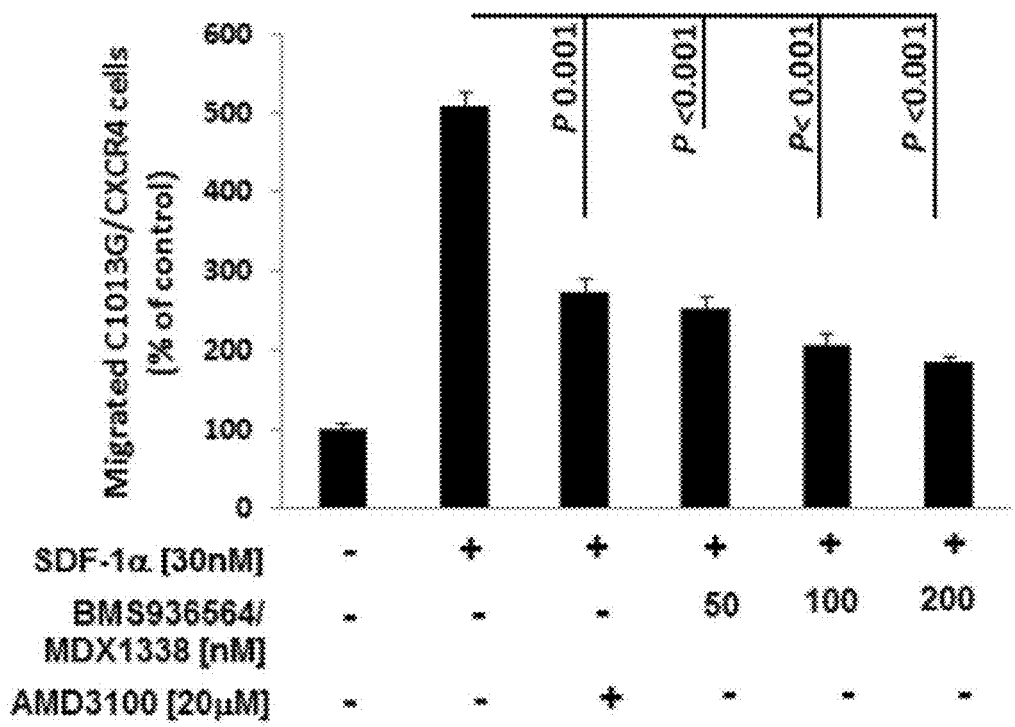
Figure 21D:
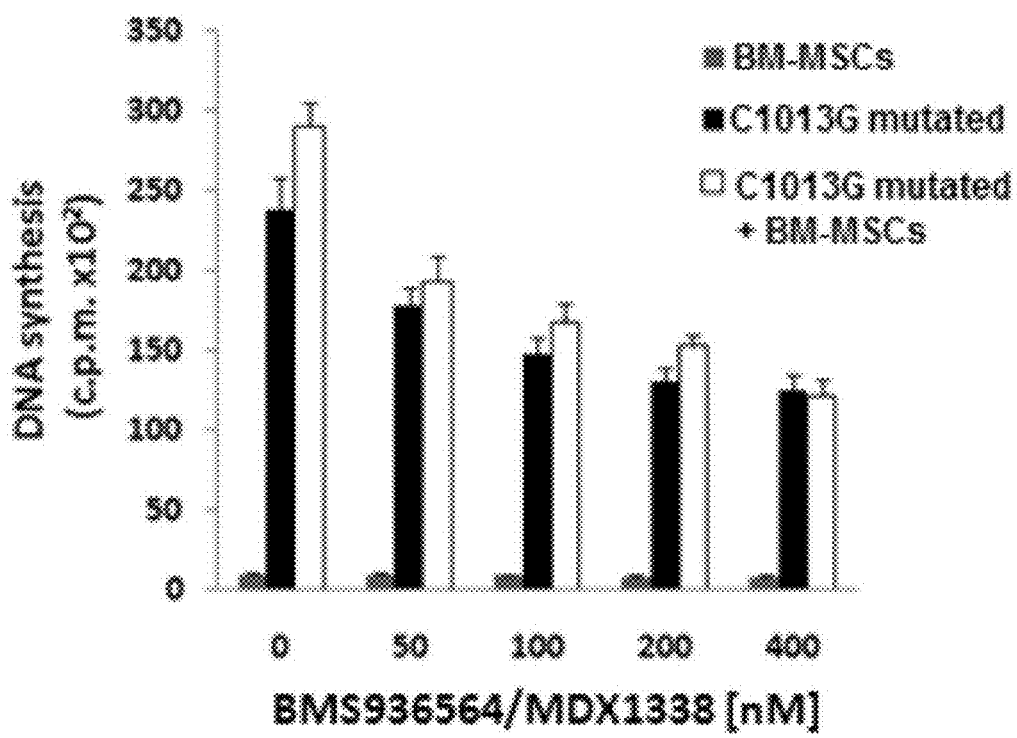

The effect of BMS-936564 on CXCR4-mutated WM cells was examined in vivo. BMS-936564 inhibited WM dissemination in mice injected with C1013G/CXCR4 WM cells as shown by significant reduction of CXCR4+/CD20+ cell infiltration in femur, liver, kidney and lung in treated mice compared to control antibody-treated mice (FIGS. 19A-E; FIGS. 20A-D). Importantly, involvement of lymph nodes was absent in mice treated with BMS-936564 (FIG. 20E).

These findings were further confirmed in vitro. BMS-936564 was found to be equally active in targeting adhesion, migration and proliferative properties of CXCR4-mutated cells in the context of the BM microenvironment (FIGS. 21A-D).

Figures 22A, 22B, 22C:
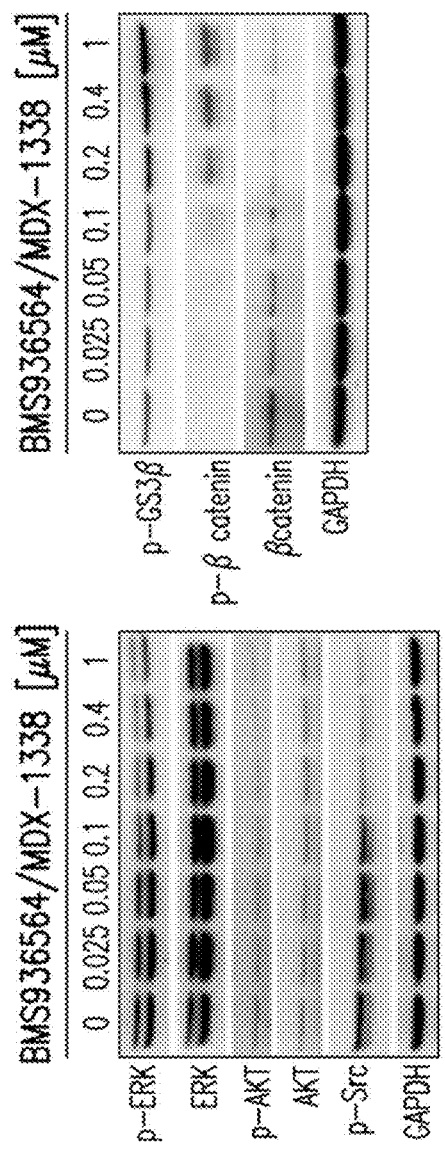
FIGS. 22A-22C.

Importantly, BMS-936564 increased caspase-9- and PARP-cleavage in CXCR4-mutated WM cells; and also modulated GSK3-β/β-catenin signaling, leading to up-regulation of p-GSK3-β/p-β-catenin and β-catenin degradation (FIG. 22). In addition, BMS-936564 induced a dose-dependent inhibition of p-ERK, p-Akt, and p-Src in WM cells harboring the C1013G/CXCR4 mutation (FIG. 22).

Example 7

Effect of BMS-936564 on Wild-Type WM Cells In Vivo

The anti-WM activity of BMS-936564 was also tested in vivo using wild-type WM cells. BCWM.1-mCherry+ cells were injected intravenously into SCID/Bg mice and treated mice with either BMS-936564 or control antibody. Immunofluorescence imaging of harvested BM, spleen and lymph nodes demonstrated the ability of BMS-936564 to inhibit WM cell dissemination ex vivo (data not shown; Roccaro et al., 2014).

As CXCR4 inhibition is thought to induce stem cell and tumor cell mobilization, it was hypothesized that BMS-936564 may also induce mobilization of WM cells leading to increased chemosensitivity to anti-WM agents. Accordingly, the effect of BMS-936564 in modulating tumor progression and WM cell dissemination to distant BM niches in vivo was evaluated as monotherapy or in combination with bortezomib. (Bortezomib was obtained from Hospital Pharmacy, diluted in DMSO and stored at −20° C. until use, then diluted in culture medium immediately before use. The maximum final concentration of DMSO (<0.1%) did not affect cell proliferation and did not induce cytotoxicity on the cell lines tested (data not shown).)

Figure 23A:
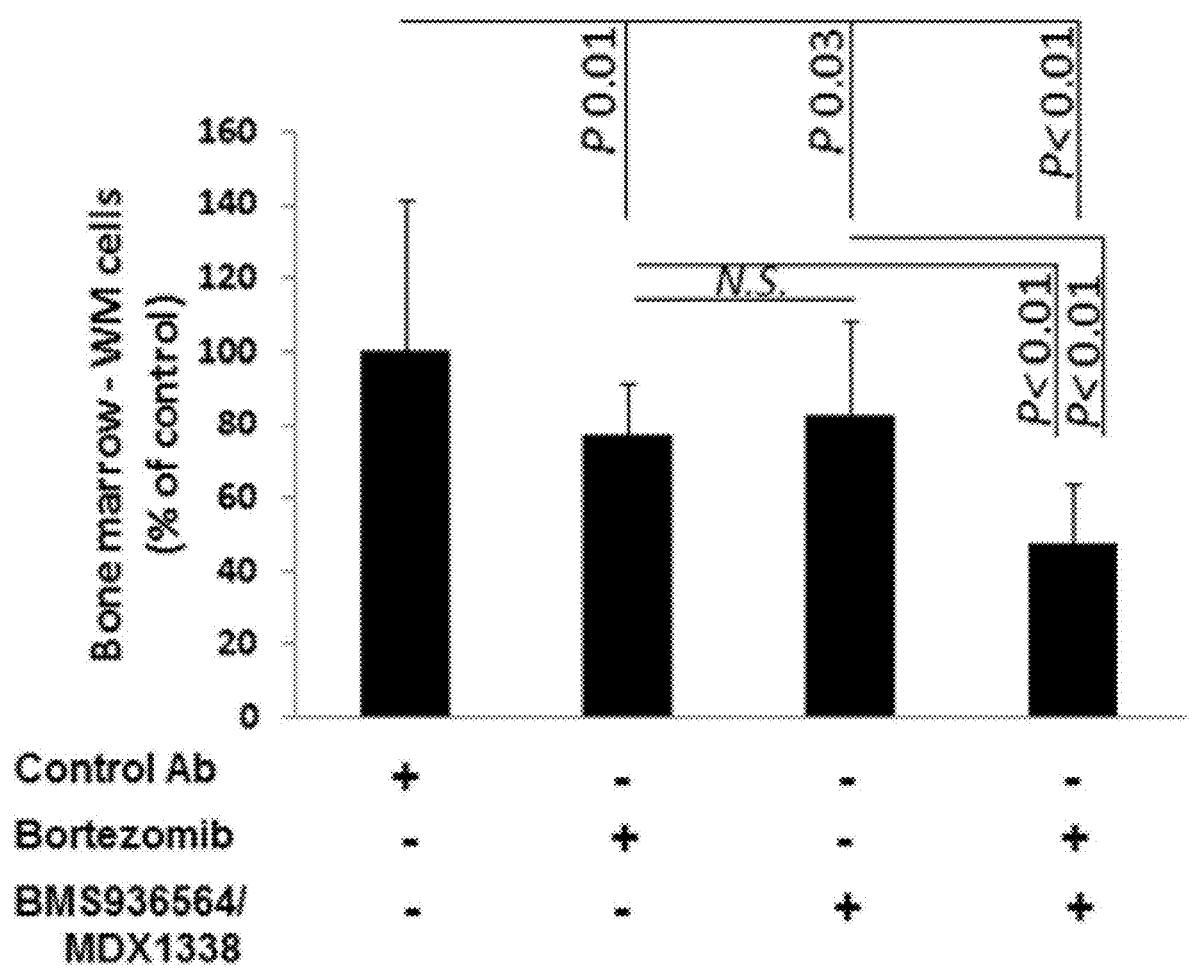
FIGS. 23A-23F.
Figure 23B:
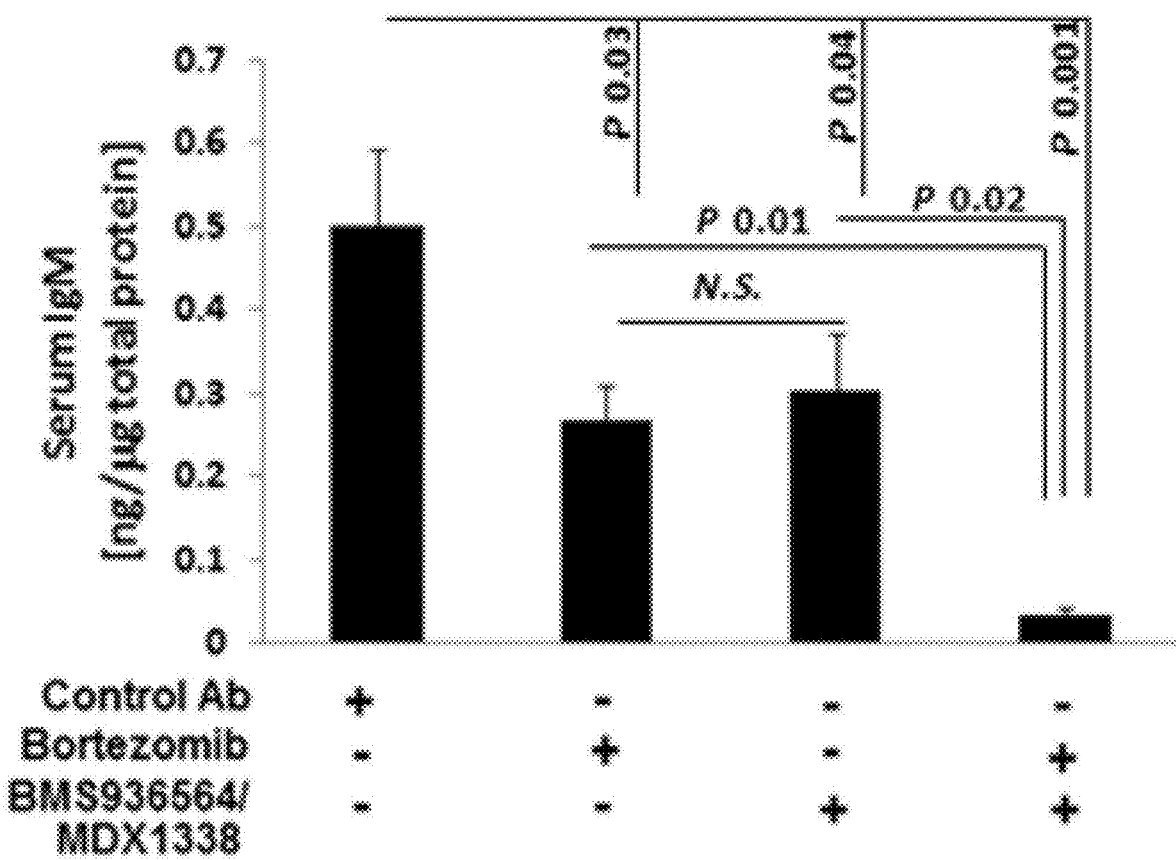
Figure 23C:
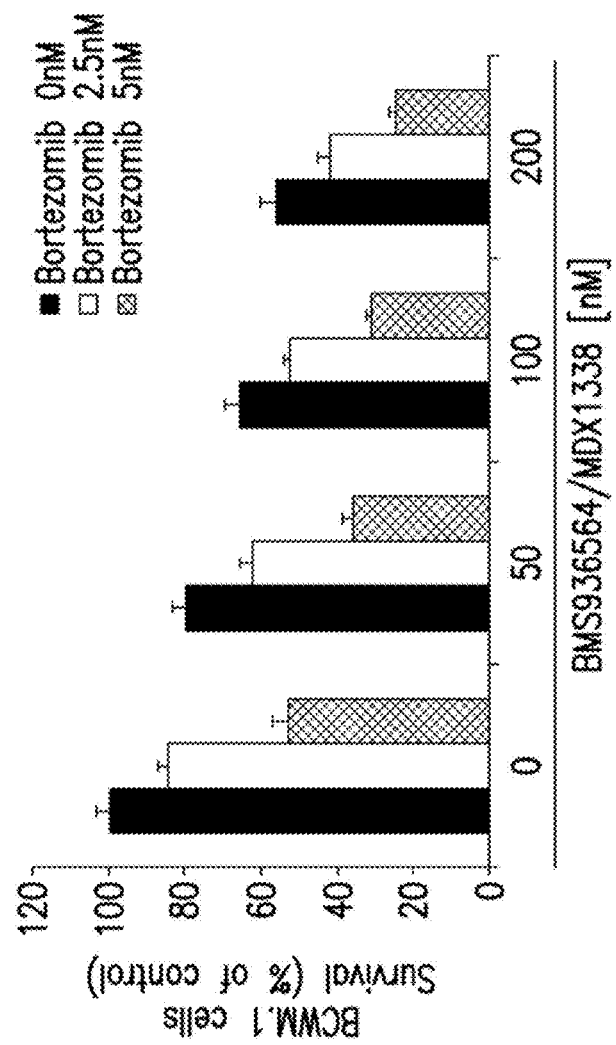
Figure 23D:
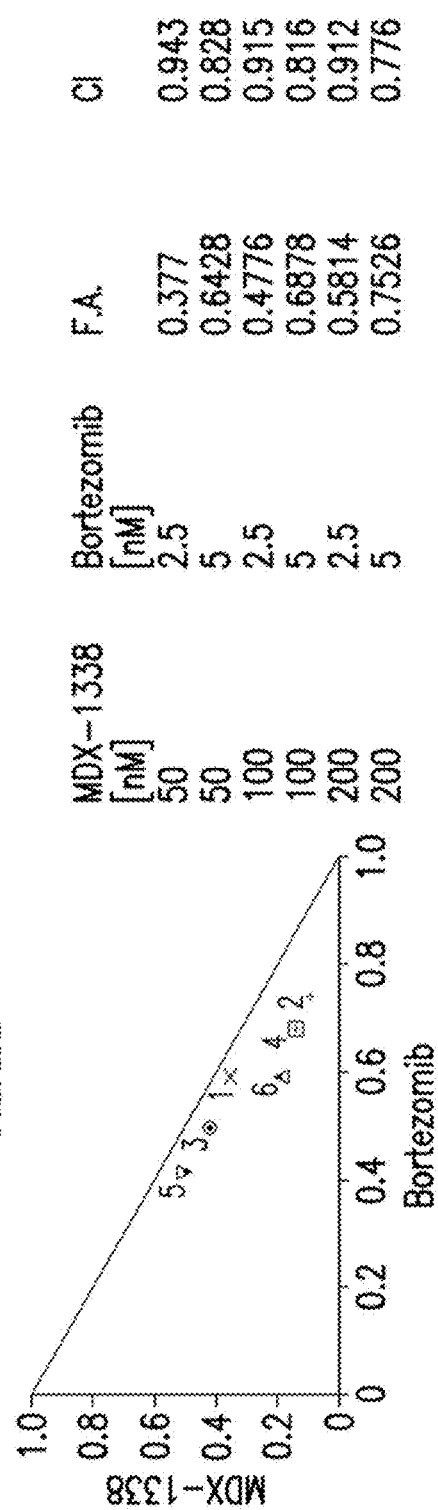
Figure 23E:
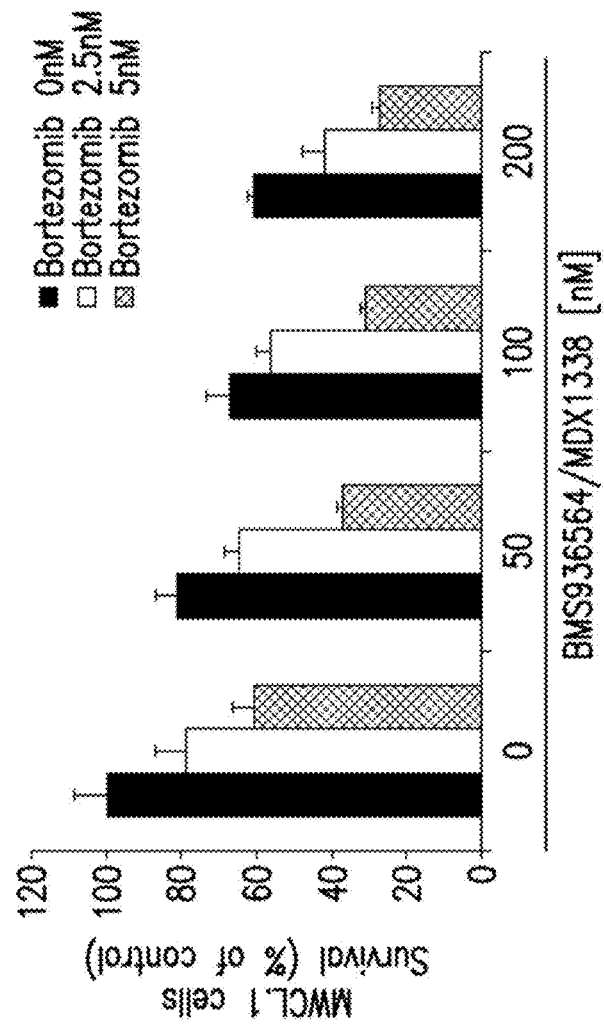
Figure 23F:
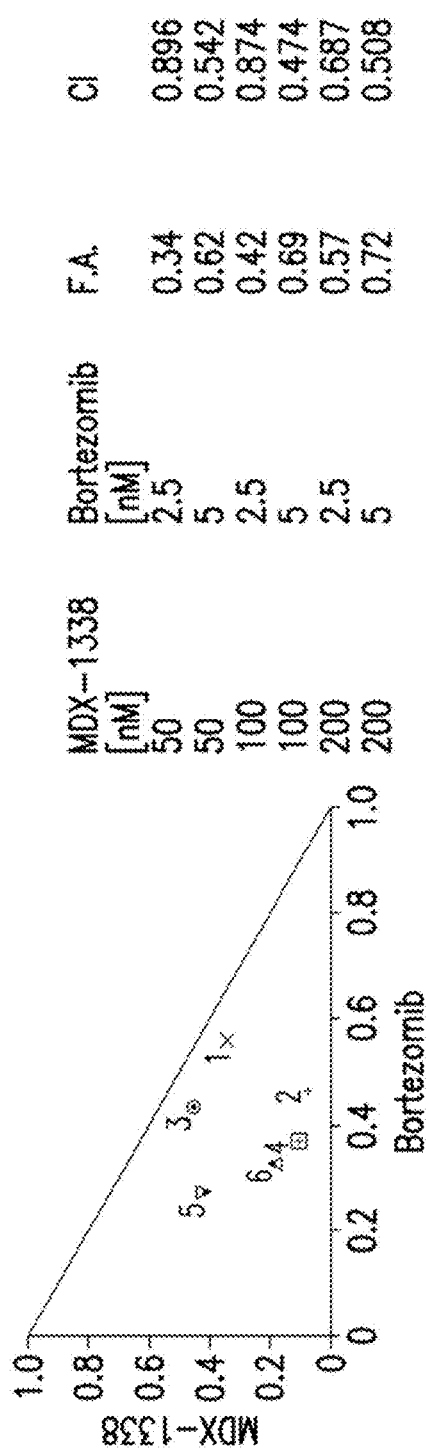

BMS-936564-treated mice presented with a significant reduction of tumor cells within the BM, with similar effects observed in the bortezomib-treated mice, and with a more significant inhibition in the mice treated with a combination of BMS-936564 and bortezomib (P<0.05; FIG. 23A). Similarly, serum IgM levels were significantly reduced when mice were treated with either BMS-936564 or bortezomib, but were even more significant reduced in the mice exposed to both BMS-936564 and bortezomib (P<0.05; FIG. 23B). Further examination of the combined effects of BMS-936564 and bortezomib in inducing toxicity in WM cells confirmed a synergistic interaction in vitro (FIGS. 23C, D).

REFERENCES

Alapi K et al. (2007) Recurrent CXCR4 sequence variation in a girl with WHIM syndrome. *Eur J Haematol.* 78(1): 86-8.

Alsayed Y et al. (2007) Mechanisms of regulation of CXCR4/SDF-1 (CXCL12)-dependent migration and homing in multiple myeloma. *Blood* 109(7): 2708-17.

Azab A K et al. (2009) CXCR4 inhibitor AMD3100 disrupts the interaction of multiple myeloma cells with the bone marrow microenvironment and enhances their sensitivity to therapy. *Blood* 113: 4341-51.

Azab F et al. (2012) Eph-B2/ephrin-B2 interaction plays a major role in the adhesion and proliferation of Waldenström's macroglobulinemia. *Clin Cancer Res* 18(1):91-104.

Balabanian K. et al. (2005) WHIM syndromes with different genetic anomalies are accounted for by impaired CXCR4 desensitization to CXCL12. *Blood* 105: 2449-57.

Balabanian K et al. (2008) Leukocyte analysis from WHIM syndrome patients reveals a pivotal role for GRK3 in CXCR4 signaling. *J Clinical Invest* 118: 1074-84.

Bertolini F et al. (2002) CXCR4 neutralization, a novel therapeutic approach for non-Hodgkin's lymphoma. *Cancer Res* 62(11): 3106-12.

Burger J A et al. (1999) Chronic lymphocytic leukemia B cells express functional CXCR4 chemokine receptors that mediate spontaneous migration beneath bone marrow stromal cells. *Blood* 94: 3658-67.

Campo E et al. (2011) The 2008 WHO classification of lymphoid neoplasms and beyond: evolving concepts and practical applications. *Blood* 117: 5019-32.

Cao Y et al. (2012) Whole genome sequencing identifies recurring somatic mutations in the C-terminal domain of CXCR4, including a gain of function mutation in Waldenstrom's macroglobinemia. *Blood* 120: Abstract.

Cao Y et al. (2013) Somatic activating mutations in CXCR4 are common in patients with Waldenstrom's macroglobulinemia, and their expression in WM cells promotes resistance to ibrutinib. [abstract]. *Blood* 122(21): Abstract 4424.

Chng W J et al. (2008) Gene-expression profiling of Waldenström macroglobulinemia reveals a phenotype more similar to chronic lymphocytic leukemia than multiple myeloma. *Blood* 108(8):2755-63.

Crazzolara R et al. (2001) High expression of the chemokine receptor CXCR4 predicts extramedullary organ infiltration in childhood acute lymphoblastic leukaemia. *Br J Haematol* 115: 545-53.

Dar A et al. (2011) Rapid mobilization of hematopoietic progenitors by AMD3100 and catecholamines is mediated by CXCR4-dependent SDF-1 release from bone marrow stromal cells. *Leukemia* 25(8): 1286-96.

Dimopoulos M A et al. (2007) Primary treatment of Waldenström macroglobulinemia with dexamethasone, rituximab, and cyclophosphamide. *J Clin Oncol* 25(22): 3344-9.

Downward J (2003) Targeting RAS signalling pathways in cancer therapy. *Nat Rev Cancer* 3(1):11-22.

Geminder et al. (2001) A possible role for CXCR4 and its ligand, the CXC chemokine stromal cell-derived factor-1, in the development of bone marrow metastases in neuroblastoma. *J Immunol* 167: 4747-57.

Ghobrial I M et al. (2003) Waldenstrom macroglobulinaemia. *Lancet Oncol* 4: 679-85.

Gutiérrez N C et al. (2007) Gene expression profiling of B lymphocytes and plasma cells from Waldenström's macroglobulinemia: comparison with expression patterns of the same cell counterparts from chronic lymphocytic leukemia, multiple myeloma and normal individuals. *Leukemia* 21(3):541-49.

Hernandez P A et al. (2003) Mutations in the chemokine receptor gene CXCR4 are associated with WHIM syndrome, a combined immunodeficiency disease. *Nature Genetics* 34: 70-4.

Hiller D J et al. (2011) Chemokine receptor CXCR4 level in primary tumors independently predicts outcome for patients with locally advanced breast cancer. *Surgery* 150(3): 459-65.

Hollinger et al. (2005) Engineered antibody fragments and the rise of single domains. *Nature Biotech* 23(9): 1126-36.

Hsieh A C et al. (2012) The translational landscape of mTOR signalling steers cancer initiation and metastasis. *Nature* 485: 55-61.

Hunter Z et al. (2014) The genomic landscape of Waldenström macroglobulinemia is characterized by highly recurring MYD88 and WHIM-like CXCR4 mutations, and small somatic deletions associated with B-cell lymphomagenesis. *Blood* 123(11):1637-46.

Hwang J H et al. (2003) CXC chemokine receptor 4 expression and function in human anaplastic thyroid cancer cells. *J Clin Endocrinol Metab* 88:408-16.

Jiang Y P et al. (2006) Expression of chemokine CXCL12 and its receptor CXCR4 in human epithelial ovarian cancer: an independent prognostic factor for tumor progression. *Gynecol Oncol* 103(1): 226-33.

Jin L et al. (2008) CXCR4 up-regulation by imatinib induces chronic myelogenous leukemia (CML) cell migration to bone marrow stroma and promotes survival of quiescent CML cells. *Mol Cancer Ther* 7: 48-58.

Johnson J and Wu T T (2000) Kabat Database and its applications: 30 years after the first variability plot. *Nucl Acids Res* 28(1): 214-8.

Kabat E A et al. (1991) *Sequences of Proteins of Immunological Interest*, Fifth Edition, U.S. Department of Health and Human Services, NIH Publication No. 91-3242.

Koshiba T et al. (2000) *Clin Cancer Res* 6: 3530-5.

Kuhne M R et al. (2013) BMS-936564/MDX-1338: a fully human anti-CXCR4 antibody induces apoptosis in vitro and shows antitumor activity in vivo in hematologic malignancies. *Clin Cancer Res* 19: 357-66.

Laverdiere C et al. (2005) Messenger RNA expression levels of CXCR4 correlate with metastatic behavior and outcome in patients with osteosarcoma. *Clin Cancer Res* 11: 2561-7.

Leleu X et al. (2008) Targeting NF-κB in Waldenström's macroglobulinemia. *Blood* 111(10):5068-77.

Libura J et al. (2002) CXCR4-SDF-1 signaling is active in rhabdomyosarcoma cells and regulates locomotion, chemotaxis, and adhesion. *Blood* 100: 2597-606.

Lim K H and Counter C M (2005) Reduction in the requirement of oncogenic Ras signaling to activation of PI3K/AKT pathway during tumor maintenance. *Cancer Cell* 8(5):381-92.

Marechal R et al. (2009) High expression of CXCR4 may predict poor survival in resected pancreatic adenocarcinoma. *Brit J Cancer* 100(9): 1444-51.

Mohle R et al. (1998) The chemokine receptor CXCR-4 is expressed on CD34+ hematopoietic progenitors and leukemic cells and mediates transendothelial migration induced by stromal cell-derived factor-1. *Blood* 91(12): 4523-30.

Mohle R et al. (1999) Overexpression of the chemokine receptor CXCR4 in B cell chronic lymphocytic leukemia is associated with increased functional response to stromal cell-derived factor-1 (SDF-1). *Leukemia* 13: 1954-9.

Muller A et al. (2001) Involvement of chemokine receptors in breast cancer metastasis. *Nature* 410: 50-6.

Murphy P M (2001) Chemokines and the molecular basis of cancer metastasis. *New Engl J Med* 345(11): 833-5.

Ngo H T et al. (2008) SDF-1/CXCR4 and VLA-4 interaction regulates homing in Waldenstrom macroglobulinemia. *Blood* 112: 150-8.

Olafsen et al. (2010) Antibody vectors for imaging. *Semin Nucl Med* 40(3): 167-81.

Ottaiano A et al. (2006) Overexpression of both CXC chemokine receptor 4 and vascular endothelial growth factor proteins predicts early distant relapse in stage II-III colorectal cancer patients. *Clin Cancer Res* 12(9): 2795-803.

Paiva B et al. (2013) Multiparameter flow cytometry for the identification of the Waldenstrom's clone in IgM-MGUS and Waldenstrom's Macroglobulinemia: new criteria for differential diagnosis and risk stratification. *Leukemia* 28(1): 166-73.

PCT Publication No. WO 2008/060367, published May 22, 2008 by Medarex, Inc.

PCT Publication No. WO 2013/071068, published May 16, 2013 by Bristol-Myers Squibb Co.

Polakis P (2001) More than one way to skin a catenin. *Cell* 105: 563-6.

Rempel S A et al. (2000) Identification and localization of the cytokine SDF 1 and its receptor, CXC chemokine receptor 4, to regions of necrosis and angiogenesis in human glioblastoma. *Clin Cancer Res* 6: 102-11.

Rizki A et al. (2008) A human breast cell model of preinvasive to invasive transition. *Cancer Res* 68: 1378-87.

Roccaro A M et al. (2008) Dual targeting of the proteasome regulates survival and homing in Waldenstrom macroglobulinemia. *Blood* 111: 4752-63.

Roccaro A M et al. microRNA expression in the biology, prognosis, and therapy of Waldenström macroglobulinemia. *Blood* 113(18):4391-402.

Roccaro A M et al. (2010) Dual targeting of the PI3K/Akt/mTOR pathway as an antitumor strategy in Waldenstrom macroglobulinemia. *Blood* 115: 559-69.

Roccaro A M et al. (2013) BM mesenchymal stromal cell-derived exosomes facilitate multiple myeloma progression. *J Clin Invest* 123: 1542-55.

Roccaro A M et al. (2014) C1013G/CXCR4 acts as a driver mutation of tumor progression and modulator of drug resistance in lymphoplasmacytic lymphoma. *Blood* 123 (26):4120-31.

Rombouts E J C et al. (2004) Relation between CXCR-4 expression, Flt3 mutations, and unfavorable prognosis of adult acute myeloid leukemia. *Blood* 104: 550-7.

Sacco A et al. (2011) Carfilzomib-dependent selective inhibition of the chymotrypsin-like activity of the proteasome leads to antitumor activity in Waldenstrom's Macroglobulinemia. *Clin Cancer Res* 17: 1753-64.

Scala S et al. (2005) Expression of CXCR4 predicts poor prognosis in patients with malignant melanoma. *Clin Cancer Res* 11: 1835-41.

Schrader A J et al. (2002) CXCR4/CXCL12 expression and signalling in kidney cancer. *Br J Cancer* 86: 1250-6.

Scotton C et al. (2001) Analysis of CC chemokine and chemokine receptor expression in solid ovarian tumours. *Br J Cancer* 85: 891-7.

Spano J P et al. (2004) Chemokine receptor CXCR4 and early-stage non-small cell lung cancer: pattern of expression and correlation with outcome. *Ann Oncol* 15: 613-7.

Spoo A C et al. (2007) CXCR4 is a prognostic marker in acute myelogenous leukemia. *Blood* 109(2): 786-91.

Staller P et al. (2003) Chemokine receptor CXCR4 downregulated by von Hippel-Lindau tumour suppressor pVHL. *Nature* 425: 307-11.

Subramanian A et al. (2005) Gene set enrichment analysis: a knowledge-based approach for interpreting genomewide expression profiles. *Proc Natl Acad Sci USA* 102: 15545-50.

Taichman R S et al. (2002) Use of the stromal cell-derived factor-1/CXCR4 pathway in prostate cancer metastasis to bone. *Cancer Res* 62: 1832-7.

Taniuchi S et al. (2005) The role of a mutation of the CXCR4 gene in WHIM syndrome. *Haematologica* 90: 1271-2.

Treon S P (2009) How I treat Waldenström macroglobulinemia. *Blood* 114(12): 2375-85.

Treon S P et al. (2009) Primary therapy of Waldenström macroglobulinemia with bortezomib, dexamethasone, and rituximab: WMCTG clinical trial 05-180. *J Clin Oncol* 27(23): 3830-5.

Treon S P et al. (2012) MYD88/L265P somatic mutation in Waldenström's macroglobulinemia. *N Engl J Med* 367 (9):826-33.

Treon S P et al. (2013) A prospective multicenter study of the bruton's tyrosine kinase inhibitor ibrutinib in patients with relapsed or refractory Waldenström's macroglobulinemia [abstract]. *Blood* 122(21): Abstract 251.

Treon S P et al. (2014) Somatic mutations in MYD88 and CXCR4 are determinants of clinical presentation and overall survival in Waldenström's macroglobulinemia *Blood.* 123(18):2791-6.

van Dongen J J et al. (2012) EuroFlow antibody panels for standardized n-dimensional flow cytometric immunophenotyping of normal, reactive and malignant leukocytes. *Leukemia* 26: 1908-75.

Vijay A and Gertz M A (2007) Waldenstrom macroglobulinemia. *Blood* 109: 5096-113.

Wang N et al. (2005) Expression of chemokine receptor CXCR4 in nasopharyngeal carcinoma: pattern of expression and correlation with clinical outcome. *J Transl Med* 3: 26-33.

Wang L et al. (2011) Influence of CXCR4/SDF-1 axis on E-cadherin/beta-catenin complex expression in HT29 colon cancer cells. *World J Gastroenterol* 17: 625-32.

Wang W et al. (2007) Coordinated regulation of pathways for enhanced cell motility and chemotaxis is conserved in rat and mouse mammary tumors. *Cancer Res* 67: 3505-11.

Weng A P et al. (2003) CXCR4/CD184 immunoreactivity in T-cell non-Hodgkin lymphomas with an overall Th1-Th2+ immunophenotype. *Am J Clin Pathol* 119: 424-30.

Yang G et al. (2013) A mutation in MYD88 (L265P) supports the survival of lymphoplasmacytic cells by activation of Bruton tyrosine kinase in Waldenström's macroglobulinemia. *Blood* 122(7):1222-32.

Zeelenberg I S et al. (2003) The chemokine receptor CXCR4 is required for outgrowth of colon carcinoma micrometastases. *Cancer Res* 63: 3833-9.

Zeng Z et al. (2009) Targeting the leukemia microenvironment by CXCR4 inhibition overcomes resistance to kinase inhibitors and chemotherapy in AML. *Blood* 113 (24): 6215-24.

What is claimed is:

1. A method for treating a subject afflicted with C1013G/CXCR4-associated Waldenström's macroglobulinemia, which method comprises:
   (a) selecting a subject that is a suitable candidate for treatment, the selecting comprising:
      (i) assessing whether cells in a test tissue sample obtained from Waldenström's macroglobulinemia tissue in the subject carry the C1013G mutation in the C-X-C chemokine receptor type 4 (CXCR4) gene; and
      (ii) selecting the subject as a suitable candidate based on a determination that the Waldenström's macroglobulinemia cells carry the C1013G mutation in the CXCR4 gene; and
   (b) administering to the selected subject a therapeutically effective amount of an anti-CXCR4 antibody or an antigen-binding portion thereof that specifically binds to a CXCR4 receptor expressed on the surface of a C1013G/CXCR4-associated Waldenström's macroglobulinemia cell.

2. The method of claim 1, wherein:
   (a) the subject is a human and the anti-CXCR4 antibody or antigen-binding portion thereof binds to a human CXCR4 receptor carrying the C1013G mutation;
   (b) the anti-CXCR4 antibody or antigen-binding portion thereof is of a human IgG1, IgG2 or IgG4 isotype;
   (c) the anti-CXCR4 antibody or antigen-binding portion thereof is a monoclonal antibody or an antigen-binding portion thereof;
   (d) the anti-CXCR4 antibody or antigen-binding portion thereof is a chimeric, humanized or human antibody or an antigen-binding portion thereof; and/or
   (e) the anti-CXCR4 antibody or antigen-binding portion thereof induces apoptosis of a C1013G/CXCR4-expressing cell.

3. The method of claim 1, wherein the anti-CXCR4 antibody or antigen-binding portion thereof is administered as monotherapy.

4. The method of claim 1, wherein the anti-CXCR4 antibody or antigen-binding portion thereof inhibits the activity of the C1013G/CXCR4 receptor and increases sensitivity of the Waldenström's macroglobulinemia cell to an anti-cancer agent.

5. The method of claim 1, further comprising administering at least one anti-cancer agent in combination with the anti-CXCR4 antibody or antigen-binding portion thereof.

6. The method of claim 5, wherein the at least one anti-cancer agent is ibrutinib, bortezomib, carfilzomib, idelalisib, panobinostat, dexamethasone, rituximab, thalidomide, cyclophosphamide, lenalidomide, doxorubicin, vincristine, prednisone, fludarabine, chlorambucil, bendamustine, cladribine, alemtuzumab, ofatumumab, everolimus, cisplatin, bleomycin sulfate, carmustine, mitoxantrone, etoposide, cytarabine, ifosfamide, and carboplatin.

7. The method of claim 5, wherein the at least one anti-cancer agent is ibrutinib.

8. The method of claim 7, wherein ibrutinib is administered at a dose of 420 mg orally once a day.

9. The method of claim 1, wherein the anti-CXCR4 antibody or antigen-binding portion thereof is administered to the subject after failure of a prior treatment for Waldenström's macroglobulinemia.

10. The method of claim 9, wherein the prior treatment is with an agent selected from a mammalian target of rapamycin (mTOR) inhibitor, a Bruton's tyrosine kinase (BTK) inhibitor, and phosphatidylinositol 3-kinase (PI3K) inhibitor.

11. The method of claim 9, wherein the prior treatment is:
   (a) first-line treatment with ibrutinib;
   (b) first-line treatment with a BDR (bortezomib, dexamethasone and rituximab) regimen and second-line treatment with ibrutinib; or (c) first-line treatment with a RCD (cyclophosphamide, dexamethasone and rituximab) regimen and second-line treatment with ibrutinib.

12. The method of claim 1, wherein the anti-CXCR4 antibody or portion thereof comprises a heavy chain variable region CDR1 comprising consecutively linked amino acids having the sequence set forth in SEQ ID NO: 1, a heavy chain variable region CDR2 comprising consecutively linked amino acids having the sequence set forth in SEQ ID NO: 5, a heavy chain variable region CDR3 comprising consecutively linked amino acids having the sequence set forth in SEQ ID NO: 9, a light chain variable region CDR1 comprising consecutively linked amino acids having the sequence set forth in SEQ ID NO: 13, a light chain variable region CDR2 comprising consecutively linked amino acids having the sequence set forth in SEQ ID NO: 17, and a light chain variable region CDR3 comprising consecutively linked amino acids having the sequence set forth in SEQ ID NO: 21.

13. The method of claim 1, wherein the anti-CXCR4 antibody or portion thereof comprises:
 (a) a heavy chain variable region comprising consecutively linked amino acids having the sequence set forth in SEQ ID NO: 25, and a light chain variable region comprising consecutively linked amino acids having the sequence set forth in SEQ ID NO: 29; or
 (b) a heavy chain variable region comprising consecutively linked amino acids having the sequence set forth in SEQ ID NO: 41, and a light chain variable region comprising consecutively linked amino acids having the sequence set forth in SEQ ID NO: 45.

14. The method of claim 1, wherein the anti-CXCR4 antibody is ulocuplumab.

15. The method of claim 1, wherein the therapeutically effective amount of the anti-CXCR4 antibody or antigen-binding portion thereof:
 (a) comprises a dose ranging from 0.1 to 20 mg/kg body weight;
 (b) comprises a dose of 0.1, 0.3, 0.5, 1, 3, 5, 10 or 20 mg/kg body weight; and/or
 (c) is 3 or 10 mg/kg body weight.

16. The method of claim 1, wherein the anti-CXCR4 antibody or antigen-binding portion thereof is administered at a dosing schedule of once per week, once every two weeks, once every three weeks, or once a month.

17. The method of claim 1, wherein the anti-CXCR4 antibody or antigen-binding portion thereof is administered via intravenous or subcutaneous administration.

18. The method of claim 1, wherein the therapeutically effective amount of the antibody or antigen-binding portion thereof comprises a fixed dose.

19. The method of claim 18, wherein the fixed dose is:
 (a) 350, 750 or 1500 mg;
 (b) administered in a dosing schedule of once per week, once every two weeks, or once every three weeks; and/or
 (c) administered in a dosing schedule of once every 7 days or once every 14 days.

20. The method of claim 1, wherein the C1013G mutation is detected by a polymerase chain reaction (PCR) assay, a reverse transcriptase-polymerase chain reaction (RT-PCR) assay, a nucleic acid hybridization assay, or by DNA sequencing.

21. The method of claim 20, wherein:
 (a) the PCR assay is a real-time allele-specific PCR (AS-PCR) assay; and/or
 (b) the DNA sequencing is whole genome DNA sequencing.

22. A method for treating a subject afflicted with C1013G/CXCR4-associated Waldenström's macroglobulinemia, which method comprises administering to the subject a therapeutically effective amount of an antibody or an antigen-binding portion thereof that specifically binds to a C-X-C chemokine receptor type 4 (CXCR4) receptor expressed on the surface of a C1013G/CXCR4-associated Waldenström's macroglobulinemia cell, the subject having been selected on the basis that the Waldenström's macroglobulinemia cells of the subject are determined to carry the C1013G mutation in the CXCR4 gene.

23. A method for selecting a Waldenström's macroglobulinemia patient for treatment with an antibody or an antigen-binding portion thereof that specifically binds to a C-X-C chemokine receptor type 4 (CXCR4) receptor expressed on the surface of a Waldenström's macroglobulinemia cell, which method comprises:
 (a) assessing whether cells in a test tissue sample obtained from a Waldenström's macroglobulinemia patient carry the C1013G mutation in the CXCR4 gene; and
 (b) selecting the patient for treatment based on a determination that the Waldenström's macroglobulinemia cells carry the C1013G mutation in the CXCR4 gene.

* * * * *

SEQUENCE LISTING

<160> NUMBER OF SEQ ID NOS: 51

<210> SEQ ID NO 1
<211> LENGTH: 5
<212> TYPE: PRT
<213> ORGANISM: Homo sapiens

<400> SEQUENCE: 1

Ser Tyr Ser Met Asn
1               5

<210> SEQ ID NO 2
<211> LENGTH: 5
<212> TYPE: PRT
<213> ORGANISM: Homo sapiens

<400> SEQUENCE: 2

Ser Tyr Ser Met Asn
1               5

<210> SEQ ID NO 3
<211> LENGTH: 5
<212> TYPE: PRT
<213> ORGANISM: Homo sapiens

<400> SEQUENCE: 3

Ser Tyr Ser Met Asn
1               5

<210> SEQ ID NO 4
<211> LENGTH: 5
<212> TYPE: PRT
<213> ORGANISM: Homo sapiens

<400> SEQUENCE: 4

Ser Tyr Ser Met Asn
1               5

<210> SEQ ID NO 5
<211> LENGTH: 17
<212> TYPE: PRT
<213> ORGANISM: Homo sapiens

<400> SEQUENCE: 5

Tyr Ile Ser Ser Arg Ser Arg Thr Ile Tyr Tyr Ala Asp Ser Val Lys
1               5                   10                  15

Gly

<210> SEQ ID NO 6
<211> LENGTH: 17
<212> TYPE: PRT
<213> ORGANISM: Homo sapiens

<400> SEQUENCE: 6

Tyr Ile Ser Ser Arg Ser Arg Ser Ile Tyr Tyr Ala Asp Ser Val Lys
1               5                   10                  15

Gly

<210> SEQ ID NO 7
<211> LENGTH: 17
<212> TYPE: PRT
<213> ORGANISM: Homo sapiens

<400> SEQUENCE: 7

```
Tyr Ile Ser Ser Arg Ser Lys Thr Ile Tyr Tyr Ala Asp Ser Val Lys
1               5                   10                  15

Gly

<210> SEQ ID NO 8
<211> LENGTH: 17
<212> TYPE: PRT
<213> ORGANISM: Homo sapiens

<400> SEQUENCE: 8

Tyr Ile Ser Ser Arg Ser Arg Thr Ile Tyr Tyr Ala Asp Ser Val Lys
1               5                   10                  15

Gly

<210> SEQ ID NO 9
<211> LENGTH: 16
<212> TYPE: PRT
<213> ORGANISM: Homo sapiens

<400> SEQUENCE: 9

Asp Tyr Gly Gly Gln Pro Pro Tyr Tyr Tyr Tyr Gly Met Asp Val
1               5                   10                  15

<210> SEQ ID NO 10
<211> LENGTH: 16
<212> TYPE: PRT
<213> ORGANISM: Homo sapiens

<400> SEQUENCE: 10

Asp Tyr Gly Gly Gln Pro Pro Tyr Tyr Tyr Tyr Gly Met Asp Val
1               5                   10                  15

<210> SEQ ID NO 11
<211> LENGTH: 16
<212> TYPE: PRT
<213> ORGANISM: Homo sapiens

<400> SEQUENCE: 11

Asp Tyr Gly Gly Gln Pro Pro Tyr Tyr Tyr Tyr Gly Met Asp Val
1               5                   10                  15

<210> SEQ ID NO 12
<211> LENGTH: 16
<212> TYPE: PRT
<213> ORGANISM: Homo sapiens

<400> SEQUENCE: 12

Asp Tyr Gly Gly Gln Pro Pro Tyr His Tyr Tyr Gly Met Asp Val
1               5                   10                  15

<210> SEQ ID NO 13
<211> LENGTH: 11
<212> TYPE: PRT
<213> ORGANISM: Homo sapiens

<400> SEQUENCE: 13

Arg Ala Ser Gln Gly Ile Ser Ser Trp Leu Ala
1               5                   10

<210> SEQ ID NO 14
<211> LENGTH: 11
<212> TYPE: PRT
<213> ORGANISM: Homo sapiens
```

```
<400> SEQUENCE: 14

Arg Ala Ser Gln Gly Ile Ser Ser Trp Leu Ala
1               5                   10

<210> SEQ ID NO 15
<211> LENGTH: 11
<212> TYPE: PRT
<213> ORGANISM: Homo sapiens

<400> SEQUENCE: 15

Arg Thr Ser Gln Gly Ile Ser Ser Trp Leu Ala
1               5                   10

<210> SEQ ID NO 16
<211> LENGTH: 11
<212> TYPE: PRT
<213> ORGANISM: Homo sapiens

<400> SEQUENCE: 16

Arg Ala Ser Gln Gly Ile Ser Asn Trp Leu Ala
1               5                   10

<210> SEQ ID NO 17
<211> LENGTH: 7
<212> TYPE: PRT
<213> ORGANISM: Homo sapiens

<400> SEQUENCE: 17

Ala Ala Ser Ser Leu Gln Ser
1               5

<210> SEQ ID NO 18
<211> LENGTH: 7
<212> TYPE: PRT
<213> ORGANISM: Homo sapiens

<400> SEQUENCE: 18

Ala Ala Ser Ser Leu Gln Ser
1               5

<210> SEQ ID NO 19
<211> LENGTH: 7
<212> TYPE: PRT
<213> ORGANISM: Homo sapiens

<400> SEQUENCE: 19

Ala Ala Ser Ser Leu Gln Ser
1               5

<210> SEQ ID NO 20
<211> LENGTH: 7
<212> TYPE: PRT
<213> ORGANISM: Homo sapiens

<400> SEQUENCE: 20

Ala Ala Ser Ser Leu Gln Ser
1               5

<210> SEQ ID NO 21
<211> LENGTH: 9
<212> TYPE: PRT
<213> ORGANISM: Homo sapiens

<400> SEQUENCE: 21
```

Gln Gln Tyr Asn Ser Tyr Pro Arg Thr
1               5

<210> SEQ ID NO 22
<211> LENGTH: 9
<212> TYPE: PRT
<213> ORGANISM: Homo sapiens

<400> SEQUENCE: 22

Gln Gln Tyr Asn Ser Tyr Pro Arg Thr
1               5

<210> SEQ ID NO 23
<211> LENGTH: 9
<212> TYPE: PRT
<213> ORGANISM: Homo sapiens

<400> SEQUENCE: 23

Gln Gln Tyr Asn Ser Tyr Pro Arg Thr
1               5

<210> SEQ ID NO 24
<211> LENGTH: 9
<212> TYPE: PRT
<213> ORGANISM: Homo sapiens

<400> SEQUENCE: 24

Gln Gln Tyr Asn Ser Tyr Pro Arg Thr
1               5

<210> SEQ ID NO 25
<211> LENGTH: 125
<212> TYPE: PRT
<213> ORGANISM: Homo sapiens

<400> SEQUENCE: 25

Gln Val Gln Leu Val Gln Ser Gly Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Tyr Tyr Tyr Tyr Gly Met
            100                 105                 110

Asp Val Trp Gly Gln Gly Thr Thr Val Thr Val Ser Ser
        115                 120                 125

<210> SEQ ID NO 26
<211> LENGTH: 125
<212> TYPE: PRT
<213> ORGANISM: Homo sapiens

<400> SEQUENCE: 26

Gln Val Gln Leu Val Gln Ser Gly Gly Gly Leu Val Gln Pro Gly Gly
1               5                   10                  15

```
Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Arg Ser Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
            115                 120                 125
```

```
<210> SEQ ID NO 27
<211> LENGTH: 125
<212> TYPE: PRT
<213> ORGANISM: Homo sapiens

<400> SEQUENCE: 27

Glu Val Gln Leu Val Gln Ser Gly Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Lys Thr Ile Tyr Tyr Ala Asp Ser Val
        50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
            115                 120                 125
```

```
<210> SEQ ID NO 28
<211> LENGTH: 125
<212> TYPE: PRT
<213> ORGANISM: Homo sapiens

<400> SEQUENCE: 28

Glu Val Gln Leu Val Gln Ser Gly Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Arg Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95
```

```
Ala Arg Asp Tyr Gly Gly Gln Pro Pro Tyr His Tyr Tyr Gly Met
            100                 105                 110

Asp Val Trp Gly Gln Gly Thr Thr Val Thr Val Ser Ser
            115                 120             125

<210> SEQ ID NO 29
<211> LENGTH: 107
<212> TYPE: PRT
<213> ORGANISM: Homo sapiens

<400> SEQUENCE: 29

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Val Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 30
<211> LENGTH: 107
<212> TYPE: PRT
<213> ORGANISM: Homo sapiens

<400> SEQUENCE: 30

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 31
<211> LENGTH: 107
<212> TYPE: PRT
<213> ORGANISM: Homo sapiens

<400> SEQUENCE: 31

Val Ile Trp Val Thr Gln Ser Pro Ser Ser Leu Ser Ala Ser Val Gly
1               5                   10                  15

Asp Arg Val Thr Ile Thr Cys Thr Ser Gln Gly Ile Ser Ser Trp
            20                  25                  30
```

```
Leu Ala Trp Tyr Gln Gln Lys Pro Glu Lys Ala Pro Glu Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Homo sapiens

<400> SEQUENCE: 32

Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Trp
             20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105

<210> SEQ ID NO 33
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 33 cag gtg cag ctg gtg cag tct ggg gga ggc ttg gta cag cct ggg ggg     48
Gln Val Gln Leu Val Gln Ser Gly Gly Gly Leu Val Gln Pro Gly Gly
 1               5                  10                  15 tcc ctg aga ctc tcc tgt gca gcc gct gga ttc acc ttc agt agc tat     96
Ser Leu Arg Leu Ser Cys Ala Ala Ala Gly Phe Thr Phe Ser Ser Tyr
             20                  25                  30 agc atg aac tgg gtc cgc cag gct cca ggg aag ggg ctg gag tgg gtt    144
Ser Met Asn Trp Val Arg Gln Ala Pro Gly Lys Gly Leu Glu Trp Val
             35                  40                  45 tca tac att agt agt aga agt aga acc ata tac tac gca gac tct gtg    192
Ser Tyr Ile Ser Ser Arg Ser Arg Thr Ile Tyr Tyr Ala Asp Ser Val
 50                  55                  60 aag ggc cga ttc acc atc tcc aga gac aat gcc aag aac tca ctg tat    240
Lys Gly Arg Phe Thr Ile Ser Arg Asp Asn Ala Lys Asn Ser Leu Tyr
 65                  70                  75                  80 ctg caa atg aac agc ctg aga gac gag gac acg gct gtg tat tac tgt    288
Leu Gln Met Asn Ser Leu Arg Asp Glu Asp Thr Ala Val Tyr Tyr Cys
                 85                  90                  95
```

```
gcg aga gat tac ggt ggt caa ccc cct tac tac tac tac ggt atg      336
Ala Arg Asp Tyr Gly Gly Gln Pro Pro Tyr Tyr Tyr Tyr Gly Met
            100                 105                 110 gac gtc tgg ggc caa ggg acc acg gtc acc gtc tcc tca              375
Asp Val Trp Gly Gln Gly Thr Thr Val Thr Val Ser Ser
        115                 120                 125

<210> SEQ ID NO 34
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 34 cag gtg cag ctg gtg cag tct ggg gga ggc ttg gta cag cct ggg ggg  48
Gln Val Gln Leu Val Gln Ser Gly Gly Gly Leu Val Gln Pro Gly Gly
 1               5                  10                  15 tcc ctg aga ctc tcc tgt gca gcc gct gga ttc acc ttc agt agc tat  96
Ser Leu Arg Leu Ser Cys Ala Ala Ala Gly Phe Thr Phe Ser Ser Tyr
             20                  25                  30 agc atg aac tgg gtc cgc cag gct cca ggg aag ggg ctg gag tgg gtt  144
Ser Met Asn Trp Val Arg Gln Ala Pro Gly Lys Gly Leu Glu Trp Val
         35                  40                  45 tca tac att agt agt aga agt aga agc ata tac tac gca gac tct gtg  192
Ser Tyr Ile Ser Ser Arg Ser Arg Ser Ile Tyr Tyr Ala Asp Ser Val
     50                  55                  60 aag ggc cga ttc acc atc tcc aga gac aat gcc aag aac tca ctg tac  240
Lys Gly Arg Phe Thr Ile Ser Arg Asp Asn Ala Lys Asn Ser Leu Tyr
 65                  70                  75                  80 ctg caa atg aac agc ctg aga gac gag gac acg gct gtg tat tac tgt  288
Leu Gln Met Asn Ser Leu Arg Asp Glu Asp Thr Ala Val Tyr Tyr Cys
                 85                  90                  95 gcg aga gat tac ggt ggt caa ccc cct tac tac tac tac ggt atg      336
Ala Arg Asp Tyr Gly Gly Gln Pro Pro Tyr Tyr Tyr Tyr Gly Met
            100                 105                 110 gac gtc tgg ggc caa ggg acc acg gtc acc gtc tcc tca              375
Asp Val Trp Gly Gln Gly Thr Thr Val Thr Val Ser Ser
        115                 120                 125

<210> SEQ ID NO 35
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 35 gag gtg cag ctg gtg cag tct ggg gga ggc ttg gta cag cct ggg ggg  48
Glu Val Gln Leu Val Gln Ser Gly Gly Gly Leu Val Gln Pro Gly Gly
 1               5                  10                  15 tcc ctg aga ctc tcc tgt gca gcc gct gga ttc acc ttc agt agc tat  96
Ser Leu Arg Leu Ser Cys Ala Ala Ala Gly Phe Thr Phe Ser Ser Tyr
             20                  25                  30 agc atg aac tgg gtc cgc cag gct cca ggg aag ggg ctg gag tgg gtt  144
Ser Met Asn Trp Val Arg Gln Ala Pro Gly Lys Gly Leu Glu Trp Val
         35                  40                  45 tca tac att agt agt cgt agt aaa acc ata tac tac gca gac tct gtg  192
Ser Tyr Ile Ser Ser Arg Ser Lys Thr Ile Tyr Tyr Ala Asp Ser Val
     50                  55                  60 aag ggc cga ttc acc atc tcc aga gac aat gcc agg aac tca ctg tat  240
```

| | | | | | | | | | | | | | | | | |
|---|---|---|---|---|---|---|---|---|---|---|---|---|---|---|---|---|
| | Lys | Gly | Arg | Phe | Thr | Ile | Ser | Arg | Asp | Asn | Ala | Arg | Asn | Ser | Leu | Tyr |
| | 65 | | | | 70 | | | | 75 | | | | 80 | | | |

```
ctg caa atg aac agc ctg aga gac gag gac acg gct gtg tat tac tgt       288
Leu Gln Met Asn Ser Leu Arg Asp Glu Asp Thr Ala Val Tyr Tyr Cys
                85                  90                  95 gcg aga gat tac ggt ggt caa ccc cct tac tac tac tac ggt atg           336
Ala Arg Asp Tyr Gly Gly Gln Pro Pro Tyr Tyr Tyr Tyr Gly Met
            100                 105                 110 gac gtc tgg ggc caa ggg acc acg gtc acc gtc tcc tca                   375
Asp Val Trp Gly Gln Gly Thr Thr Val Thr Val Ser Ser
            115                 120                 125

<210> SEQ ID NO 36
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 36 gag gtg cag ctg gtg cag tct ggg gga ggc ttg gta cag cct ggg ggg       48
Glu Val Gln Leu Val Gln Ser Gly Gly Gly Leu Val Gln Pro Gly Gly
1               5                   10                  15 tcc ctg aga ctc tcc tgt gca gcc gct gga ttc acc ttc agt agc tat       96
Ser Leu Arg Leu Ser Cys Ala Ala Ala Gly Phe Thr Phe Ser Ser Tyr
                20                  25                  30 agc atg aac tgg gtc cgc cag gct cca ggg aag ggg ctg gag tgg gtt      144
Ser Met Asn Trp Val Arg Gln Ala Pro Gly Lys Gly Leu Glu Trp Val
            35                  40                  45 tca tac att agt agt aga agt aga acc ata tac tac gca gac tct gtg      192
Ser Tyr Ile Ser Ser Arg Ser Arg Thr Ile Tyr Tyr Ala Asp Ser Val
        50                  55                  60 aag ggc cga ttc acc atc tcc aga gac aat gcc aag aac tca ctg tat      240
Lys Gly Arg Phe Thr Ile Ser Arg Asp Asn Ala Lys Asn Ser Leu Tyr
65                  70                  75                  80 ctg caa atg aac agc ctg aga gac gag gac acg gct gtg tat tac tgt      288
Leu Gln Met Asn Ser Leu Arg Asp Glu Asp Thr Ala Val Tyr Tyr Cys
                85                  90                  95 gcg aga gat tac ggt ggt caa ccc cct tac cac tac tac ggt atg          336
Ala Arg Asp Tyr Gly Gly Gln Pro Pro Tyr His Tyr Tyr Gly Met
            100                 105                 110 gac gtc tgg ggc caa ggg acc acg gtc acc gtc tcc tca                  375
Asp Val Trp Gly Gln Gly Thr Thr Val Thr Val Ser Ser
            115                 120                 125

<210> SEQ ID NO 37
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 37 gcc atc cgg atg acc cag tct cca tcc tca ctg tct gca tct gta gga      48
Ala Ile Arg Met Thr Gln Ser Pro Ser Ser Leu Ser Ala Ser Val Gly
1               5                   10                  15 gac aga gtc acc atc act tgt cgg gcg agt cag ggt att agc agc tgg      96
Asp Arg Val Thr Ile Thr Cys Arg Ala Ser Gln Gly Ile Ser Ser Trp
                20                  25                  30 tta gcc tgg tat cag cag aaa cca gag aaa gcc cct aag tcc ctg atc     144
Leu Ala Trp Tyr Gln Gln Lys Pro Glu Lys Ala Pro Lys Ser Leu Ile
```

```
                35                  40                  45
tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gta act tat tac tgc caa cag tat aat agt tac cct cgg    288
Glu Asp Phe Val Thr Tyr Tyr Cys Gln Gln Tyr Asn Ser Tyr Pro Arg
                 85                  90                  95 acg ttc ggc caa ggg acc aag gtg gaa atc aaa                        321
Thr Phe Gly Gln Gly Thr Lys Val Glu Ile Lys
                100                 105
```

<210> SEQ ID NO 38
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 38

```
gaa att gtg ctc acc cag tct cca tcc tca ctg tct gca tct gta gga     48
Glu Ile Val Leu Thr Gln Ser Pro Ser Ser Leu Ser Ala Ser Val Gly
 1               5                  10                  15 gac aga gtc acc atc act tgt cgg gcg agt cag ggt att agc agc tgg     96
Asp Arg Val Thr Ile Thr Cys Arg Ala Ser Gln Gly Ile Ser Ser Trp
             20                  25                  30 tta gcc tgg tat cag cag aaa cca gag aaa gcc cct aag tcc ctg atc    144
Leu Ala Trp Tyr Gln Gln Lys Pro Glu Lys Ala Pro Lys Ser Leu Ile
         35                  40                  45 tat gct gca tcc agt ttg caa agt ggg gtc cca cca agg ttc agc ggc    192
Tyr Ala Ala Ser Ser Leu Gln Ser Gly Val Pro Pro Arg Phe Ser Gly
     50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac cct cgg    288
Glu Asp Phe Ala Thr Tyr Tyr Cys Gln Gln Tyr Asn Ser Tyr Pro Arg
                 85                  90                  95 acg ttc ggc caa ggg acc aag gtg gaa atc aaa                        321
Thr Phe Gly Gln Gly Thr Lys Val Glu Ile Lys
                100                 105
```

<210> SEQ ID NO 39
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 39

```
gtc atc tgg gtg acc cag tct cca tcc tca ctg tct gca tct gta gga     48
Val Ile Trp Val Thr Gln Ser Pro Ser Ser Leu Ser Ala Ser Val Gly
 1               5                  10                  15 gac aga gtc acc atc act tgt cgg acg agt cag ggt att agc agc tgg     96
Asp Arg Val Thr Ile Thr Cys Arg Thr Ser Gln Gly Ile Ser Ser Trp
             20                  25                  30 tta gcc tgg tat cag cag aaa cca gag aaa gcc cct gag ctc ctg atc    144
Leu Ala Trp Tyr Gln Gln Lys Pro Glu Lys Ala Pro Glu Leu Leu Ile
         35                  40                  45
```

```
tat gct gca tcc agt ttg caa agt ggg gtc cca tca agg ttc agc ggc        192
Tyr Ala Ala Ser Ser Leu Gln Ser Gly Val Pro Ser Arg Phe Ser Gly
            50                  55                  60 agt gga tct ggg aca gat ttc act ctc acc atc agc agc ctg cag cct        240
Ser Gly Ser Gly Thr Asp Phe Thr Leu Thr Ile Ser Ser Leu Gln Pro
65                  70                  75                  80 gaa gat ttt gca act tat tac tgc caa cag tat aat agt tac cct cgg        288
Glu Asp Phe Ala Thr Tyr Tyr Cys Gln Gln Tyr Asn Ser Tyr Pro Arg
                85                  90                  95 acg ttc ggc caa ggg acc aag gtg gaa atc aaa                            321
Thr Phe Gly Gln Gly Thr Lys Val Glu Ile Lys
            100                 105

<210> SEQ ID NO 40
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 40 gaa att gtg ctc acc cag tct cca tcc tca ctg tct gca tct gta ggg         48
Glu Ile Val Leu Thr Gln Ser Pro Ser Ser Leu Ser Ala Ser Val Gly
1               5                   10                  15 gac aga gtc acc atc act tgt cgg gcg agt cag ggt att agc aac tgg         96
Asp Arg Val Thr Ile Thr Cys Arg Ala Ser Gln Gly Ile Ser Asn Trp
            20                  25                  30 tta gcc tgg tat cag cag aaa cca gag aaa gcc cct aag tcc ctg atc        144
Leu Ala Trp Tyr Gln Gln Lys Pro Glu Lys Ala Pro Lys Ser Leu Ile
        35                  40                  45 tat gct gca tcc agt ttg caa agt ggg gtc cca tca agg ttc agc ggc        192
Tyr Ala Ala Ser Ser Leu Gln Ser Gly Val Pro Ser Arg Phe Ser Gly
            50                  55                  60 agt gga tct ggg aca gat ttc act ctc acc atc agc agc ctg cag cct        240
Ser Gly Ser Gly Thr Asp Phe Thr Leu Thr Ile Ser Ser Leu Gln Pro
65                  70                  75                  80 gaa gat ttt gcg act tat tac tgc caa cag tat aat agt tac cct cgg        288
Glu Asp Phe Ala Thr Tyr Tyr Cys Gln Gln Tyr Asn Ser Tyr Pro Arg
                85                  90                  95 acg ttc ggc caa ggg acc aag gtg gaa atc aaa                            321
Thr Phe Gly Gln Gly Thr Lys Val Glu Ile Lys
            100                 105

<210> SEQ ID NO 41
<211> LENGTH: 125
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

-continued

```
Leu Gln Met Asn Ser Leu Arg Asp Glu Asp Thr Ala Val Tyr Tyr Cys
                 85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
            115                 120                 125
```

<210> SEQ ID NO 42
<211> LENGTH: 125
<212> TYPE: PRT
<213> ORGANISM: Homo sapiens

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
            115                 120                 125
```

<210> SEQ ID NO 43
<211> LENGTH: 125
<212> TYPE: PRT
<213> ORGANISM: Homo sapiens

<400> SEQUENCE: 43

```
Glu Val Gln Leu Val Glu Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Lys Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
            115                 120                 125
```

<210> SEQ ID NO 44
<211> LENGTH: 125
<212> TYPE: PRT
<213> ORGANISM: Homo sapiens

<400> SEQUENCE: 44

Glu Val Gln Leu Val Gln Ser Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr His Tyr Tyr Tyr Gly Met
            100                 105                 110

Asp Val Trp Gly Gln Gly Thr Thr Val Thr Val Ser Ser
        115                 120                 125

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Val Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg

```
                    85                  90                  95

Thr Phe Gly Gln Gly Thr Lys Val Glu Ile Lys
            100                 105

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Ser Ser Trp
            20                  25                  30

Leu Ala Trp Tyr Gln Gln Lys Pro Glu Lys Ala Pro Glu Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 48
<211> LENGTH: 107
<212> TYPE: PRT
<213> ORGANISM: Homo sapiens

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 49
<211> LENGTH: 98
<212> TYPE: PRT
<213> ORGANISM: Homo sapiens

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45
```

```
Ser Tyr Ile Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 50
<211> LENGTH: 95
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 51
<211> LENGTH: 352
<212> TYPE: PRT
<213> ORGANISM: Homo sapiens

<400> SEQUENCE: 51

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175
```

-continued

| | | | | | | | | | | | | | | |
|---|---|---|---|---|---|---|---|---|---|---|---|---|---|---|
| Val | Ser | Glu | Ala | Asp | Asp | Arg | Tyr | Ile | Cys | Asp | Arg | Phe | Tyr | Pro | Asn |
| | | | 180 | | | | | 185 | | | | | 190 | | |
| Asp | Leu | Trp | Val | Val | Val | Phe | Gln | Phe | Gln | His | Ile | Met | Val | Gly | Leu |
| | | 195 | | | | | 200 | | | | | 205 | | | |
| Ile | Leu | Pro | Gly | Ile | Val | Ile | Leu | Ser | Cys | Tyr | Cys | Ile | Ile | Ile | Ser |
| | 210 | | | | | 215 | | | | | 220 | | | | |
| Lys | Leu | Ser | His | Ser | Lys | Gly | His | Gln | Lys | Arg | Lys | Ala | Leu | Lys | Thr |
| 225 | | | | | 230 | | | | | 235 | | | | | 240 |
| Thr | Val | Ile | Leu | Ile | Leu | Ala | Phe | Phe | Ala | Cys | Trp | Leu | Pro | Tyr | Tyr |
| | | | | 245 | | | | | 250 | | | | | 255 | |
| Ile | Gly | Ile | Ser | Ile | Asp | Ser | Phe | Ile | Leu | Leu | Glu | Ile | Ile | Lys | Gln |
| | | | 260 | | | | | 265 | | | | | 270 | | |
| Gly | Cys | Glu | Phe | Glu | Asn | Thr | Val | His | Lys | Trp | Ile | Ser | Ile | Thr | Glu |
| | | | 275 | | | | | 280 | | | | | 285 | | |
| Ala | Leu | Ala | Phe | Phe | His | Cys | Cys | Leu | Asn | Pro | Ile | Leu | Tyr | Ala | Phe |
| | | 290 | | | | | 295 | | | | | 300 | | | |
| Leu | Gly | Ala | Lys | Phe | Lys | Thr | Ser | Ala | Gln | His | Ala | Leu | Thr | Ser | Val |
| 305 | | | | | 310 | | | | | 315 | | | | | 320 |
| Ser | Arg | Gly | Ser | Ser | Leu | Lys | Ile | Leu | Ser | Lys | Gly | Lys | Arg | Gly | Gly |
| | | | | 325 | | | | | 330 | | | | | 335 | |
| His | Ser | Ser | Val | Ser | Thr | Glu | Ser | Glu | Ser | Ser | Ser | Phe | His | Ser | Ser |
| | | | 340 | | | | | 345 | | | | | 350 | | |